US008337859B2

(12) United States Patent
Silvestre et al.

(10) Patent No.: US 8,337,859 B2
(45) Date of Patent: *Dec. 25, 2012

(54) VECTORS FOR MULTIPLE GENE EXPRESSION

(75) Inventors: Nathalie Silvestre, Ergersheim (FR); Doris Schmitt, Plobsheim (FR)

(73) Assignee: Transgene S.A., Illkirch (FR)

(*) Notice: Subject to any disclaimer, the term of this patent is extended or adjusted under 35 U.S.C. 154(b) by 309 days.

This patent is subject to a terminal disclaimer.

(21) Appl. No.: 12/599,971

(22) PCT Filed: Jan. 29, 2008

(86) PCT No.: PCT/EP2008/051031
§ 371 (c)(1),
(2), (4) Date: Nov. 12, 2009

(87) PCT Pub. No.: WO2008/138648
PCT Pub. Date: Nov. 20, 2008

(65) Prior Publication Data
US 2010/0303838 A1    Dec. 2, 2010

(30) Foreign Application Priority Data

May 15, 2007   (EP) ..................... 07360019

(51) Int. Cl.
| A61K 39/12 | (2006.01) |
| A61K 39/235 | (2006.01) |
| A61K 39/285 | (2006.01) |
| A61K 48/00 | (2006.01) |
| C12N 15/37 | (2006.01) |
| C12N 15/861 | (2006.01) |
| C12N 15/863 | (2006.01) |
| C12N 15/85 | (2006.01) |
| C12N 7/01 | (2006.01) |
| C12N 5/10 | (2006.01) |

(52) U.S. Cl. ................. 424/199.1; 424/93.2; 424/204.1; 514/44 R; 435/320.1; 435/235.1; 435/325

(58) Field of Classification Search .................. None
See application file for complete search history.

(56) References Cited

U.S. PATENT DOCUMENTS

| 5,719,054 A * | 2/1998 | Boursnell et al. .......... 435/320.1 |
| 6,294,547 B1 | 9/2001 | Oka et al. |
| 6,410,298 B1 | 6/2002 | Crouzet et al. |
| 6,884,786 B1 | 4/2005 | Kieny et al. |
| 2005/0075303 A1 | 4/2005 | Neeper et al. |

FOREIGN PATENT DOCUMENTS

| WO | WO 92/16636 A | 10/1992 |
| WO | WO 99/00388 A1 | 1/1999 |
| WO | WO 99/03885 | 1/1999 |
| WO | WO 03/018055 A | 3/2003 |

OTHER PUBLICATIONS

Ayares et al (PNAS 83:5199-5203, 1986).*
Rubnitz et al (Molecular and Cellular Biology 4:2253-2258, 1984).*
Stary et al (Journal of Virology 63:3837-3843, 1989).*
Viviane Bechtold et al., "Human Papillomavirus Type 16 E2 Protein Has no Effect on Transcription From Episomal Viral DNA," *Journal of Virology*, Feb. 2003, pp. 2021-2028, vol. 77, No. 3, American Society for Microbiology, Washington, D.C.
Mary A. Bedell et al., "The E6-E7 Region of Human Papillomavirus Type 18 is Sufficient for Transformation of NIH 3T3 and Rat-1 Cells," *Journal of Virology*, Nov. 1987, pp. 3635-3640, vol. 61, No. 11, American Society for Microbiology, Washington, D.C.
Jane L. Brokaw et al., "Amino Acids Critical for the Functions of the Bovine Papillomavirus Type 1 E2 Transactivator," *Journal of Virology*, Jan. 1996, pp. 23-29, vol. 70, No. 1, American Society for Microbiology, Washington, D.C.
S. T. Cole et al., "Nucleotide Sequence and Comparative Analysis of the Human Papillomavirus Type 18 Genome: Phylogeny of Papillomaviruses and Repeated Structure of the E6 and E7 Gene Products," *Journal of Molecular Biology*, 1987, pp. 599-608, vol. 193, Academic Press Inc., London, Great Britain.
Tim Crook et al., "Degradation of p53 can be Targeted by HPV E6 Sequences Distinct From Those Required for p53 Binding and Trans-Activation," *Cell*, Nov. 1, 1991, pp. 547-556, vol. 67, No. 3, Cell Press, Cambridge, MA.
Ethel-Michele De Villiers et al., "Classification of Papillomaviruses," *Virology*, 2004, pp. 17-27, vol. 324, Elsevier Inc.
Caroline Demeret et al., "Control of HPV 18 DNA Replication by Cellular and Viral Transcription Factors," *Nucleic Acids Research*, 1995, pp. 4777-4784, vol. 23, No. 23, Oxford University Press.
Christian Desaintes et al., "Control of Papillomavirus DNA Replication and Transcription," *Seminars in Cancer Biology*, Dec. 1996, pp. 339-347, vol. 7, No. 6, Academic Press Ltd., Great Britain.
Frits Fallaux et al., "New Helper Cells and Matched Early Region 1-Deleted Adenovirus Vectors Prevent Generation of Replication—Competent Adenoviruses," *Human Gene Therapy*, Sep. 1, 1998, pp. 1909-1917, vol. 9, Mary Ann Liebert, Inc.
Mary K. Ferguson et al., "Genetic Analysis of the Activation Domain of Bovine Papillomavirus Protein E2: Its Role in Transcription and Replication," *Journal of Virology*, Jul. 1996, pp. 4193-4199, vol. 70, No. 7, American Society for Microbiology, Washington, D.C.

(Continued)

*Primary Examiner* — Mary E Mosher
(74) *Attorney, Agent, or Firm* — Buchanan Ingersoll & Rooney PC

(57) ABSTRACT

The present invention provides a vector for expressing at least a first and a second nucleic acid molecules which exhibit a percentage of homology of approximately 80% or greater than 80% over a portion of 40 or more continuous nucleotides and wherein said first nucleic acid molecule and/or said second nucleic acid molecule is modified so as to reduce said percentage of homology to less than 75%. The present invention also relates to substantially isolated nucleic acid molecules comprising a nucleotide sequence as defined in any of SEQ ID NO: 9-15 and 66-69. It also provides a host cell and a pharmaceutical composition comprising such a nucleic acid molecule or vector as well as their use for therapeutic or preventive purposes.

26 Claims, 3 Drawing Sheets

OTHER PUBLICATIONS

F. L. Graham et al., "Characteristics of a Human Cell Line Transformed by DNA From Human Adenovirus Type 5," *Journal of General Virology*, Feb. 1977, pp. 59-72, vol. 36, Great Britain.

Donald V. Heck et al., "Efficiency of Binding the Retinoblastoma Protein Correlates With the Transforming Capacity of the E7 Oncoproteins of the Human Papillomaviruses," *Biochemistry*, May 1992, pp. 4442-4446, vol. 89, No. 10, Proceedings of the National Academy of Sciences of the United States of America, Washington, D.C.

Peter M. Howley, "Papillomavirinae: The Viruses and Their Replication," *Fields Virology*, 1996, pp. 2045-2076, Ed. 3, Lippincott-Raven Publishers, Philadelphia, PA.

Fiona J. Hughes et al., "E1 Protein of Human Papillomavirus is a DNA Helicase/ATPase," *Nucleic Acids Research*, 1993, pp. 5817-5823, vol. 21, No. 25, Oxford University Press.

Tadahito Kanda et al., "Human Papillomavirus Type 16 Open Reading Frame E7 Encodes a Transforming Gene for Rat 3Y1 Cells," *Journal of Virology*, Feb. 1988, pp. 610-613, vol. 62, No. 2, American Society for Microbiology, Washington, D.C.

Iain M. Kennedy et al., "A Negative Regulatory Element in the Human Papillomavirus Type 16 Genome Acts at the Level of Late mRNA Stability," *Journal of Virology*, Apr. 1991, pp. 2093-2097, vol. 65, No. 4, American Society for Microbiology, Washington, D.C.

Alison A. McBride et al., "E2 Polypeptides Encoded by Bovine Papillomavirus Type 1 Form Dimers Through the Common Carboxyl-terminal Domain: Transactivation is Mediated by the Conserved Amino-Terminal Domain," *Biochemistry*, Jan. 1989, pp. 510-514, vol. 86, No. 2, Proceedings of the National Academy of Sciences of the United States of America, Washington, D.C.

Karl Münger et al., "Complex Formation of Human Papillomavirus E7 Proteins With the Retinoblastoma Tumor Suppressor Gene Product," *The EMBO Journal*, Dec. 1989, pp. 4099-4105, vol. 8, No. 13, European Molecular Biology Organization, Heidelberg, Germany.

William C. Phelps et al., "Structure-Function Analysis of the Human Papillomavirus Type 16 E7 Oncoprotein," *Journal of Virology*, Apr. 1992, pp. 2418-2427, vol. 66, No. 4, American Society for Microbiology, Washington, D.C.

David Pim et al., "Mutational Analysis of HPV-18 E6 Identifies Domains Required for p53 Degradation in vitro, Abolition of p53 Transactivation in vivo and Immortalisation of Primary BMK Cells," *Oncogene*, 1994, pp. 1869-1876, vol. 9, Macmillan Press Ltd.

Hiroyuki Sakai et al., "Targeted Mutagenesis of the Human Papillomavirus Type 16 E2 Transactivation Domain Reveals Separable Transcriptional Activation and DNA Replication Functions," *Journal of Virology*, 1996, pp. 1602-1611, vol. 70, No. 3, American Society for Microbiology, Washington, D.C.

Klaus Seedorf et al., "Human Papillomavirus Type 16 DNA Sequence," *Virology*, 1985, pp. 181-185, vol. 145, Elsevier Inc.

Marc Van Ranst et al., "Phylogenetic Classification of Human Papillomaviruses: Correlation With Clinical Manifestations," *Journal of General Virology*, 1992, pp. 2653-2660, vol. 73, Society for General Microbiology.

Karen H. Vousden et al., "The E7 Open Reading Frame of Human Papillomavirus Type 16 Encodes a Transforming Gene," *Oncogene Research*, 1988. pp. 167-175, vol. 3, Harwood Academic Publishers GmbH.

Toshiharu Yasugi et al., "Two Classes of Human Papillomavirus Type 16 E1 Mutants Suggest Pleiotropic Conformational Constraints Affecting E1 Multimerization, E2 Interaction, and Interaction With Cellular Proteins," *Journal of Virology*, Aug. 1997, pp. 5942-5951, vol. 71, No. 8, American Society for Microbiology, Washington, D.C.

MacLean et al., "Optimization of Human Papillomavirus Type 16 (HPV-16) L1 Expression in Plants: Comparison of the Suitability of Different HPV-16 L1 Gene Variants and Different Cell-Compartment Localization," *Journal of General Virology*, May 1, 2007, vol. 88, No. Part 5, pp. 1460-1469, Society for General Microbiology, London, England.

\* cited by examiner

FIGURE 1

Figure 1A a) ...GCACGAGGACGAGGACAAGGAAAACGATGGTGATTCATTACCTACATTCAAGTGCGTATCTGGTCAGAACACAAATACTTTGTGA
       ||||||||||||||||||||||||||||||||||||||||||||||||||||||||
b)     ATGGTGATTCATTACCTACATTCAAGTGCGTATCTGGTCAGAACACAAATACTTTGTGAAAAATGATAGT...

Percent identity: 100

Figure 1B a) ...GCACGAGGACGAGGACAAGGAAAACGATGGTGATTCATTACCTACATTCAAGTGCGTATCTGGTCAGAACACAAATACTTTGTGA
       ||| ||| ||| ||| ||| ||| ||| ||| ||| ||| ||| ||| ||| |||
b)     ATGGAGACTCTTTGCCAACGTTTAAATGTGTCAGGACAAAATACTAACACATTATGAAAATGATAGT...

Percent identity: 69.492

Figure 2A

E6 HPV16 (SEQ ID NO:86) (a) versus E6 HPV18 (SEQ ID NO:87) (b)

```
a  ATGCACCAAAAGAGAACTGCAATGTTTCAGGACCCACAGGAGCGACCCAG  50
     |  ||    ||| ||||  |||      |||||||
b  ...............ATGGCGCGCTTTGAGGATCCAACACGGCGACCCTA  35 a  AAAGTTACCACAGTTATGCACAGAGCTGCAAACAACTATACATGATATAA  100
   |||  ||||    |   | ||||||  || ||| | ||    |  || |||
b  CAAGCTACCTGATCTGTGCACGGAACTGAACACTTCACTGCAAGACATAG  85 a  TATTAGAATGTGTGTACTGCAAGCAACAGTTACTGCGACGTGAGGTATAT  150
   |  ||   ||||| ||  ||||||  |  ||    |         |||||||| |
b  AAATAACCTGTGTATATTGCAAGACAGTATTGGAACTTACAGAGGTATTT  135 a  GACTTTGCTTTTCGGGATTTATGCATAGTATATAGAGATGGGAATCCATA  200
   || ||||||  |||     |||||||    | || |||||||| |  |  ||  |
b  GAATTTGCATTTAAAGATTTATTTGTGGTGTATAGAGACAGTATACCCCA  185 a  TGCTGTATGTGATAAATGTTTAAAGTTTTATTCTAAAATTAGTGAGTATA  250
   |||||  |||   |||||||||  ||  ||||||||||||  ||||||  ||   |
b  TGCTGCATGCCATAAATGTATAGATTTTTATTCTAGAATTAGAGAATTAA  235 a  GACATTATTGTTATAGTTTGTATGGAACAACATTAGAACAGCAATACAAC  300
   ||||||||     |   |  |||||||||      |||||  |||  | |    |||
b  GACATTATTCAGACTCTGTGTATGGAGACACATTGGAAAAACTAACTAAC  285 a  AAACCGTTGTGTGATTTGTTAATTAGGTGTATTAACTGTCAAAAGCCACT  350
   |     |||  |    ||||  |||||   |||||  |      ||  ||  || ||    |
b  ACTGGGTTATACAATTTATTAATAAGGTGCCTGCGGTGCCAGAAACCGTT  335 a  GTGTCCTGAAGAAAAGCAAAGACATCTGGACAAAAAGCAAAGATTCCATA  400
   |   |||  | |||||||   |     |||||| || |     |||| |  | ||||  || |
b  GAATCCAGCAGAAAAACTTAGACACCTTAATGAAAAACGACGATTTCACA  385 a  ATATAAGGGGTCGGTGGACCGGTCGATGTATGTCTTGTTGCAGATCATCA  450
   | |||    || |    |    |  || |    ||    ||  || ||||         |  ||
b  ACATAGCTGGGCACTATAGAGGCCAGTGCCATTCGTGCTGCAACCGAGCA  435 a  AG..............AACACGTAGAGAAACCCAGCTGTAA  477
   |             | |||  |||||||||| ||  | |||
b  CGACAGGAACGACTCCAACGACGCAGAGAAACACAAGTATAA  477
```

Figure 2B

HPV16 E6 (SEQ ID NO:86) (a) versus (SEQ ID NO:14) (b)

```
a     .........ATGCACCAAAAGAGAACTGCAATGTTTCAGGACCCACAGG  40
                  |  ||   ||| ||||  |||
b     ..................ATGGCGCGCTTTGAGGATCCAACAC  100 a     AGCGACCCAGAAAGTTACCACAGTTATGCACAGAGCTGCAAACAACTATA  90
      |||||||   |||  ||||   |  | ||||| || ||| | ||   |  |
b     GGCGACCCTACAAGCTACCTGATCTGTGCACGGAACTGAACACTTCACTG  150 a     CATGATATAATATTAGAATGTGTGTACTGCAAGCAACAGTTACTGCGACG  140
      || || |||   | ||   ||||||  || || |||   | ||      |
b     CAAGACATAGAAATAACCTGTGTATATTGTAAGACAGTATTGGAACTTAC  200 a     TGAGGTATATGACTTTGCTTTTCGGGATTTATGCATAGTATATAGAGATG  190
      |||||||  ||| |||||  |||   ||  |||  |  || ||| |  ||
b     AGAGGTATTTGAATTTGCATTTAAAGACCTATTTGTGGTGTATCGTGACA  250 a     GGAATCCATATGCTGTATGTGATAAATGTTTAAAGTTTTATTCTAAAATT  240
      |  |  ||  ||||| |  |  ||||  ||| || | ||||| |||| |||
b     GTATACCCCATGCCGCATGCCATAAGTGTATAGATTTTTACTCTAGAATC  300 a     AGTGAGTATAGACATTATTGTTATAGTTTGTATGGAACAACATTAGAACA  290
      | ||  |   || || ||||      | |||| |||   ||||| |||  |
b     AGAGAATTAAGGCACTATTCAGACTCTGTGTACGGAGACACATTGGAAAA  350 a     GCAATACAACAAACCGTTGTGTGATTTGTTAATTAGGTGTATTAACTGTC  340
      |  |    ||||   ||| |  ||||  ||||| || ||       |||
b     ACTAACTAACACTGGGTTATACAATTTATTAATAAGATGCCTGCGGTGCC  400 a     AAAAGCCACTGTGTCCTGAAGAAAAGCAAAGACATCTGGACAAAAAGCAA  390
      |  || ||     |                ||  |||||  || |  ||| ||
b     AGAAACCGTT...............GCTTAGACACCTTAATGAAAAACGA  435 a     AGATTCCATAATATAAGGGGTCGGTGGACCGGTCGATGTATGTCTTGTTG  440
      |||| ||  || |||     |||  |  |  | ||| ||   ||  || ||
b     CGATTTCACAACATAGCTGGGCACTATAGAGGCCAGTGCCATTCGTGCTG  485 a     C.....AGATCATCAAGAACACGTAGAGAAACCCAGCTGTAA........  477
      |      ||   |  || |||||   | |   || |||    |
b     CAACCGAGCACGACAGGAACGACTCCAACGACGCAGGGAGACACAAGTAA  535
```

VECTORS FOR MULTIPLE GENE EXPRESSION

CROSS-REFERENCE TO RELATED APPLICATIONS

This application is a national stage filing under 35 U.S.C. 371 of International Application No. PCT/EP2008/051031, filed on Jan. 29, 2008, which claims the priority of European Application No. 07360019.9, filed May 15, 2007, the entire contents of which are incorporated by reference herein.

This invention relates to a recombinant vector engineered for independently expressing multiple nucleotide sequences of interest which are obtained from the same organism or from closely related organisms. This invention relates to the field of recombinant nucleic acid technology for expressing multiple nucleotide sequences exhibiting homology with each other, in various prokaryotic as well as eukaryotic in vitro systems or in an animal or human subject for therapeutic or prophylactic purposes. The present invention is particularly useful in the field of immunotherapy especially for treating or preventing pathological conditions caused by infectious organisms such as papillomavirus and hepatitis virus.

Recombinant DNA technology has made it possible to express nucleotide sequences in cultured host cells or in living organisms. Several plasmid DNA and viral vectors have been generated and employed for a variety of purposes, including vaccination, gene therapy, immunotherapy and expression in cultured cells. Vectors such as adenoviral and poxviral vectors have the advantage to accommodate a large cloning capacity, with potential of expressing multiple nucleotide sequences in a wide range of host cells. Expression of multiple nucleotide sequences may be advantageous in order to improve the therapeutic efficacy provided by the encoded polypeptides (e.g. combining humoral and cellular immunity). Rather than producing a plurality of recombinant vectors engineered separately to express each of the desired nucleotide sequences, it would be advantageous to produce a single recombinant vector, at least to facilitate production steps and regulatory approval.

For example, with respect to papillomavirus infections, it would be of interest of expressing immunogenic polypeptides from several papillomavirus genotypes, in order to broaden or reinforce the host's immune response especially in subject at risk of multiple infections, e.g. HPV-16 and HPV-18. However, the nucleotide sequences encoding such immunogenic polypeptides are highly homologous between related HPV genotypes. For example, the HPV-16 E6 and HPV-18 E6 sequences which show an overall homology of 63% at the nucleotide level, nevertheless comprise particular regions of very high homology beyond 75% which may jeopardize expression of HPV-16 and HPV-18 genes from a single vector.

Moreover, when expressing polypeptides of viral origin, homologous nucleotide sequences may also arise from the overall organization of virus genome. It is rather frequent that a virus use the same nucleotide sequence to encode two different proteins through biological mechanisms such as internal translation initiation or reading frame shifting, i.e. the same sequence of DNA is translated in more than one reading frame. For example, in the HPV-16 genome, the adjacent E1 and E2 genes overlap over 59 nucleotides which are translated in different reading frames. In other words, the last 59 nucleotides of the E1 gene overlap with the first 59 nucleotides of the E2 gene.

However, the presence of homologous sequences in a vector is expected to negatively influence its stability especially during the vector production steps, leading to loss of gene sequences due to recombination events that occur between the homologous sequences. Thus, expressing HPV-16 E1 and E2 genes in a single vector involves the presence of a common portion of 59 nucleotides which could potentially lead to homologous recombination events and ultimately to loss of the sequences comprised between the E1 and E2 homologous sequences. Such undesired homologous recombination events may also occur when expressing HPV-16 and HPV-18 gene sequences in the same vector. This instability problem can render vector stock unusable, especially for human clinical trial.

In this respect, WO92/16636 propose to insert in the recombinant vector the homologous nucleotide sequences in opposite orientation with respect of each other so as to reduce the likelihood of recombination events. However, this strategy was described in connection with vaccinia virus vector and not for other recombinant vectors such as adenoviruses. Moreover, the arrangement in opposite orientation is not always possible due to possible promoter interference and construction constraint.

There is a need in the art for generating recombinant vectors capable of expressing in a host cell or subject nucleotide sequences obtained from the same or from closely related organisms, which, in the native context, contains highly homologous portions. The present invention addresses this need in providing a novel strategy designed to minimise the likelihood of the recombination events, by altering either or both of the homologous nucleotide sequences using the degeneracy of the genetic code to make them less homologous than before modification while not altering or not altering significantly the encoded amino acid sequence. The present invention permits to circumvent the deleterious effect of homologous recombination that may occur between the homologous sequences, especially during vector production steps and lead to the loss of nucleotide sequences contained in between. It has been found that the vector of the present invention is surprisingly effective in expressing E1 and E2 papillomavirus genes which in the native context share a 100% homologous portion of 59 nucleotides and surprisingly stable during the vector production steps. It has also been found that the vector of the present invention is surprisingly effective in expressing E6 and E7 genes obtained from the closely related HPV-16 and HPV-18 genotypes.

This technical problem is solved by the provision of the embodiments as defined in the claims.

Other and further aspects, features and advantages of the present invention will be apparent from the following description of the presently preferred embodiments of the invention. These embodiments are given for the purpose of disclosure.

Accordingly, in a first aspect, the present invention provides a vector comprising at least a first nucleic acid molecule encoding a first polypeptide and a second nucleic acid molecule encoding a second polypeptide wherein:

said first and second nucleic acid molecules are obtained respectively from a first and second native nucleic acid sequences which exhibit a percentage of homology of approximately 80% or greater than 80% over a portion of 40 or more continuous nucleotides, and said first nucleic acid molecule and/or said second nucleic acid molecule comprised in the vector is modified so as to reduce said percentage of homology to less than 75%.

As used herein throughout the entire application, the terms "a" and "an" are used in the sense that they mean "at least one", "at least a first", "one or more" or "a plurality" of the referenced compounds or steps, unless the context dictates otherwise. For example, the term "a cell" includes a plurality of cells including a mixture thereof.

The term "and/or" wherever used herein includes the meaning of "and", "or" and "all or any other combination of the elements connected by said term". For example, "the first nucleic acid molecule and/or the second nucleic acid molecule" means the first nucleic acid molecule, or the second nucleic acid molecule or both the first and the second nucleic acid molecules.

The term "about" or "approximately" as used herein means within 5%, preferably within 4%, and more preferably within 2% of a given value or range.

As used herein, when used to define products, compositions and methods, the term "comprising" is intended to mean that the products, compositions and methods include the referenced components or steps, but not excluding others. "Consisting essentially of" shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps. For example, a polypeptide "consists of" an amino acid sequence when the polypeptide does not contain any amino acids but the recited amino acid sequence. A polypeptide "consists essentially of" an amino acid sequence when such an amino acid sequence is present together with only a few additional amino acid residues, typically from about 1 to about 50 or so additional residues. A polypeptide "comprises" an amino acid sequence when the amino acid sequence is at least part of the final amino acid sequence of the polypeptide. Such a polypeptide can have a few up to several hundred additional amino acids residues. Such additional amino acid residues may play a role in polypeptide trafficking, facilitate polypeptide production or purification; prolong half-life, among other things. The same can be applied for nucleotide sequences.

As used herein, a "vector" may be any agent capable of delivering and expressing at least the first and second nucleic acid molecules in a host cell or subject. The vector may be extrachromosomal (e.g. episome) or integrating (for being incorporated into the host chromosomes), autonomously replicating or not, multi or low copy, double-stranded or single-stranded, naked or complexed with other molecules (e.g. vectors complexed with lipids or polymers to form particulate structures such as liposomes, lipoplexes or nanoparticles, vectors packaged in a viral capsid, and vectors immobilised onto solid phase particles, etc.). The definition of the term "vector" also encompasses vectors that have been modified to allow preferential targeting to a particular host cell. A characteristic feature of targeted vectors is the presence at their surface of a ligand capable of recognizing and binding to a cellular and surface-exposed component such as a cell-specific marker (e.g. an HPV-infected cell), a tissue-specific marker or a tumor-specific marker. The ligand can be genetically inserted into a polypeptide present on the surface of the vector (e.g. adenoviral fiber, penton, pIX as described in WO94/10323 and WO02/96939 or vaccinia p14 gene product as described in EP 1 146 125).

Within the context of the present invention, the terms "nucleic acid", "nucleic acid molecule", "polynucleotide" and "nucleotide sequence" are used interchangeably and define a polymer of any length of either polydeoxyribonucleotides (DNA) or polyribonucleotides (RNA) molecules or any combination thereof. The definition encompasses single or double-stranded, linear or circular, naturally-occurring or synthetic polynucleotides. Moreover, such polynucleotides may comprise non-naturally occurring nucleotides (e.g. methylated nucleotides and nucleotide analogs such as those described in U.S. Pat. No. 5,525,711, U.S. Pat. No. 4,711,955 or EPA 302 175) as well as chemical modifications (e.g. see WO 92/03568; U.S. Pat. No. 5,118,672) in order to increase the in vivo stability of the nucleic acid, enhance the delivery thereof, or reduce the clearance rate from the host subject. If present, modifications may be imparted before or after polymerization.

The terms "polypeptide", "peptide" and "protein" are used herein interchangeably to refer to polymers of amino acid residues which comprise 9 or more amino acids bonded via peptide bonds. The polymer can be linear, branched or cyclic. In the context of this invention, a "polypeptide" may include amino acids that are L stereoisomers (the naturally occurring form) or D stereoisomers and may include amino acids other than the common naturally occurring amino acids, such as [beta]-alanine, ornithine, or methionine sulfoxide, or amino acids modified on one or more alpha-amino, alpha-carboxyl, or side-chain, e.g., by appendage of a methyl, formyl, acetyl, glycosyl, phosphoryl, and the like. As a general indication, if the amino acid polymer is long (e.g. more than 50 amino acid residues), it is preferably referred to as a polypeptide or a protein. By way of consequence, a "peptide" refers to a fragment of about 9 to about 50 amino acids in length. In the context of the invention, a peptide preferably comprises a selected region of a naturally-occurring (or native) protein, e.g. an immunogenic fragment thereof containing an epitope.

The term "polypeptide" as defined herein encompasses native as well as modified polypeptides. The term "native" as used herein refers to a material recovered from a source in nature as distinct from material artificially modified or altered by man in the laboratory. For example, a native polypeptide is encoded by a gene that is present in the genome of a wild-type organism or cell. By contrast, a modified polypeptide is encoded by a nucleic acid molecule that has been modified in the laboratory so as to differ from the native polypeptide, e.g. by insertion, deletion or substitution of one or more amino acid(s) or any combination of these possibilities. When several modifications are contemplated, they can concern consecutive residues and/or non consecutive residues. Examples of modification(s) contemplated by the present invention may result in alteration of the biological activity exhibited by the native polypeptide. Amino acids that are critical for a given biological activity can be identified by routine methods, such as by structural and functional analysis and one skilled in the art can readily determine the type of mutation(s) that is able to reduce or abolish such a biological activity. Such modifications can be performed by routine techniques such as site-directed mutagenesis. Alternatively, one may generate a synthetic nucleic acid molecule encoding the modified polypeptide by chemical synthesis in automatised process (e.g. assembled from overlapping synthetic oligonucleotides as described in the appended example section).

The term "obtained" as used herein refers to material that is found, isolated, purified, or derived from a source in nature. "Isolated" means removed from its natural environment. "Purified" denotes that it is substantially free from at least one other component(s) with which it is naturally associated. "Derived" denotes one or more modification(s) as compared to the native material (in particular mutations such as substitutions, deletions and/or insertions). Techniques of isolation, purification and modification are routine in the art and depend on the material to be obtained (e.g. cloning of a nucleic acid molecule can be performed from a source in nature by using restriction enzyme, by PCR or by chemical synthesis).

As used herein the term "homology" is generally expressed as a percentage and denotes nucleotide sequences that retain a given degree of identity each other over a portion of at least 40 consecutive nucleotides (e.g. approximately 40, 45, 50, 55, 57, 58, 59, 60, 70 or even more consecutive nucleotides). "At least 80%" refers to approximately 80% or greater than 80% (e.g. any value beyond 80%, advantageously at least 85%, desirably at least 87%, preferably at least 90%, more preferably at least 95%, still more preferably at least 97% up to 100% of sequence homology). "Less than 75%" refers to any value below 75, e.g. approximately 74, 72, 70, 68, 65, 62, 60% or even less. The percent homology between two nucleotide sequences is a function of the number of identical positions shared by the sequences, taking into account the number of gaps which need to be introduced for optimal alignment and the length of each gap. Various computer programs and mathematical algorithms are available in the art to determine percentage identities between nucleotide sequences such as GCG Wisconsin package and the Basic Local alignment Search Tool (BLAST) program which is publicly available at National Center for Biotechnology Information (NCBI) and described in printed publications (e.g. Altschul et al., 1990, J. Mol. Biol. 215, 403-410).

As a starting point, a sequence alignment between the first and second nucleic acid molecules before modification may be used in order to reveal the one or more portions of 40 or more continuous nucleotides that share a percentage of homology of 80% or greater than 80%, i.e. the "homologous" portion(s). In a particular embodiment, the codon usage pattern of the first nucleic acid molecule or the second nucleic acid molecule or both the first and second nucleic acid molecules is modified (e.g. by degenerescence of the codon usage pattern) at least in said homologous portion(s) of 40 or more (e.g. approximately 40, 45, 50, 55, 57, 58, 59, 60, 70 or even more) continuous nucleotides so as to reduce the percentage of homology to less than 75% (e.g. approximately 74, 72, 70, 68, 65, 62, 60% or even less).

Whereas methionine and tryptophane residues are each encoded by a unique nucleic acid triplet (i.e. codon), different codons can be used to code for the 18 other amino acids (degeneracy of the genetic code). For example, amino acids are encoded by codons as follows: Alanine (Ala or A) is encoded by codons GCA, GCC, GCG, and GCU; cysteine (C or Cys) by codons UGC, and UGU; aspartic acid (D or Asp) by codons GAC, and GAU; glutamic acid (E or Glu) by codons GAA, and GAG; phenylalanine (F or Phe) by codons UUC, and UUU; glycine (G or Gly) by codons GGA, GGC, GGG, and GGU; histidine (H or His) by codons CAC, and CAU; isoleucine (I or Ile) by codons AUA, AUC, and AUU; lysine (K or Lys) by codons AAA, and AAG; leucine (L or Leu) by codons UUA, UUG, CUA, CUC, CUG, and CUU; methionine (M or Met) by codon AUG; asparagine (N or Asn) by codons AAC, and AAU; proline (P or Pro) by codons CCA, CCC, CCG, and CCU; glutamine (Q or Gln) by codons CAA, and CAG; arginine (R or Arg) by codons AGA, AGG, CGA, CGC, CGG, and CGU; serine (S or Ser) by codons AGC, AGU, UCA, UCC, UCG, and UCU; threonine (T or Thr) by codons ACA, ACC, ACG, and ACU; valine (V or Val) by codons GUA, GUC, GUG, and GUU; tryptophan (W or Trp) by codon UGG and tyrosine (Y or Tyr) by codons UAC, and UAU.

Reduction of the percentage of homology in the one or more homologous portion(s) present in said first and second nucleic acid molecules can be achieved by taking advantage of the degeneracy of the genetic code and modifying the codon usage pattern in the first nucleic acid molecule and/or the second nucleic acid molecule. Modification of the codon usage pattern is typically performed by replacing one or more "native" codon(s) with another codon(s). For example, the replacement of the Arg-encoding AGA codon with the Arg-encoding CGC codon will reduce homology in 2 of 3 positions of the codon. It is not necessary to degenerate all native codons since homology can be sufficiently reduced with partial replacement. Moreover, modification of the codon usage pattern can be performed over the entire nucleic acid molecule or can be restricted to the homologous portion(s) present before modification. Desirably, in the context of the invention, degenerescence is performed in the first nucleic acid molecule and is restricted to the homologous portion(s). Preferably, the codon usage pattern is modified at the nucleotide level and the modifications are silent at the amino acid level, i.e. when it is possible, each "native" codon is replaced with a codon encoding the same amino acid so that such modifications do not translate in the encoded polypeptide. More preferably, when it is possible, the codon usage pattern is modified in such a way that homologous portions between the first and second nucleic acid molecules are restricted to less than 9 or 8 consecutive nucleotides, advantageously to less than 7 consecutive nucleotides, preferably to less than 6 consecutive nucleotides and, more preferably, to less than 5 consecutive nucleotides. Modification of the codon usage pattern can be generated by a number of ways known to those skilled in the art, such as site-directed mutagenesis (e.g. using the Sculptor™ in vitro mutagenesis system of Amersham, Les Ullis, France), PCR mutagenesis, DNA shuffling and by chemical synthetic techniques (e.g. resulting in a synthetic nucleic acid molecule).

When the vector according to the invention comprises more than two nucleic acid molecules, then any nucleic acid molecule comprised in the vector and obtained from a native nucleic acid sequence which exhibit a percentage of homology of approximately 80% or greater than 80% over a portion of 40 or more continuous nucleotides with at least one other native nucleic acid sequence from which another nucleic acid molecule is obtained, can be modified so as to reduce the percentage of homology to less than 75%, i.e. so that no pair of nucleic acid molecules comprised in the vector may comprise a portion of 40 or more consecutive nucleotides exhibiting a percentage of identity greater than 75%.

A sequence alignment between each (pair of) native sequences from which the nucleic acid molecules are obtained may be used in order to reveal the one or more portions exhibiting a percentage of homology of 80% or greater than 80%. Then, the sequence of one or more of the native sequences is modified, in particular by degenerating the codon usage, so as to reduce the percentage of homology at least in the homologous portions to less than 75%. In the end, no nucleic acid molecule comprised in the vector should comprise a portion of 40 or more (e.g., 45, 50, 55, 57, 58, 59, 60, 70 or even more) consecutive nucleotides exhibiting a percentage of identity greater than 75% with any other nucleic acid molecule comprised in said vector.

As mentioned above, the polypeptide encoded by the nucleic acid molecules comprised in the vector may or not have the same amino acid sequence as the native polypeptide. In particular, in addition to mutations for degenerating the codon usage so as to reduce homology at least in the homologous portions of nucleic acid molecules comprised in the vector, said nucleic acid molecules comprised in the vector may also comprise additional mutations resulting or not in a modification of the amino acid sequence of the encoded polypeptide.

The vector of the invention encompasses viral as well as non-viral (e.g. plasmid DNA) vectors. Suitable non viral vectors include plasmids such as pREP4, pCEP4 (Invitrogene), pCI (Promega), pCDM8 (Seed, 1987, Nature 329, 840), pVAX and pgWiz (Gene Therapy System Inc; Himoudi et al., 2002, J. Viol. 76, 12735-12746). A "viral vector" is used herein according to its art-recognized meaning. It refers to any vector that comprises at least one element of viral origin, including a complete viral genome, a portion thereof or a modified viral genome as described below as well as viral particles generated thereof (e.g. viral vector packaged into a viral capsid to produce infectious viral particles). Viral vectors of the invention can be replication-competent, or can be genetically disabled so as to be replication-defective or replication-impaired. The term "replication-competent" as used herein encompasses replication-selective and conditionally-replicative viral vectors which are engineered to replicate better or selectively in specific host cells (e.g. tumoral cells). Viral vectors may be obtained from a variety of different viruses, and especially from a virus selected from the group consisting of retrovirus, adenovirus, adeno-associated virus (AAV), poxvirus, herpes virus, measle virus and foamy virus.

In one embodiment, the vector of the invention is an adenoviral vector (for a review, see "Adenoviral vectors for gene therapy", 2002, Ed D. Curiel and J. Douglas, Academic Press). It can be derived from any human or animal adenovirus. Any serotype and subgroup can be employed in the context of the invention. One may cite more particularly subgroup A (e.g. serotypes 12, 18, and 31), subgroup B (e.g. serotypes 3, 7, 11, 14, 16, 21, 34, and 35), subgroup C (e.g. serotypes 1, 2, 5, and 6), subgroup D (e.g. serotypes 8, 9, 10, 13, 15, 17, 19, 20, 22-30, 32, 33, 36-39, and 42-47), subgroup E (serotype 4), and subgroup F (serotypes 40 and 41). Particularly preferred are human adenoviruses 2 (Ad2), 5 (Ad5), 6 (Ad6), 11 (Ad11), 24 (Ad24) and 35 (Ad35). Such adenovirus are available from the American Type Culture Collection (ATCC, Rockville, Md.) and have been the subject of numerous publications describing their sequence, organization and methods of producing, allowing the artisan to apply them (see for example U.S. Pat. No. 6,133,028; U.S. Pat. No. 6,110,735; WO 02/40665; WO 00/50573; EP 1016711; Vogels et al., 2003, J. Virol. 77, 8263-8271).

The adenoviral vector of the present invention can be replication-competent. Numerous examples of replication-competent adenoviral vectors are readily available to those skilled in the art (see for example Hernandez-Alcoceba et al., 2000, Human Gene Ther. 11, 2009-2024; Nemunaitis et al., 2001, Gene Ther. 8, 746-759; Alemany et al., 2000, Nature Biotechnology 18, 723-727; WO00/24408; U.S. Pat. No. 5,998,205, WO99/25860, U.S. Pat. No. 5,698,443, WO00/46355, WO00/15820 and WO01/36650).

Alternatively, the adenoviral vector of the invention can be replication-defective (see for example WO94/28152). Preferred replication-defective adenoviral vectors are E1-defective (e.g. U.S. Pat. No. 6,136,594 and U.S. Pat. No. 6,013,638), with an E1 deletion extending from approximately positions 459 to 3328 or from approximately positions 459 to 3510 (by reference to the sequence of the human adenovirus type 5 disclosed in the GeneBank under the accession number M 73260 and in Chroboczek et al., 1992, Virol. 186, 280-285). The cloning capacity and safety can further be improved by deleting additional portion(s) of the adenoviral genome (e.g. in the non essential E3 region or in other essential E2, E4 regions as described in Lusky et al., 1998, J. Virol 72, 2022-2032).

The first and second nucleic acid molecules can be independently inserted in any location of the adenoviral vector of the invention, as described in Chartier et al. (1996, J. Virol. 70, 4805-4810) and independently positioned in sense and/or antisense orientation relative to the natural transcriptional direction of the region of insertion. For example, they can be both inserted in replacement of the E1 region or alternatively, the one is inserted in replacement of the E1 region and the other in replacement of the E3 region.

In another embodiment, the vector of the invention is a poxviral vector (see for example Cox et al. in "Viruses in Human Gene Therapy" Ed J. M. Hos, Carolina Academic Press). It may be obtained from any member of the poxviridae, in particular canarypox (e.g. ALVAC as described in WO95/27780), fowlpox (e.g. TROVAC as described in Paoletti et al., 1995, Dev. Biol. Stand. 84, 159-163) or vaccinia virus, the latter being preferred. A suitable vaccinia virus can be selected from the group consisting of the Copenhagen strain (Goebel et al., 1990, Virol. 179, 247-266 and 517-563; Johnson et al., 1993, Virol. 196, 381-401), the Wyeth strain, NYVAC (see WO92/15672 and Tartaglia et al., 1992, Virology 188, 217-232) and the highly attenuated modified Ankara (MVA) strain (Mayr et al., 1975, Infection 3, 6-16). Such vectors and methods of producing are described in numerous documents accessible to the man skilled in the art (e.g. Paul et al., 2002, Cancer gene Ther. 9, 470-477; Piccini et al., 1987, Methods of Enzymology 153, 545-563; U.S. Pat. No. 4,769,330; U.S. Pat. No. 4,772,848; U.S. Pat. No. 4,603,112; U.S. Pat. No. 5,100,587 and U.S. Pat. No. 5,179,993). The first and second nucleic acid molecules in use in the present invention are preferably inserted in a nonessential locus of the poxviral genome, in order that the recombinant poxvirus remains viable and infectious. Nonessential regions are non-coding intergenic regions or any gene for which inactivation or deletion does not significantly impair viral growth, replication or infection. One may also envisage insertion in an essential viral locus provided that the defective function is supplied in trans during production of viral particles, for example by using an helper cell line carrying the complementing sequences corresponding to those deleted in the poxviral genome.

When using the Copenhagen vaccinia virus, the at least first and second nucleic acid molecules are preferably inserted in the thymidine kinase gene (tk) (Hruby et al., 1983, Proc. Natl. Acad. Sci USA 80, 3411-3415; Weir et al., 1983, J. Virol. 46, 530-537). However, other insertion sites are also appropriate, e.g. in the hemagglutinin gene (Guo et al., 1989, J. Virol. 63, 4189-4198), in the K1L locus, in the u gene (Zhou et al., 1990, J. Gen. Virol. 71, 2185-2190) or at the left end of the vaccinia virus genome where a variety of spontaneous or engineered deletions have been reported in the literature (Altenburger et al., 1989, Archives Virol. 105, 15-27; Moss et al. 1981, J. Virol. 40, 387-395; Panicali et al., 1981, J. Virol. 37, 1000-1010; Perkus et al, 1989, J. Virol. 63, 3829-3836; Perkus et al, 1990, Virol. 179, 276-286; Perkus et al, 1991, Virol. 180, 406-410).

When using MVA, the at least first and second nucleic acid molecules can be independently inserted in anyone of the identified deletions I to VII which occurred in the MVA genome (Antoine et al., 1998, Virology 244, 365-396) as well as in the D4R locus, but insertion in deletion II and/or III is preferred (Meyer et al., 1991, J. Gen. Virol. 72, 1031-1038; Sutter et al., 1994, Vaccine 12, 1032-1040).

When using fowlpox virus, although insertion within the thymidine kinase gene may be considered, the at least first and second nucleic acid molecules are preferably introduced in the intergenic region situated between ORFs 7 and 9 (see for example EP 314 569 and U.S. Pat. No. 5,180,675).

In another embodiment of the invention, the at least first and second nucleic acid molecules independently encode a polypeptide capable of providing a therapeutic or protective activity in a subject exhibiting or susceptible to exhibit a pathological condition. The term "subject" as used herein refers to a vertebrate, particularly a member of the mammalian species and especially domestic animals, farm animals, sport animals, and primates including humans. Such a polypeptide is preferably selected from the group consisting of immunogenic polypeptides and anti-tumor polypeptides.

An "immunogenic" polypeptide refers to a polypeptide able to induce, stimulate, develop or boost an immune system in a subject into which it is expressed. Such immune response can be humoral or cellular or both humoral and cellular. Humoral response elicits antibody production against the polypeptide in question whereas cellular response elicits T-helper cell and/or CTL response and/or stimulation of cytokine production. Typically, the immunogenic property of a polypeptide can be evaluated either in vitro or in vivo by a variety of assays which are standard in the art (for a general description of techniques available to evaluate the onset and activation of an immune response, see for example the latest edition of Coligan et al., Current Protocols in Immunology; ed J Wiley & Sons Inc, National Institute of Health). For example, detection can be colorimetric, fluorometric or radioactive and suitable techniques include ELISA, Western Blot, radioimmunoassays and immunoprecipitation assays. Measurement of cellular immunity can be performed by measurement of cytokine profiles secreted by activated effector cells including those derived from CD4+ and CD8+ T-cells (e.g. quantification IFNg-producing cells by ELIspot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay). The immunogenic property of a polypeptide could also be evaluated in suitable animal models by ELIspot, tetramer-based analytical techniques or other standard techniques for analysis T cell-mediated immunity. Suitable immunogenic polypeptides can be obtained from hepatitis B virus (HBV) (e.g. S, preS2 or preS1-polypeptide as described in EP 414 374; EP 304 578 or EP 198 474); hepatitis C virus (HCV) (e.g. Core (C), the envelop glycoprotein E1, E2, the non-structural polypeptide NS2, NS3, NS4, or NS5 or any combination thereof); human immunodeficiency virus (HIV) (e.g. gp120 or gp160), and papillomavirus (as illustrated hereinafter).

An "anti-tumor" polypeptide refers to a polypeptide able to provide suppression or a net reduction in the expansion of tumor cells. The antitumor property of a polypeptide can be determined in appropriate animal models or in the treated subject by a decrease of the actual tumor size over a period of time. A variety of methods may be used to estimate tumor size including radiologic methods (e.g., single photon and positron emission computerized tomography; see generally, "Nuclear Medicine in Clinical Oncology," Winkler, C. (ed.) Springer-Verlag, New York, 1986), methods employing conventional imaging reagents (e.g., Gallium-67 citrate), immunologic methods (e.g., radiolabeled monoclonal antibody directed to specific tumor markers) as well as ultrasound methods (see, "Ultrasonic Differential Diagnosis of Tumors", Kossoff and Fukuda, (eds.), Igaku-Shoin, New York, 1984). Alternatively, the anti-tumor property of a polypeptide may be determined based upon a decrease in the presence of a tumor marker. Examples include PSA for the detection of prostate cancer and CEA for the detection of colorectal and certain breast cancers. Further, the anti-tumor property of a polypeptide can be determined in a suitable animal model, e.g. using mice injected with a representative human cancer cell line. After palpable tumors have developed, the mice are injected with the vector of the invention, and then monitored for reduced tumor growth rate and increased survival. In addition, a variety of in vitro methods can be used to predict in vivo tumor inhibition. Suitable antitumor polypeptides include tumour-associated antigens (TAAs) such as MUC-1 (WO92/07000; Acres et al., 2005, Exp. Rev. Vaccines 4(4)), BRCA-1, BRCA-2 (Palma et al., 2006, Critical Reviews in Oncology/haematology 27, 1-23), Carcinoembryonic antigen CEA (Conroy et al., 1995, Gene Ther; 2, 59-65), MAGE (WO99/40188; De Plaen et al., 1994, Immunogenetics 40, 360-369), MART-1, gp 100 (Bakker et al., 1994, J. Exp. Med. 179, 1005-9), PRAME, BAGE, Lage (also known as NY Eos 1) SAGE, HAGE (WO99/53061), GAGE (Robbins and Kawakami, 1996. Current Opinions in Immunol. 8, 628-36) and Prostate specific antigen (PSA) (Ferguson, et al., 1999, Proc. Natl. Acad. Sci. USA. 96, 3114-9; WO98/12302, WO98/20117 and WO00/04149) as well as viral polypeptides from viruses having tumor-inducing potential (e.g. papillomavirus).

In another embodiment of the invention, the at least first and second nucleic acid molecules are obtained from the same organism or from closely related organisms.

As used herein, the term "organism" encompasses microorganisms preferably having pathogenic potential and well as higher eukaryotes. The term "microorganism" denotes fungi, bacteria, protozoa and viruses. Representative examples of viruses include without limitation HIV (HIV-1 or HIV-2), human herpes viruses (e.g. HSV1 or HSV2), cytomegalovirus (CMV), Epstein Barr virus (EBV), hepatitis viruses (e.g. hepatitis A virus (HAV), HBV, HCV and hepatitis E virus), flaviviruses (e.g. Yellow Fever Virus), varicella-zoster virus (VZV), paramyxoviruses, respiratory syncytial viruses, parainfluenza viruses, measles virus, influenza viruses, and papillomaviruses (as defined above). Representative examples of suitable bacteria include without limitation *Neisseria* (e.g. *N. gonorrhea* and *N. meningitidis*); *Bordetella* (e.g. *B. pertussis, B. parapertussis* and *B. bronchiseptica*), *Mycobacteria* (e.g. *M. tuberculosis, M. bovis, M. leprae, M. avium, M. paratuberculosis, M. smegmatis*); *Legionella* (e.g. *L. pneumophila*); *Escherichia* (e.g. enterotoxic *E. coli*, enterohemorragic *E. coli*, enteropathogenic *E. coli*); *Shigella* (e.g. *S. sonnei, S. dysenteriae, S. flexnerii*); *Salmonella* (e.g. *S. typhi, S. paratyphi, S. choleraesuis, S. enteritidis*); *Listeria* (e.g. *L. monocytogenes*); *Helicobacter* (e.g. *H. pylori*); *Pseudomonas* (e.g. *P. aeruginosa*); *Staphylococcus* (e.g. *S. aureus, S. epidermidis*); *Enterococcus* (e.g. *E. faecalis, E. faecium*); *Bacillus* (e.g. *B. anthracis*); *Corynebacterium* (e.g. *C. diphtheriae*), and *Chlamydia* (e.g. *C. trachomatis, C. pneumoniae, C. psittaci*). Representative examples of parasites include without limitation *Plasmodium* (e.g. *P. falciparum*); *Toxoplasma* (e.g. *T. gondii*); *Leshmania* (e.g. *L. major*); *Pneumocystis* (e.g. *P. carinii*); and *Schisostoma* (e.g. *S. mansoni*). Representative examples of fungi include without limitation *Candida* (e.g. *C. albicans*) and *Aspergillus*. The higher eukaryotes are preferably mammals including humans.

The "same organism" defines organisms which originate from a common ancestor and have followed the same evolution pathway. Representative examples include various isolates of viruses having the same serotype or genotype. For example two isolates of HPV-16 are classified in this category. "Closely related organisms" define organisms which originate from a common ancestor but have diverged during evolution. Representative examples include viruses having different serotypes or genotypes. For example HPV-16 and HPV-18 are classified in this category.

In a preferred embodiment, the organism for which the at least first and second nucleic acid molecules are obtained is a papillomavirus and each encodes a papillomavirus polypeptide. A "Papillomavirus" can be defined as a virus that belongs to the papillomavirinae subfamily and this term encompasses animal papillomavirus of non-human species origin including but not limited to cattle, horses, rabbits, sheep, dogs, non-human primate, and rodents as well as human papillomavirus (HPV). More than 100 HPV genotypes have been identified at present time (Van Ranst et al., 1992, J. Gen. Virol. 73, 2653; De Villiers et al., 2004, Virology 324, 17-27) which have been classified in "low" (LR) and "high risk" (HR) serotypes depending on their oncogenic potential. LR HPV causes benign tumors in infected subjects whereas HR bears a high risk for malignant progression.

For general guidance, papillomaviruses possess a double-stranded circular DNA of about 7900 base pairs which is surrounded by a protein capsid (see for example Pfister, 1987, in *The papoviridae: The Papillomaviruses*, Salzman and Howley edition, Plenum Press, New York, p 1-38). Their genome consists of three functional regions, the early (E), the late (L), and the long control (LCR) regions. The LCR contains transcriptional regulatory sequences such as enhancers and promoters. The late region encodes the structural L1 and L2 proteins, respectively the major and minor capsid proteins, whereas the early region encodes regulatory proteins (E1-E7) found predominantly in the nucleus that control viral replication, transcription and cellular transformation. More specifically, the E1 protein is a DNA binding phosphoprotein with ATP-dependent helicase activity (Desaintes and Demeret, 1996, Semin. Cancer Biol. 7, 339-347; Wilson et al, 2002, Virus Gene 24, 275-290). The E2 protein is a multifunctional DNA binding phosphoprotein that regulates viral gene transcription and controls DNA replication (Bechtold et al., 2003, J. Virol. 77, 2021-8). The E4-encoded protein binds and disrupts the cytoplasmic keratin network and plays a role in viral maturation. The function for E5 protein is still controversial and its expression is often lost during viral integration in the host chromosomes. The E6 and E7-encoded gene products of HR HPV genotypes are involved in the oncogenic transformation of infected cells (Kanda et al., 1988, J. Virol. 62, 610-3; Vousden et al., 1988, Oncogene Res. 3, 1-9; Bedell et al., 1987, J. Virol. 61, 3635-40), presumably through binding of these viral proteins to cellular tumor suppressor gene products p53 and retinoblastoma (Rb), respectively (reviewed in Howley, 1996, Papillomaviruses and their replication, p 2045-2076. In B. N. Fields, D. M. Knipe and P. M. Howley (ed), Virology, 3$^{rd}$ ed. Lippincott-Raven Press, New York, N.Y.). The amino acid residues involved in the binding of the native HPV-16 E6 polypeptide to p53 have been clearly defined from residues 118 to 122 (+1 being the first Met residue or from residues 111 to 115 starting from the preferably used second Met residue) (Crook et al., 1991, Cell 67, 547-556) and those involved in the binding of the native HPV-16 E7 polypeptide to Rb are located from residues 21 to 26 (Munger et al., 1989, EMBO J. 8, 4099-4105; Heck et al., 1992, Proc. Natl. Acad. Sci. USA 89, 4442-4446).

Preferably, the at least first and second nucleic acid molecules are independently obtained from a high risk papillomavirus selected from the group consisting of HPV-16, HPV-18, HPV-30, HPV-31, HPV-33, HPV-35, HPV-39, HPV-45, HPV-51, HPV-52, HPV-56, HPV-58, HPV-59, HPV-66, HPV-68, HPV-70 and HPV-85.

A "papillomavirus polypeptide" as used herein refers to an art-recognized polypeptide encoded by a nucleic acid molecule obtained from a papillomavirus genome/source. As defined above in connection with the term "polypeptide", a "papillomavirus polypeptide" encompasses native, modified papillomavirus polypeptides and peptides thereof. Sources of papillomavirus include without limitation biological samples (e.g. biological samples, tissue sections, biopsy specimen and tissue cultures collected from a subject that has been exposed to a papillomavirus), cultured cells (e.g. CaSki cells available at ATCC), as well as recombinant materials available in depositary institutions, in commercial catalogues or described in the literature. The nucleotide sequences of a number of papillomavirus genomes and the amino acid sequences of the encoded polypeptides have been described in the literature and are available in specialized data banks, e.g. Genbank. For general information, HPV-16 genome is described in Genbank under accession numbers NC_01526 and K02718; HPV-18 under NC_001357 and X05015; HPV-31 under J04353; HPV-33 under M12732; HPV-35 under NC_001529; HPV-39 under NC_001535; HPV-45 under X74479; HPV-51 under NC_001533; HPV-52 under NC_001592; HPV-56 under X74483; HPV-58 under D90400; HPV-59 under NC_001635; HPV-68 under X67160 and M73258; HPV-70 under U21941; and HPV-85 under AF131950.

The papillomavirus polypeptide(s) encoded by the first and/or the second nucleic acid molecule(s) can be an early, a late or any combination thereof. Early papillomavirus polypeptides include E1, E2, E4, E5, E6 and E7 whereas late polypeptides can be L1 or L2. The nucleotide and amino acid sequences of the early and late polypeptides of a vast number of papillomavirus serotypes are described in the literature available to the skilled person.

Desirably, the at least first and second nucleic acid molecules encode independently an early polypeptide selected from the group consisting of E1, E2, E6 and E7. For purpose of illustration, the amino acid sequences of native HPV-16 E1, E2, E6 and E7 polypeptides are given respectively in SEQ ID NO: 1-4. However, the present invention is not limited to these exemplary sequences. Indeed the nucleotide and amino acid sequences can vary between different papillomavirus isolates and this natural genetic variation is included within the scope of the invention as well as non-natural modification(s) such as those described below. Exemplary illustration of suitable modified papillomavirus polypeptides are given hereinafter (e.g. in SEQ ID NO: 5-8 and 64-65), however, it is within the reach of the skilled person to adapt the modifications described herein (e.g. to polypeptides originating from other papillomavirus genotypes by sequence comparison).

Suitable papillomavirus E1 polypeptides for use in the present invention encompass mutants that are defective for stimulating viral replication, i.e. their ability to stimulate viral replication is statistically significantly lower than that of the corresponding native E1 polypeptide (e.g. less than 75%, advantageously less than 50%, preferably less than 10%, and more preferably less than 5%). For general guidance, the domain responsible for stimulating viral replication is located in the central portion of E1 (e.g. Hugues and Romanos, 1993, Nucleic Acids Res. 21, 5817-23). Representative examples of replication-defective E1 polypeptides are described in the literature available to the man skilled in the art, e.g. in Yasugi et al. (1997, J. Virol 71, 5942-51). A preferred modification in the context of the invention includes the substitution of the Gly residue at position 482 of the HPV-16 E1 polypeptide with another residue (preferably with an Asp residue) (e.g. see SEQ ID NO: 5) or the substitution of the Gly residue at position 489 of HPV-18 E1 polypeptide with another residue (preferably with an Asp residue (e.g., see SEQ ID NO: 6)

Suitable E2 polypeptides for use in the invention encompass mutants that are defective in transcriptional activation and/or replication activities as compared to the native E2 polypeptide (e.g. less than 75%, advantageously less than 50%, preferably less than 10%, and more preferably less than 5%). For general guidance, the domain responsible for transcriptional activation and stimulation of replication is located in the N-terminal portion of E2 (Seedorf et al., 1985, Virology, 145, 181-185; Kennedy et al., 1991, J. Virol. 65, 2093-2097; Cole et al., 1987, J. Mol. Biol. 193, 599-608; McBride et al., 1989, Proc. Natl. Acad. Sci. USA, 86, 510-514) and the reduction or lack of replication and transcriptional E2 activities can be easily determined using standard methods (see for example Sakai et al., 1996, J. Virol. 70, 1602-1611). Suitable defective E2 mutants for use in the present invention are described in the literature available to the man skilled in the art, e.g. in Demeret et al. (1995, Nucleic Acids Res. 23, 4777-4784), Sakai et al. (1996, J. Virol. 70, 1602-1611), Brokaw et al. (1996, J. Virology 70, 23-29) and Ferguson et al. (1996, J. Virology 70, 4193-4199). Preferred modifications in the context of the invention include the substitution of the Glu residue at position 39 of HPV-16 E2 preferably with an Ala residue (E39A) and/or the substitution of the Ile residue at position 73 preferably with an Ala residue (I73A) (e.g. see SEQ ID NO: 7). For purposes of illustration, the Glu and Ile residues at positions 39 and 73 of HPV-16 E2 correspond respectively to the Glu and the Ile residues at positions 43 and 77 of HPV-18 E2 (e.g. see SEQ ID NO: 8).

Suitable E6 polypeptides for use in the invention encompass non-oncogenic mutants that are defective in binding to the cellular tumor suppressor gene product p53. Representative examples of non-oncogenic E6 polypeptides are described e.g. in Pim et al. (1994, Oncogene 9, 1869-1876), and Crook et al. (1991, Cell 67, 547-556). Preferred modifications in this context include the deletion in HPV-16 E6 of residues 118 to 122 (CPEEK) (e.g. see SEQ ID NO: 64) or the deletion in HPV-18 E6 of residues 113 to 117 (NPAEK).

Suitable E7 polypeptides for use in the invention encompass non-oncogenic mutants that are defective in binding to the cellular tumor suppressor gene product Rb. Representative examples of non-oncogenic E7 polypeptides are described, e.g. in Munger et al. (1989, EMBO J. 8, 4099-4105), Heck et al. (1992, Proc. Natl. Acad. Sci. USA 89, 4442-4446) and Phelps et al. (1992, J. Virol. 66, 2148-2427). Preferred modifications in this context include the deletion in HPV-16 E7 of residues 21 to 26 (DLYCYE) (e.g. see SEQ ID NO: 65) or the deletion in HPV-18 E7 of residues 24 to 28 (DLLCH).

Moreover, the polypeptides (e.g. papillomavirus polypeptides) encoded by the at least first and/or second nucleic acid molecules may further comprise additional modifications which are beneficial to the processing, stability and/or solubility of the encoded polypeptides, e.g. suppression of potential cleavage site(s), suppression of potential glycosylation site(s) and/or presentation at the surface of the expressing cells. For example, the encoded polypeptide(s) can include suitable signals for being anchored within the plasma membrane of the expressing cells. Indeed, it has been previously shown that membrane presentation permits to improve MHC class I and/or MHC class II presentation resulting in an enhancement of recognition by the host's immune system (see for example WO99/0388). As native early papillomavirus polypeptides (E1, E2, E6 and E7) are nuclear proteins (although no typical nuclear localization signal could be clearly identified), it could be beneficial to address them at the plasma membrane, in order to improve their immunogenic potential and thus their therapeutic efficacy in the host subject.

Efficient membrane presentation of a polypeptide at the surface of the expressing host cell can be achieved by fusing the polypeptide to a signal peptide and a membrane-anchoring peptide. Such peptides are known in the art. Briefly, signal peptides are generally present at the N-terminus of membrane-presented or secreted polypeptides and initiate their passage into the endoplasmic reticulum (ER). They comprise 15 to 35 essentially hydrophobic amino acids which are then removed by a specific ER-located endopeptidase to give the mature polypeptide. Membrane-anchoring peptides are usually highly hydrophobic in nature and serve to anchor the polypeptides in the cell membrane (see for example Branden and Tooze, 1991, in Introduction to Protein Structure p. 202-214, NY Garland). The choice of the signal and membrane-anchoring peptides which can be used in the context of the present invention is vast. They may be independently obtained from any secreted or membrane-anchored polypeptide (e.g. cellular or viral polypeptides) such as the rabies glycoprotein, the HIV virus envelope glycoprotein or the measles virus F protein or may be synthetic. The preferred site of insertion of the signal peptide is the N-terminus downstream of the codon for initiation of translation and that of the membrane-anchoring peptide is the C-terminus, for example immediately upstream of the stop codon. If necessary, a linker peptide can be used to connect the signal peptide and/or the membrane anchoring peptide to the encoded polypeptide.

Representative examples of membrane-anchored and defective E1 polypeptides suitable for use in the invention are given in SEQ ID NO: 5 (defining the HPV-16 SS-E1*-TMR polypeptide illustrated in the example section) and in SEQ ID NO: 6 (defining the HPV-18 SS-E1*-TMF polypeptide illustrated in the example section). Representative examples of membrane-anchored and defective E2 polypeptides suitable for use in the invention are given in SEQ ID NO: 7 (defining the HPV-16 SS-E2*-TMR polypeptide illustrated in the example section) and in SEQ ID NO: 8 (defining the HPV-18 SS-E2*-TMR polypeptide illustrated in the example section). Representative examples of membrane-anchored and non-oncogenic E6 and E7 polypeptides suitable for use in the invention are given respectively in SEQ ID NO: 64 (defining the HPV-16 SS-E6*-TMF polypeptide illustrated in the example section) and in SEQ ID NO: 65 (defining the HPV-16 SS-E7*-TMR polypeptide illustrated in the example section.

In a particularly preferred embodiment, the at least first nucleic acid molecule and the second nucleic acid molecule encode two different papillomavirus polypeptides obtained from the same HPV serotype.

In a preferred aspect of this embodiment, the first nucleic acid molecule encodes an E1 polypeptide and the second nucleic acid molecule encodes an E2 polypeptide or vice versa. Desirably, the E1 and E2-encoding nucleic acid molecules are obtained from HPV-16 or from HPV-18. Preferably, the first nucleic acid molecule encodes a polypeptide comprising or essentially consisting of, or consisting of the amino acid sequence shown in SEQ ID NO: 5 and the second nucleic acid molecule encodes a polypeptide comprising or essentially consisting of, or consisting of the amino acid sequence shown in SEQ ID NO: 7. Alternatively, the first nucleic acid molecule encodes a polypeptide comprising or essentially consisting of, or consisting of the amino acid sequence shown in SEQ ID NO: 6 and the second nucleic acid molecule encodes a polypeptide comprising or essentially consisting of, or consisting of the amino acid sequence shown in SEQ ID NO: 8.

In the native context (e.g. the HPV-16 or HPV-18 genome), the 3' portion of the E1-encoding sequence overlaps the 5' portion of the E2-encoding sequence over 59 nucleotides. The presence of these 100% homologous 59 nucleotides is expected to negatively influence the stability of a vector expressing both E1 and E2-encoding nucleic acid molecules.

Homologous recombination can occur between these common portions and lead to the loss of the nucleotide sequences comprised between them.

In accordance with the present invention, the 100% homology between the overlapping portion of 59 nucleotides present before modification in E1 and E2-encoding nucleic acid molecules can be reduced to less than 75% by degenerating the codon usage pattern in one of the nucleic acid molecules. A representative example of degenerated sequences is given in SEQ ID NO: 9 in which homology in the E1/E2 overlapping 59 nucleotides is reduced to 69% (as illustrated in FIG. 1) and a preferred vector of the invention encoding HPV-16 E1 and E2 polypeptides comprises the nucleotide sequence shown in SEQ ID NO: 9. The same strategy can be applied to the overlapping portion present in HPV-18 E1 and E2-encoding sequences. Such degenerated sequences can be introduced in the E1-encoding first nucleic acid molecule in replacement of the native overlapping 59 nucleotides (e.g. SEQ ID NO: 10 and 11, respectively).

Accordingly, a preferred vector of the invention comprises a first nucleic acid molecule comprising or essentially consisting of, or consisting of the nucleotide sequence shown in SEQ ID NO: 10 (which encodes the HPV-16 E1 polypeptide of SEQ ID NO: 5) and a second nucleic acid molecule comprising, or essentially consisting of, or consisting of the nucleotide sequence shown in SEQ ID NO: 12 (which encodes the HPV-16 E2 polypeptide of SEQ ID NO: 7). Another preferred vector of the invention comprises a first nucleic acid molecule comprising or essentially consisting of, or consisting of the nucleotide sequence shown in SEQ ID NO: 11 (which encodes the HPV-18 E1 polypeptide of SEQ ID NO: 6) and a second nucleic acid molecule comprising, or essentially consisting of, or consisting of the nucleotide sequence shown in SEQ ID NO: 13 (which encodes the HPV-18 E2 polypeptide of SEQ ID NO: 8). More preferably, the vector of the invention is a MVA vector, the first (E1-encoding) nucleic acid molecule is placed under the control of the vaccinia 7.5K promoter and the second (E2-encoding) nucleic acid molecule under the control of the vaccinia H5R promoter and the first and second nucleic acid molecules are both inserted in deletion III of said MVA vector.

The invention also pertains to a vector comprising a first nucleic acid molecule encoding an HPV-16 E1 polypeptide, a second nucleic acid molecule encoding an HPV-16 E2 polypeptide, a third nucleic acid molecule encoding an HPV-18 E1 polypeptide and a fourth nucleic acid molecule encoding an HPV-18 E2 polypeptide, wherein said first, second, third and fourth nucleic acid molecules do not comprise a portion of 40 or more continuous nucleotides exhibiting a percentage of homology of 75% or greater than 75%. Preferably, said HPV-16 E1 polypeptide comprises the amino acid sequence shown in SEQ ID NO: 5, said HPV-16 E2 polypeptide comprises the amino acid sequence shown in SEQ ID NO: 7, said HPV-18 E1 polypeptide comprises the amino acid sequence shown in SEQ ID NO: 6 and/or said HPV-18 E2 polypeptide comprises the amino acid sequence shown in SEQ ID NO: 8.

In the native context, HPV-16 and HPV-18 E1-encoding sequences comprise several portions of 40 or more continuous nucleotides that exhibit a percentage of homology of 80% or greater than 80%. The same is true with respect to HPV-16 and HPV-18 E2-encoding sequences. Moreover, the adjacent E1 and E2-encoding sequences overlap over a portion of approximately 59 nucleotides in HPV-16 and HPV-18 genomes. In this context, it is advisable to modify the HPV-18 E1 and E2-encoding nucleic acid molecules sequences so as to reduce homology with their HPV-16 counterparts to less than 75% especially in the homologous portions shared by the both serotypes. For this purpose, nucleotide sequences of HPV-16 and HPV-18 E1 and E2 genes can be aligned and modifications can be designed at the nucleotide level so as to reduce homology to less than 8, 7, 6 or preferably 5 consecutive nucleotides. Moreover, HPV-18 E1 sequence can be further modified to reduce homology to less than 75% with the portion of 59 nucleotides overlapping the 5' end of the HPV-18 E2 sequence. Preferably, the codon usage is modified but modifications do not translate at the amino acid level, except for generating modifications as defined herein, e.g. resulting in defective enzymatic functions. Representative examples of "degenerated" HPV-18 E1- and HPV-18 E2-encoding nucleotide sequences that can be suitably used as third and fourth nucleic acid molecules are given in SEQ ID NO: 11 and SEQ ID NO: 13, respectively. A preferred vector of the invention comprises a first nucleic acid molecule comprising, or essentially consisting of or consisting of the nucleotide sequence shown in SEQ ID NO: 10 (encoding the HPV-16 E1 polypeptide shown in SEQ ID NO: 5), a second nucleic acid molecule comprising, or essentially consisting of or consisting of the nucleotide sequence shown in SEQ ID NO: 12 (encoding the HPV-16 E2 polypeptide shown in SEQ ID NO: 7), a third nucleic acid molecule comprising, or essentially consisting of or consisting of the nucleotide sequence shown in SEQ ID NO: 11 (encoding the HPV-18 E1 polypeptide shown in SEQ ID NO: 6) and a fourth nucleic acid molecule comprising, or essentially consisting of or consisting of the nucleotide sequence shown in SEQ ID NO: 13 (encoding the HPV-18 E2 polypeptide shown in SEQ ID NO: 8). Preferably, the vector is a MVA vector, the first, second, third and fourth nucleic acid molecules are introduced in deletion III of the MVA vector, the first and third (E1-encoding) nucleic acid molecules are placed in opposite orientation, each under the control of the vaccinia p7.5K promoter and the second and fourth (E2-encoding) nucleic acid molecules are placed in opposite orientation, each under the control of the vaccinia pH5R promoter.

In another particularly preferred embodiment, the at least first nucleic acid molecule and the second nucleic acid molecule encode the same polypeptide obtained from closely related organisms, e.g. closely related HPV serotypes such as HPV-16, HPV-18, HPV-33 and/or HPV-52.

In a first aspect of this embodiment, the same polypeptide obtained from closely related organisms is preferably an E2 polypeptide. The encoded E2 polypeptides are preferably modified so as to be membrane-anchored and defective for viral replication, as defined herein. In the native context, E2-encoding sequences of various genotypes exhibit a high degree of homology at the nucleotide level, especially in the most conserved portions. The presence of these homologous sequences is expected to negatively influence the stability of a vector co-expressing two or more (e.g. 3, 4 or even more) E2 genes, for example E2 genes from HR HPV such as HPV-16, HPV-18, HPV-33 and HPV-52. Homologous recombination can occur between these homologous gene sequences and lead to the loss of the nucleotide sequences comprised between them, and thus to gene silencing.

In accordance with the present invention, the nucleic acid molecules encoding E2 polypeptides comprised in the vector of the invention can be modified by degenerating the codon usage pattern so as to reduce homology to less than 75% especially in the highly homologous portions. Representative examples of degenerated nucleic acid molecules encoding E2 polypeptides are given in SEQ ID NO: 13, 66, 67, 68 and 69. More specifically, SEQ ID NO: 13 encodes a membrane-presented and replication defective HPV-18 E2 polypeptide which nucleotide sequence has been designed so as to reduce homology with its E2-encoding counterparts to less than 8 or 7 consecutive nucleotides. SEQ ID NO: 66 and 67 both encode a replication-defective HPV-33 E2 polypeptide (it is further membrane-presented in SEQ ID NO: 67) which nucleotide sequences have been designed so as to reduce homology with the other E2-encoding couterparts to less than 8 or 7 consecutive nucleotides. SEQ ID NO: 68 and 69 both encode a replication-defective HPV-52 E2 polypeptide (it is further membrane-presented in SEQ ID NO: 69) which nucleotide sequences have been designed so as to reduce homology with the other E2-encoding counterparts to less than 8 or 7 consecutive nucleotides. However, the present invention is not limited to these exemplary sequences and alternative versions of degenerated nucleic acid molecules encoding E2 papillomavirus polypeptides as defined above can be designed on this principle.

A preferred vector of the invention comprises a first nucleic acid molecule encoding an HPV-16 E2 polypeptide as defined herein (e.g. the membrane-presented and replication-defective E2 polypeptide comprising the amino acid sequence shown in SEQ ID NO: 7), a second nucleic acid molecule encoding an HPV-18 E2 polypeptide as defined herein (e.g. the membrane-presented and replication-defective E2 polypeptide comprising the amino acid sequence shown in SEQ ID NO: 8), a third nucleic acid molecule encoding an HPV-33 E2 polypeptide as defined herein (e.g. the membrane-presented and replication-defective E2 polypeptide comprising the amino acid sequence shown in SEQ ID NO: 70), and a fourth nucleic acid molecule encoding an HPV-52 E2 polypeptide as defined herein (e.g. the membrane-presented and replication-defective E2 polypeptide comprising the amino acid sequence shown in SEQ ID NO: 71). More preferably, the first nucleic acid molecule comprises or essentially consists of the nucleotide sequence shown in SEQ ID NO: 12; the second nucleic acid molecule comprises or essentially consists of the nucleotide sequence shown in SEQ ID NO: 13; the third nucleic acid molecule comprises or essentially consists of the nucleotide sequence shown in SEQ ID NO: 67 and/or the fourth nucleic acid molecule comprises or essentially consists of the nucleotide sequence shown in SEQ ID NO: 69. More preferably, the vector of the invention is a MVA vector and the four E2-encoding nucleic acid molecules are inserted in deletion III. Even more preferably, the first and the second nucleic acid molecules are under the control of the vaccinia H5R promoter and placed in inverted orientation each other whereas the third and fourth nucleic acid molecules are under the control of the vaccinia p7.5K promoter and placed in inverted orientation each other.

In another aspect of this embodiment, the same polypeptide obtained from closely related organisms is preferably an E6 polypeptide, an E7 polypeptide or both E6 and E7 polypeptides. E6 and E7 can be expressed independently or as a fusion polypeptide. The encoded E6 and/or E7 polypeptides are preferably modified so as to be membrane-anchored and non-oncogenic as defined herein.

In the native context HPV-16 and HPV-18 native E6 sequences have 63% of homology at the nucleotide level whereas HPV-16 and HPV-18 native E7 sequences are 57% homologous each other. However, in both cases, the HPV-16 and HPV-18 native sequences share several portions of 40 nucleotides or more that exhibit 80% or greater than 80% of homology (see FIG. 2). The presence of these homologous portions is expected to negatively influence the stability of a vector co-expressing HPV-16 and HPV-18 E6 and/or E7 genes. Homologous recombination can occur between these homologous portions and lead to the loss of the nucleotide sequences comprised between them, and thus to gene silencing.

In accordance with the present invention, the nucleic acid molecules encoding HPV-16 and/or HPV-18 E6 and E7 polypeptides can be modified by degenerating the codon usage pattern so as to reduce homology to less than 75% especially in the homologous portions. A representative example of a degenerated nucleic acid molecule encoding an HPV-18 E6 polypeptide is given in SEQ ID NO: 14 and a representative example of a degenerated modified nucleic acid molecule encoding an HPV-18 E7 polypeptide is given in SEQ ID NO:15. More specifically, SEQ ID NO: 14 and SEQ ID NO: 15 have been designed so as to reduce homology with the HPV-16 counterparts to less than 8, 7, 6 or preferably 5 consecutive nucleotides while encoding HPV-18 membrane-anchored and non-oncogenic E6 and E7 polypeptides. However, alternative versions of degenerated nucleic acid molecules encoding E6 and/or E7 papillomavirus polypeptides as defined above can be designed on this principle.

A preferred vector of the invention comprises a first nucleic acid molecule encoding an HPV-16 E6 polypeptide as defined herein (e.g. membrane-anchored and non oncogenic) and a second nucleic acid molecule encoding an HPV-18 E6 polypeptide as defined herein (e.g. a membrane-anchored non oncogenic), wherein the second nucleic acid molecule comprises or essentially consists of the nucleotide sequence shown in SEQ ID NO: 14. Another preferred vector of the invention comprises a first nucleic acid molecule encoding an HPV-16 E7 polypeptide as defined herein (e.g. membrane-anchored and non oncogenic) and a second nucleic acid molecule encoding an HPV-18 E7 polypeptide as defined herein (e.g. membrane-anchored and non oncogenic), wherein the second nucleic acid molecule comprises or essentially consists of the nucleotide sequence shown in SEQ ID NO: 15. More preferably, the vector of the invention is a MVA vector, the first nucleic acid molecule is placed under the control of the vaccinia 7.5K promoter and the second nucleic acid molecule under the control of the vaccinia H5R promoter and the first and second nucleic acid molecules are both inserted in deletion III of said MVA vector.

The invention also pertains to a vector comprising a first nucleic acid molecule encoding a fusion of an HPV-16 E6 polypeptide with an HPV-16 E7 polypeptide and a second nucleic acid molecule encoding a fusion of an HPV-18 E6 polypeptide with an HPV-18 E7 polypeptide wherein said first and second nucleic acid molecules do not comprise a portion of 40 or more continuous nucleotides exhibiting a percentage of homology of approximately 75% or greater than 75%.

The invention also pertains to a vector comprising a first nucleic acid molecule encoding an HPV-16 E6 polypeptide, a second nucleic acid molecule encoding an HPV-18 E6 polypeptide, a third nucleic acid molecule encoding an HPV-16 E7 polypeptide and a fourth nucleic acid molecule encoding an HPV-18 E7 polypeptide wherein said first, second, third and fourth nucleic acid molecules do not comprise a portion of 40 or more continuous nucleotides exhibiting a percentage of homology of 75% or greater than 75%. Preferably, the second nucleic acid molecule comprises, essentially consists in or consists in SEQ ID NO: 14 and/or the fourth nucleic acid molecule comprises, essentially consists in or consists in SEQ ID NO: 15. More preferably, the vector of the invention is a MVA vector, the first and second nucleic acid molecules are placed in inverted orientation each under the control of the vaccinia 7.5K promoter and the third and fourth nucleic acid molecules in inverted orientation each under the control of the vaccinia H5R promoter and the first, second, third and fourth nucleic acid molecules are inserted in deletion III of said MVA vector.

In another aspect, the present invention also provides a substantially isolated nucleic acid molecule comprising, essentially consisting of or consisting of the nucleotide sequence shown in any SEQ ID NO: 9, 10, 11, 12, 13, 14, 15, 66, 67, 68 or 69.

In another embodiment of the invention, the first and second and if present third and fourth nucleic acid molecules comprised in the vector of the invention are in a form suitable for expression of the encoded polypeptides in a host cell or subject, which means that they are placed under the control of the regulatory sequences necessary to their expression.

As used herein, the term "regulatory sequences" refers to any sequence that allows, contributes or modulates the expression of a nucleic acid molecule in a given host cell, including replication, duplication, transcription, splicing, translation, stability and/or transport of the nucleic acid or one of its derivative (i.e. mRNA) into the host cell. In the context of the present invention, the regulatory sequences are "operably linked" to the nucleic acid molecule to be expressed, i.e. they are placed in a functional relationship which allows for expression in a host cell or subject. Such regulatory sequences are well known in the art (see for example Goeddel, 1990, Gene Expression Technology: Methods in Enzymology 185, Academic Press, San Diego). It will be appreciated by those skilled in the art that the choice of the regulatory sequences can depend on factors such as the vector type, the host cell, the level of expression desired, etc.

The promoter is of special importance and the present invention encompasses the use of constitutive promoters which direct expression of the nucleic acid molecules in many types of host cells and those which direct expression only in certain host cells (e.g., tissue-specific regulatory sequences) or in response to specific events or exogenous factors (e.g. by temperature, nutrient additive, hormone or other ligand). Suitable promoters for constitutive expression in eukaryotic systems include viral promoters, such as SV40 promoter, the cytomegalovirus (CMV) immediate early promoter or enhancer (Boshart et al., 1985, Cell 41, 521-530), the adenovirus early and late promoters, the thymidine kinase (TK) promoter of herpes simplex virus (HSV)-1 and retroviral long-terminal repeats (e.g. MoMuLV and Rous sarcoma virus (RSV) LTRs) as well as cellular promoters such as the phosphoglycero kinase (PGK) promoter (Hitzeman et al., 1983, Science 219, 620-625; Adra et al., 1987, Gene 60, 65-74). Suitable promoters useful to drive expression of the nucleic acid molecules in a poxviral vector include the 7.5K, H5R, TK, p28, p11 or K1L promoters of vaccinia virus. Alternatively, one may use a synthetic promoter such as those described in Chakrabarti et al. (1997, Biotechniques 23, 1094-1097), Hammond et al. (1997, J. Virological Methods 66, 135-138) and Kumar and Boyle (1990, Virology 179, 151-158) as well as chimeric promoters between early and late poxviral promoters.

Inducible promoters are regulated by exogenously supplied compounds, and include, without limitation, the zinc-inducible metallothionein (MT) promoter (Mc Ivor et al., 1987, Mol. Cell Biol. 7, 838-848), the dexamethasone (Dex)-inducible mouse mammary tumor virus (MMTV) promoter, the T7 polymerase promoter system (WO 98/10088), the ecdysone insect promoter (No et al., 1996, Proc. Natl. Acad. Sci. USA 93, 3346-3351), the tetracycline-repressible promoter (Gossen et al., 1992, Proc. Natl. Acad. Sci. USA 89, 5547-5551), the tetracycline-inducible promoter (Kim et al., 1995, J. Virol. 69, 2565-2573), the RU486-inducible promoter (Wang et al., 1997, Nat. Biotech. 15, 239-243 and Wang et al., 1997, Gene Ther. 4, 432-441), the rapamycin-inducible promoter (Magari et al., 1997, J. Clin. Invest. 100, 2865-2872) and the lac, TRP, and TAC promoters from E. coli.

The regulatory sequences in use in the context of the present invention can also be tissue-specific to drive expression of the nucleic acid molecules in specific tissues where therapeutic benefit is desired. Suitable promoters can be taken from genes that are preferentially expressed in tumor cells. Such genes can be identified for example by display and comparative genomic hybridization (see for example U.S. Pat. Nos. 5,759,776 and 5,776,683).

Those skilled in the art will appreciate that the regulatory elements controlling the expression of the nucleic acid molecules comprised in the vector of the invention may further comprise additional elements for proper initiation, regulation and/or termination of transcription (e.g. polyA transcription termination sequences), mRNA transport (e.g. nuclear localization signal sequences), processing (e.g. splicing signals), stability (e.g. introns and non-coding 5' and 3' sequences), and translation (e.g. tripartite leader sequences, ribosome binding sites, Shine-Dalgarno sequences, etc.) into the host cell or subject.

In another aspect, the present invention provides infectious viral particles comprising the above-described vector. No attempts to describe in detail the various methods known for the production of infectious viral particles will be made here. Typically, such viral particles are produced by a process comprising the steps of (a) introducing the viral vector in an appropriate cell line, (b) culturing the cell line under suitable conditions so as to allow the production of said infectious viral particle, recovering the produced infectious viral particle from the culture of said cell line, and optionally purifying said recovered infectious viral particle.

When the viral vector is defective, the infectious particles are usually produced in a complementation cell line or via the use of a helper virus, which supplies in trans the non functional viral genes. For example, suitable cell lines for complementing E1-deleted adenoviral vectors include the 293 cells (Graham et al., 1997, J. Gen. Virol. 36, 59-72), the PER-C6 cells (Fallaux et al., 1998, Human Gene Ther. 9, 1909-1917) and the HER96 cells. Cells appropriate for propagating poxvirus vectors are avian cells, and most preferably primary chicken embryo fibroblasts (CEF) prepared from chicken embryos obtained from fertilized eggs. The producer cells can be cultured in conventional fermentation bioreactors, flasks and Petri plates under appropriate temperature, pH and oxygen content conditions.

The infectious viral particles may be recovered from the culture supernatant or from the cells after lysis. They can be further purified according to standard techniques (chromatography, ultracentrifugation as described for example in WO96/27677, WO98/00524, WO98/22588, WO98/26048, WO00/40702, EP1016700 and WO00/50573).

In another aspect, the present invention provides host cells comprising the above-described nucleic acid molecules, vectors or infectious viral particles. The term "host cell" as used herein defines any cell which can be or has been the recipient of the vector or the infectious viral particle of this invention and progeny of such cells. This term should be understood broadly so as to encompass isolated cells, a group of cells, as well as particular organization of cells, e.g. in tissue or organ. Such cells can be primary, transformed or cultured cells.

Host cells in the context of the invention include prokaryotic cells (e.g. *Escherichia coli, Bacillus, Listeria*), lower eukaryotic cells such as yeast (e.g. *Saccharomyces cerevisiae,*

*Saccharomyces pombe* or *Pichia pastoris*), and other eukaryotic cells such as insect cells, plant and higher eukaryotic cells, with a special preference for mammalian cells (e.g. human or non-human cells). Representative examples of suitable host cells include but are not limited to BHK (baby hamster kidney) cells, MDCK cells (Madin-Darby canine kidney cell line), CRFK cells (Crandell feline kidney cell line), CV-1 cells (African monkey kidney cell line), COS (e.g., COS-7) cells, chinese hamster ovary (CHO) cells, mouse NIH/3T3 cells, HeLa cells and Vero cells. The term "host cell" also encompasses complementing cells capable of complementing at least one defective function of a replication-defective vector of the invention (e.g. adenoviral vector) such as those cited above.

Host cells can be used for producing by recombinant means the polypeptides encoded by the nucleic acid molecules comprised in the vector or infectious particles of the invention. Such techniques are well known in the art (see for example Ausubel, Current Protocols in Molecular Biology, John Wiley, 1987-2002; and the latest edition of Sambrook et al., Molecular Cloning, A Laboratory Manual, Cold Spring Harbor Laboratory Press).

In another aspect, the present invention provides a composition comprising the above-described nucleic acid molecules, vector, infectious viral particle, or host cell (also referred herein to the "active agent") or any combination thereof. Advantageously, the composition is a pharmaceutical composition which comprises a therapeutically effective amount of the active agent(s) and a pharmaceutically acceptable vehicle.

The term "pharmaceutically acceptable vehicle" as used herein is intended to include any and all carriers, solvents, diluents, excipients, adjuvants, dispersion media, coatings, antibacterial and antifungal agents, and absorption delaying agents, and the like, compatible with pharmaceutical administration. As used herein a "therapeutically effective amount" is a dose sufficient for the alleviation of one or more symptoms normally associated with the pathological condition desired to be treated or prevented in a subject. When prophylactic use is concerned, this term means a dose sufficient to prevent or to delay the establishment of a pathological condition in a subject. For example, a therapeutically effective amount could be that amount that is sufficient to induce or enhance an immune response in the treated subject, or that amount that is sufficient to palliate, ameliorate, stabilize, reverse, slow or delay the progression of the pathological condition (e.g. for instance size reduction or regression of a lesion or a tumor in a subject, reversion of a viral infection in an infected subject).

Desirably, the composition of the invention comprises one or more carrier and/or diluent non-toxic at the dosage and concentration employed. Such carrier and/or diluent are preferably selected from those usually employed to formulate compositions in either unit dosage or multi-dose form for systemic or mucosal administration. A suitable carrier can be a solvent, a dispersing medium containing, for example, water, ethanol, polyol (for example, glycerol, propylene glycol, liquid polyethylene glycol, and the like), a vegetable oil or suitable mixtures thereof. The diluent is preferably isotonic, hypotonic or weakly hypertonic and has a relatively low ionic strength. Representative examples of suitable diluents include sterile water, physiological saline (e.g. sodium chloride), Ringer's solution, glucose, trehalose or saccharose solutions, Hank's solution, and other aqueous physiologically balanced salt solutions (see for example the most current edition of Remington: The Science and Practice of Pharmacy, A. Gennaro, Lippincott, Williams&Wilkins). The pH of the composition of the invention is suitably adjusted and buffered in order to be appropriate for use in humans or animals, preferably at a physiological or slightly basic pH (between approximately pH 7.5 to approximately pH 9, with a special preference for a pH of approximately 8 or 8.5). Suitable buffers include phosphate buffer (e.g. PBS), bicarbonate buffer and/or Tris buffer.

The composition of the invention can be in various forms, e.g. frozen, solid (e.g. dry powdered or lyophilized form), or liquid (e.g. aqueous). A solid composition of the active agent plus any additional desired ingredient(s) can be obtained from a previously sterile-filtered solution thereof submitted to vacuum drying and freeze-drying. It can, if desired, be stored in a sterile ampoule ready for reconstitution by the addition of a suitable vehicle before use.

A particularly preferred composition (especially when the active agent is an adenoviral vector) is formulated in 1M saccharose, 150 mM NaCl, 1 mM $MgCl_2$, 54 mg/l Tween 80, 10 mM Tris pH 8.5. Another preferred composition is formulated in 10 mg/ml mannitol, 1 mg/ml HSA, 20 mM Tris, pH 7.2, and 150 mM NaCl. Such formulations are particularly suited for preserving stability of the composition of the invention over a period of at least two months at either freezing (e.g. −70° C., −40° C., −20° C.), or refrigerated (e.g. 4° C.) temperature.

The composition may also contain one or more pharmaceutically acceptable excipients for providing desirable pharmaceutical or pharmacodynamic properties, including for example modifying or maintaining the pH, osmolarity, viscosity, clarity, colour, sterility, stability, release or absorption into an the human or animal subject. Representative examples of stabilizing components include polysorbate 80, L-arginine, polyvinylpyrrolidone, trehalose, and polymers such as polyethylene glycol which may be used to obtain desirable properties of solubility, stability, and half-life (Davis et al., 1978, Enzyme Eng. 4, 169-173; Burnham et al., 1994, Am. J. Hosp. Pharm. 51, 210-218). Viscosity enhancing agents include sodium carboxymethylcellulose, sorbitol, and dextran. The composition can also contain substances known in the art to promote penetration or transport across a mucosal barrier or in a particular organ. For example, a composition suited for vaginal administration can eventually include one or more absorption enhancers useful to increase the pore size of the mucosal membranes.

In addition, the composition of the invention may comprise one or more adjuvant(s) suitable for systemic or mucosal administration in humans. The term "adjuvant" denotes a compound having the ability to enhance the immune response to a particular antigen. The adjuvant can be delivered at or near the site of antigen. Enhancement of humoral immunity is typically manifested by a significant increase (usually greater than 10 fold) in the titer of antibody raised to the antigen. Enhancement of cellular immunity can be measured for example by a positive skin test, cytotoxic T-cell assay, ELIspot assay for IFNg or IL-2. Preferably, the adjuvant in use in the invention is capable of stimulating immunity to the active agent, especially through toll-like receptors (TLR), such as TLR-7, TLR-8 and TLR-9. Representative examples of useful adjuvants include without limitation alum, mineral oil emulsion such as Freunds complete and incomplete (IFA), lipopolysaccharide or a derivative thereof (Ribi et al., 1986, Immunology and Immunopharmacology of Bacterial Endotoxins, Plenum Publ. Corp., NY, p407-19), saponins such as QS21 (Sumino et al., 1998, J. Virol. 72, 4931-9; WO 98/56415), imidazoquinoline compounds such as Imiquimod (Suader, 2000, J. Am Acad Dermatol. 43, S6-S11), 1H-imidazo (4,5-c) quinolon-4-amine derivative (Aldara™) and related compound (Smorlesi, 2005, Gene Ther. 12, 1324-32), cytosine phosphate guanosine oligodeoxynucleotides such as CpG (Chu et al., 1997, J. Exp. Med. 186: 1623; Tritel et al., 2003, J. Immunol. 171: 2358-2547) and cationic peptides such as IC-31 (Kritsch et al., 2005, J. Chromatogr Anal. Technol Biomed Life Sci 822, 263-70).

The nucleic acid molecule, vector, infectious particle or composition of the invention can be administered by a variety of modes of administration, including systemic, topical and mucosal administration. Systemic administration can be performed by any means, e.g. by subcutaneous, intradermal, intramuscular, intravenous, intraperitoneal, intravascular, intraarterial injection. Injections can be made with conventional syringes and needles, or any other appropriate devices available in the art. Mucosal administration can be performed by oral, nasal, intratracheal, intrapulmonary, intravaginal or intra-rectal route. Topical administration can be performed using transdermal means (e.g. patch and the like). Intramuscular or subcutaneous administration is particularly preferred with viral vectors and infectious particles as active agent.

The appropriate dosage may vary depending upon known factors such as the pharmacodynamic characteristics of the particular active agent, age, health, and weight of the subject, the pathological condition(s) to be treated, nature and extent of symptoms, kind of concurrent treatment, frequency of treatment, the need for prevention or therapy and/or the effect desired. The dosage will also be calculated dependent upon the particular route of administration selected. Further refinement of the calculations necessary to determine the appropriate dosage for treatment is routinely made by a practitioner, in the light of the relevant circumstances. For general guidance, suitable dosage for adenovirus particles varies from about $10^5$ to about $10^{13}$ iu (infectious units), desirably from about $10^7$ to about $10^{12}$ iu and preferably from about $10^8$ to about $10^{11}$ iu. Suitable dosage for vaccinia virus particles varies from about $10^4$ to about $10^{10}$ pfu (plaque-forming particle), desirably from about $10^5$ to about $10^9$ pfu and preferably from about $10^6$ to about $5 \times 10^8$ pfu. Vector plasmids can be administered in doses of between 10 µg and 20 mg, and preferably between 100 µg and 2 mg.

Further, the administration may take place in a single dose or, alternatively, in multiple doses according to standard protocols, dosages and regimens over several hours, days and/or weeks. Moreover, the administration can be by bolus injection or continuous infusion. For example, the subject may be treated with at least two (e.g. from 2 to 10) administrations of the above-described nucleic acid molecule, vector, infectious particle or composition. Preferably, a first series of administrations is carried out sequentially within a period of time varying from few days to 4 weeks followed by a second series of administrations (e.g. one or two administrations) carried out within one to 6 months following the latest administration of the first series. The period of time between each of the administrations of the second series can be from few days to 4 weeks. In a preferred embodiment, the first series of administrations comprises three sequential administrations at week interval and the second series comprises one administration within 4 to 6 months following the first series. As a general guidance, with MVA vector, preferred administration route is subcutaneous with a dose of MVA particles comprised between $10^6$ to $5 \times 10^8$ pfu.

The nucleic acid molecule, vector, infectious particle, host cell or composition of the invention may be introduced in a subject for treating or preventing a variety of pathological conditions, including genetic diseases, congenital diseases and acquired diseases. The present invention also pertains to the use of the nucleic acid molecule, vector, infectious particle, host cell or composition of the invention for the preparation of a drug intended for treating or preventing such pathological conditions. It is particularly appropriate for treating or preventing infectious diseases (e.g. viral and/or bacterial infections), cancers and immune deficiency diseases. The term "cancer" as used herein encompasses any cancerous condition which results from unwanted cell proliferation including diffuse or localized tumors, metastasis, cancerous polyps and preneoplastic lesions (e.g. neoplasia).

Infectious diseases which are contemplated in the context of the invention encompass any condition associated with infection by a pathogenic microorganism as described above. Cancers which are contemplated in the context of the invention include without limitation glioblastoma, sarcoma, melanoma, mastocytoma, carcinoma as well as breast cancer, prostate cancer, testicular cancer, ovarian cancer, endometrial cancer, cervical cancer (in particular, those associated with a papillomavirus infection), lung cancer (e.g. including large cell, small cell, squamous and adeno-carcinomas), renal cancer, bladder cancer, liver cancer, colon cancer, anal cancer, pancreatic cancer, stomach cancer, gastrointestinal cancer, cancer of the oral cavity, larynx cancer, brain and CNS cancer, skin cancer (e.g. melanoma and non-melanoma), blood cancer (lymphomas, leukemia, especially if they have developed in solid mass), bone cancer, retinoblastoma and thyroid cancer.

In a preferred embodiment, the invention is used for the preventive or curative treatment of a condition associated with infection by a papillomavirus (especially a HR HPV) such as persistent infection, pre-malignant and malignant lesions. "Persistent infection" refers to the asymptomatic phase of the papillomavirus infection in an infected subject that has not achieved viral eradication. Typically no clinical signs are observed. Examples of pre-malignant lesions include without limitation intraepithelial neoplasia of low, moderate or high grade that can be detected in various tissues such as CIN (cervical intraepithelial neoplasia), vulvar intraepithelial neoplasia (VIN), anal intraepithelial neoplasia (AIN), penile intraepithelial neoplasia (PIN), and vaginal intraepithelial neoplasia (VaIN). Examples of malignant lesions include without limitation cervical carcinoma, anal carcinoma, vaginal cancer, penile cancer and oral cancer. The nucleic acid molecule, vector, infectious particle, host cell or composition of the invention encoding papillomavirus polypeptides is particularly destined for treating pre-malignant, especially CIN2/3 lesions, or malignant lesions, especially cervical carcinoma. In another embodiment, the invention can also be used for the preventive or curative treatment of a condition associated with infection by a hepatitis virus (e.g. HBV or HCV) such as persistent infection, chronic or fulgurant hepatitis and liver cancer.

The active agent can be used alone or, if desired, in conjunction with conventional therapeutic modalities (e.g. radiation, chemotherapy and/or surgery). The conventional therapeutic modalities are delivered in the animal or human subject according to standard protocols using standard agents, dosages and regimens and such modalities may be performed before during and/or after the administration of the active agent(s) of the invention. For example, for treating conditions associated with HCV infection, the method or use of the invention is preferably associated with e.g. protease inhibitors (e.g. serine protease inhibitors such as VX950 of Vertex), polymerase inhibitors, helicase inhibitors, antifibrotics, nucleoside analogs, TLR agonists, siRNA, antisense oligonucleotides, anti-HCV antibodies, immune modulators, therapeutic vaccines and antitumor agents conventionally used in the treatment of HCV-associated hepatocarcinomas (e.g. adriamycin or a mixture of adriamycin lipiodol and spongel usually administered by chimioembolisation in the hepatic artery). A particularly suitable combination includes treatment with pegylated IFN-α (IFN-α2a or IFN-α2b) and/or ribavirin, preferably for 24 to 48 weeks before administration of the active agent(s) of the invention. For treating conditions associated with papillomavirus infection, the method or use of the invention can be associated with ablative procedures, such as loop electrosurgical excision. The method or use according to the invention can also be carried out in conjunction with immunostimulator(s) such as cytokines (e.g. IL-2, IL-7, IL-15, IL-18, IL-21, IFNg) or suicide gene products (e.g. the thymidine kinase of HSV-1 described in Caruso et al., 1993, Proc. Natl. Acad. Sci. USA 90, 7024-28; ECU-1 described in WO 99/54481) or vector(s) expressing such polypeptide(s).

In another embodiment, the method or use of the invention is carried out according to a prime boost therapeutic modality which comprises sequential administrations of primer composition(s) and booster composition(s). Typically, the priming and the boosting compositions use different vehicles which comprise or encode at least an antigenic domain in common. The method or use of the invention may comprise one to ten administrations of the priming composition followed by one to ten administrations of the boosting composition. Desirably, injection intervals are a matter of one day to twelve months. A preferred modality includes three or four sequential administrations of the primer independently separated by a period of time varying from 3 to 10 days (e.g. a week) followed by one or two administration(s) of the booster one to several weeks after the latest primer administration. Moreover, the priming and boosting compositions can be administered at the same site or at alternative sites by the same route or by different routes of administration. For example, compositions based on polypeptide can be administered by a mucosal route whereas compositions based on vectors are preferably injected, e.g. subcutaneous injection for a MVA vector, intramuscular injection for a DNA plasmid and for an adenoviral vector. The vector, infectious particle or composition of the invention can be used to either prime or boost or both prime and boost an immune response in the treated subject. In one embodiment, priming is performed with a plasmid vector of the invention and boosting with a vaccinia virus infectious particle of the invention. In another embodiment, priming is performed with an adenovirus infectious particle of the invention and boosting with a vaccinia virus infectious particle of the invention. In still another embodiment, priming is performed with a vaccinia virus infectious particle of the invention and boosting with an adenovirus infectious particle of the invention.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced in a different way from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF FIGURES

FIG. 1A illustrates the sequence alignment between the 59 nucleotides present (a) at the end of the native HPV-16 E1 sequences (SEQ ID NO:84) and (b) at the beginning of the native HPV-16 E2 sequences (SEQ ID NO:85) and FIG. 1B illustrates the sequence alignment between the 59 nucleotides present (a) at the end of the native HPV-16 E1 sequences (SEQ ID NO:84) or at the beginning of the native HPV-16 E2 sequences and (b) SEQ ID NO:9.

FIG. 2A illustrates the sequence alignment between HPV-16 (SEQ ID NO:86) and HPV-18 (SEQ ID NO:87) E6-encoding sequences and FIG. 2B illustrates the sequence alignment between HPV-16 (SEQ ID NO:86) E6-encoding sequences and SEQ ID NO:14.

The following examples serve to illustrate the present invention.

EXAMPLES

The constructions described below are carried out according to the general genetic engineered and molecular cloning techniques detailed in Maniatis et al. (1989, Laboratory Manual, Cold Spring Harbor Laboratory Press, Cold Spring Harbor N.Y.) or according to the manufacturer's recommendations when a commercial kit is used. PCR amplification techniques are known to the person skilled in the art (see for example PCR protocols—A guide to methods and applications, 1990, published by Innis, Gelfand, Sninsky and White, Academic Press). The recombinant plasmids carrying the ampicillin resistance gene are replicated in the *E. coli* C600 (Stratagene), BJ5183 (Hanahan, 1983, J. Mol. Biol. 166, 557-580) and NM522 on agar or liquid medium supplemented with 100 µg/ml of antibiotic. The constructions of the recombinant vaccinia viruses are performed according to the conventional technology in the field in the documents above cited and in Mackett et al. (1982, Proc. Natl. Acad. Sci. USA 79, 7415-7419) and Mackett et al. (1984, J. Virol. 49, 857-864). The selection gene gpt (xanthine guanine phosphoribosyltransferase) of *E. coli* (Falkner and Moss, 1988, J. Virol. 62, 1849-1854) is used to facilitate the selection of the recombinant vaccinia viruses.

Example 1

Construction of a MVA Vector Expressing HPV-16 E1 and E2 Genes (MVATG17410)

a) Construction of a Recombinant MVA Vector Encoding HPV-16 E2 Gene (MVATG17408)

Cloning of HPV16 E2 Gene

The nucleotide sequences encoding HPV-16 E2 were cloned from the genomic DNA isolated from CaSki cells (ATCC CRL-1550). E2 gene was amplified using primers OTG16809 (SEQ ID NO: 16) and OTG16810 (SEQ ID NO: 17). The resulting fragment was digested by BamHI and EcoRI and inserted in pGEX2T (Amersham Biosciences) restricted by the same enzymes, giving rise to pTG17239. Sequencing of the cloned E2 gene showed five mutations comparing to HPV16 E2 prototype sequence (described in Genbank NC-01526). Two mutations were silent and the three non-silent mutations (T210I, S219P, K310T) were corrected using the QuickChange Site Directed Mutagenesis kit (Stratagene), giving rise to pTG17268.

Modification of the HPV-16 E2 Polypeptide

The E2 nucleotide sequences incorporated in pTG17268 were modified by site directed mutagenesis, in order to generate an HPV-16 E2 variant (E39A and 173A), designated E2*. More specifically, the E2 replication function was abolished by substituting the Glu residue in position 39 with an Ala and the transactivation function by substituting the Ile residue in position 73 with an Ala. The resulting plasmid pTG17318 comprises the modified sequences encoding HPV-16 E2*.

HPV-16 E2* was further modified by fusion at its N-terminus to a peptide signal and at its C-terminus to a membrane-anchoring sequences derived from the glycoprotein of the rabies virus (PG strain; Genbank ay009097) so as to direct presentation of HPV-16 E2* in the expressing host cells at the plasma membrane surface. The nucleotide sequences (SEQ ID NO: 12) encoding the membrane-presented E2 defective variant, designated SS-E2*-TMR, were reassembled by triple PCR using the following primers: OTG17500 (SEQ ID NO: 18), OTG17501 (SEQ ID NO: 19), OTG17502 (SEQ ID NO: 20), OTG17503 (SEQ ID NO: 21), OTG17504 (SEQ ID NO: 22) and OTG17505 (SEQ ID NO: 23). The reassembled sequence was inserted in a pBS-derived vector (Stratagene), to give pTG17360, and then cloned in a vaccinia transfer plasmid downstream the pH5R promoter (Rosel et al, 1986, J Virol. 60, 436-449) resulting in pTG17408.

The transfer plasmid is designed to permit insertion of the nucleotide sequence to be transferred by for homologous recombination in deletion III of the MVA genome. It originates from plasmid pTG1E (described in Braun et al., 2000, Gene Ther. 7, 1447-57) into which were cloned the flanking sequences (BRG3 and BRD3) surrounding the MVA deletion III, which sequences were obtained by PCR from MVATGN33.1 DNA (Sutter and Moss, 1992, Proc. Natl. Acad. Sci. USA 89, 10847-51). The transfer plasmid also contains a fusion between the *Aequorea victoria* enhanced Green Fluorescent protein (eGFP gene, isolated from pEGP-C1, Clontech) and the *Escherichia coli* xanthine-guanine phosphoribosyltransferase gene (gpt gene) under the control of the early late vaccinia virus synthetic promoter p11K7.5 (kindly provided by R. Wittek, University of Lausanne). Synthesis of xanthine-guanine phosphoribosyltransferase enables GPT$^+$ recombinant MVA to form plaques in a selective medium containing mycophenolic acid, xanthine, and hypoxanthine (Falkner et al, 1988, J. Virol. 62, 1849-54) and eGFP enables the visualisation of recombinant MVA plaques. The selection marker eGPP-GPT is placed between two homologous sequences in the same orientation. When the clonal selection is achieved, the selection marker is easily eliminated by several passages without selection allowing the growth of eGPP-GPT recombinant MVA.

Construction of a Recombinant MVA Expressing the HPV-16 SS-E2*-TMR Gene

Generation of MVATG17408 virus was performed by homologous recombination in primary chicken embryos fibroblasts (CEF) infected with MVATGN33.1 (at a MOI of 0.1 pfu/cell) and transfected with pTG17408 (according to the standard calcium phosphate DNA precipitation). Viral selection was performed by three round of plaque purification in the presence of a selective medium containing mycophenolic acid, xanthine and hypoxanthine. As mentioned above, the selection marker was then eliminated by passage in a non-selective medium. Absence of contamination by parental MVA was verified by PCR.

Analysis of E2 expression was performed by Western-blot. CEF were infected at MOI 0.2 with MVATG17408 and after 24 hours, cells were harvested. Western-blot analysis was performed using commercial monoclonal anti-E2 antibody TVG271 (Abcam). Expression of a protein with an apparent molecular weight of 55 kDA was detected, while theoretical molecular weight of E2*-TMR is 48.9 kDa. After treatment of cell extracts with endoglycosydase F, a reduction of the size of the recombinant protein was observed, suggesting that the E2* TMR polypeptide expressed from MVATG17408 is N-glycosyled.

b) Construction of a Recombinant MVA Encoding an HPV-16 E1 Gene Degenerated in the Portion Overlapping with HPV-16 E2 Gene (MVATG17409)

The nucleotide sequences encoding HPV-16 E1 polypeptide were cloned from CaSki cell DNA (ATCC CRL-1550). More specifically, the E1 gene was amplified in two parts E1a (nt 1-1102) and E1b (nt 1001 to 1950). Primers OTG16811 (SEQ ID NO: 24) and OTG 16814 (SEQ ID NO: 25) were used to amplify E1a fragment, which was digested by BamHI and EcoRI and inserted in pGEX2T restricted by the same enzymes, giving rise to pTG17240. E1b fragment was generated using OTG16813 (SEQ ID NO: 26) and OTG16812 (SEQ ID NO: 27) and digested by BamHI and EcoRI before being inserted in pGEX2T, resulting in pTG17241. Sequencing showed 4 mutations comparing to HPV-16 E1 prototype sequence (described in Genbank NC-01526). One mutation was silent and the three non-silent mutations present in E1a (K130Q, N185T and T220S) were corrected by site-directed mutagenesis. The complete E1 gene was then reassembled by cloning the corrected E1a fragment in pTG17241 digested by BsrGI and EcoRI. The resulting plasmid was named pTG17289.

In the HPV-16 genome, the 59 last nucleotides of the E1 gene are identical to the 59 first nucleotides of the E2 gene. In order to avoid problem of instability during production steps of an E1 and E2-encoding MVA vector, this portion of E1-encoding sequences was modified by codon usage modifications so as to decrease the sequence homology with the E2-encoding sequence. The degenerated sequence (SEQ ID NO: 9) was obtained by amplification of the 3' end of E1 gene using degenerated primers OTG17408 (SEQ ID NO: 28) and OTG17409 (SEQ ID NO: 29). The amplified fragment was digested by NsiI and BglII and inserted in pTG17289 restricted by the same enzymes, giving rise to pTG17340.

The HPV-16 degenerated E1 sequences were also mutated by site-directed mutagenesis in order to abolish the replication function of the encoded E1 polypeptide, by substituting the Gly residue in position 482 of HPV-16 E1 with an Asp residue (G482D; also designated herein E1*), resulting in pTG17373.

The HPV-16 E1deg* sequences were also modified so as to direct expression of the encoded polypeptide at the plasma cell surface, by fusion with the signal and the membrane-anchoring peptides derived from the glycoprotein of the rabies virus (ERA isolate; described in Genbank N° M38452). The SS-E1deg*-TMR sequence (SEQ ID NO: 10) was reconstituted by triple PCR using the following primers OTG17560 (SEQ ID NO: 30), OTG17561 (SEQ ID NO: 31), OTG17562 (SEQ ID NO: 32), OTG17563 (SEQ ID NO: 33), OTG17564 (SEQ ID NO: 34) and OTG17565 (SEQ ID NO: 35). The resulting fragment was inserted in a pBS-derived vector (Stratagene), giving pTG17404. The SS-E1deg*-TMR sequence was then cloned in the vaccinia transfer plasmid downstream of the p7.5K promoter (Cochran et al, 1985, J. Virol. 54, 30-7) giving rise to pTG17409.

Generation of MVATG17409 viruses was performed in CEF by homologous recombination as described above.

c) Construction of a Recombinant MVA Encoding HPV-16 E1 and E2 Genes (MVATG17410)

The SS-E1deg*-TMR sequenced controlled by the p7.5K promoter was isolated from pTG17409 and inserted in pTG17408, giving rise to pTG17410.

Generation of MVATG17410 viruses was performed in CEF by homologous recombination as described above.

Example 2

Construction of a MVA Vector Encoding HPV-18 E1 and E2 Genes (MVATG17582)

HPV-18 E1 and E2 genes were reconstituted as synthetic genes and the oligonucleotides were designed so as (i) to reduce the percentage of homology between the homologous portions shared by the native HPV-16 and HPV-18 sequences to less than 75% (Sequences of HPV-16 and HPV-18 E1 and E2 genes were aligned and oligonucleotides were designed so as to reduce homology to less than 5 consecutive nucleotides) (ii) to reduce homology to less than 75% between the portion of 59 nucleotides present both in the 3' end of the native HPV-18 E1 sequence and in the 5' end of the HPV-18 E2 sequence and (ii) to introduce the mutations abolishing the enzymatic functions of the HPV-18 E1 and E2 gene product (E1: G489D, E2: E43A and 177A).

HPV-18 degE1* sequence was reconstituted by assembling 50 oligonucleotides and cloned in a pBS vector giving rise to pTG17473. The E1 sequence was then fused to the signalling sequences clones from measles virus F protein (SS-18E1deg*-TMF) by a triple PCR using primers OTG15315 (SEQ ID NO: 36), OTG17881 (SEQ ID NO: 37), OTG17882 (SEQ ID NO: 38), OTG17883 (SEQ ID NO: 39), OTG17884 (SEQ ID NO: 40) and OTG17885 (SEQ ID NO: 41). The resulting fragment (SEQ ID NO: 11) was cloned in a MVA transfer vector under the control of p7.5K promoter, to generate pTG17521.

HPV-18 degE2* sequence was reconstituted by assembling 26 oligonucleotides and cloned in a pBS vector, giving rise to pTG17498. The fusion with the signal and the membrane-anchoring peptides of the glycoprotein of the rabies virus (ERA strain; Genbank n° M38452) was performed by triple PCR using primers OTG17875 (SEQ ID NO: 42), OTG17876 (SEQ ID NO: 43), OTG17877 (SEQ ID NO: 44), OTG17878 (SEQ ID NO: 45), OTG17879 (SEQ ID NO: 46) and OTG17880 (SEQ ID NO: 47). The SS-18E2*-TMR cassette was inserted in the MVA transfer plasmid downstream the pH5R promoter, giving rise to pTG17552. Finally, the p7.5K-SS-E1deg*-TMF cassette was isolated from pTG17521 and inserted in pTG17552, giving rise to pTG17582.

Generation of recombinant MVATG17521, MVATG17552 and MVATG17582 was performed as described above.

Example 3

Construction of a Multivalent MVA Vector Expressing HPV-16 and HPV-18 E1 and E2 Genes (MVATG17583)

The p7.5K-SS-18E1deg*-TMF cassette and the pH5R-SS-18E2*-TMR cassette were introduced in pTG17410 (containing the p7.5K-SS-16E1deg*-TMR cassette and the pH5R-SS-16E2*-TMR) and the resulting transfer plasmid was named pTG17583. Generation of MVATG17583 was performed as described above.

Example 4

Construction of a Multivalent Recombinant Virus Expressing HPV16 and HPV18 E6 and E7 Genes MVATG16327 is a recombinant MVA virus expressing membrane anchored and non-oncogenic variants of HPV-16 and HPV-18 E6 and E7 polypeptides. The E6 and E7 nucleotide sequences were mutated in order to eliminate their oncogenic properties (E6* and E7*) and were fused to sequences encoding appropriate signal and membrane anchoring peptides (E6*tm, E7*tm). More specifically, HPV-18 E7* was fused respectively at its N- and C-termini with the signal and membrane-anchoring peptides of the F glycoprotein of the measle virus whereas HPV-16 E6*, HPV-16 E7* and HPV-18 E6* with signal and membrane-anchoring peptides derived from those of the rabies virus glycoprotein. Moreover, HPV-18 E6 and E7 nucleotide sequences were further modified by codon usage modification so as to decrease homology with their HPV16 counterparts. For this purpose, sequences of native HPV16 and HPV18 genes were aligned and codon degeneration was performed to reduce homology to less than 5 consecutive nucleotides. In the vector, the HPV-16 and HPV-18 E6 sequences are both placed under the control of the p7.5K promoter in opposite orientation each other whereas the HPV-16 and HPV-18 E7 sequences are driven by the H5R promoter and all expression cassettes are inserted into the region of excision III of the MVA genome.

a) Construction of the HPV-16 E7*tm Expression Cassette

The HPV-16 E7 gene was isolated from Caski cells and modified so as to encode a non-oncogenic and membrane-presented E7 polypeptide (16E7*tmR) as described in WO99/03885. Non-oncogenic mutations were performed by deletion of amino acid residues 21-26 ($\Delta$DLYCYE) and membrane presentation by fusion of the E7* mutated sequence respectively at its 5' end 3' ends to sequences encoding the signal and membrane-anchoring peptides cloned from the rabies virus glycoprotein (ERA Strain; Genbank accession number M38452). The resulting sequence was cloned under the control of the early-late pH5R promoter (Rosel et al, 1986. J. Virol. 60, 436-9) and the cassette was introduced in a pBS derived vector, giving rise to pTG16161.

b) Cloning of HPV-16 E6*tm and HPV-18 E6*tm Expression Cassettes

The HPV-16 E6 gene was isolated and modified so as to encode a non-oncogenic and membrane-presented E6 polypeptide as described in WO99/03885. Non-oncogenic mutations were performed by deletion of amino acid residues 118-122 ($\Delta$CPEEK) and membrane presentation by fusion of the E6*-mutated sequence respectively at its 5' end 3' ends to sequences encoding the signal and membrane-anchoring peptides derived from the rabies virus glycoprotein (PG strain; Genbank accession number ay009097). This was performed by inserting the E6*-mutated sequence in a vector containing the signal peptide and the membrane-anchoring peptide sequence separated by a BamHI site, leading to pTG16097.

A synthetic HPV-18 E6 sequence was generated by assembling oligonucleotides OTG15174 (SEQ ID NO: 48), OTG15175 (SEQ ID NO: 49), OTG15176 (SEQ ID NO: 50), OTG15177 (SEQ ID NO: 51), OTG15178 (SEQ ID NO: 52), OTG15179 (SEQ ID NO: 53), OTG15180 (SEQ ID NO: 54) and OTG15181 (SEQ ID NO: 55). The oligonucleotides were designed so as to introduce deletion of codons encoding amino acid residues 113-117 (non-oncogenic mutation $\Delta$NPAEK) and to degenerate codon usage in order to reduce homology with the HPV-16 E6 gene (degenerated sequence). The resulting synthetic sequence was then fused respectively at its 5' and 3' end with the sequences encoding signal and membrane-anchoring peptides derived from the rabies virus glycoprotein gene, to provide the sequence shown in SEQ ID NO: 14, leading to pTG16160. The HPV-16 E6*tmR and HPV-18 degE6*tmR sequences were inserted in opposite orientation, each under the control of the p7.5K promoter. The cassettes were then introduced in pTG16161 to generate pTG16215.

c) Cloning of HPV-18 E7*tmF Expression Cassette

A synthetic HPV-18 E7 sequence was generated by assembling oligonucleotides OTG14773 (SEQ ID NO: 56), OTG14774 (SEQ ID NO: 57), OTG14775 (SEQ ID NO: 58), OTG14776 (SEQ ID NO: 59), OTG14777 (SEQ ID NO: 60) and OTG14778 (SEQ ID NO: 61). The oligonucleotides were designed so as to introduce deletion of codons encoding amino acid residues 24-28 (non-oncogenic mutation ΔDLLCH) and to degenerate codon usage in order to reduce homology with the HPV-16 E7 gene (degenerated sequence). The resulting synthetic sequence was then fused at its 5' and 3' ends respectively with the coding sequences for signal and membrane-anchoring peptides cloned from F protein gene of measles virus (described in EP 0305229). The resulting sequence (SEQ ID NO: 15) was cloned under the control of the pH5R promoter and the cassette was introduced in a pBS derived-vector to generate pTG16015.

d) Construction of Transfer Plasmid pTG16327

The transfer plasmid pTG6019 (described in Example 2 of WO99/03885) contains homologous sequences flanking MVA deletion III. It was modified as follow. A synthetic polylinker, obtained by hybridation of primers OTG15040 (SEQ ID NO: 62) and OTG15041 (SEQ ID NO: 63), was introduced in pTG6019 digested by BamHI and SacI, giving rise to pTG16007. A SacI-SacI fragment containing the expression cassette coding for *E. coli* gpt placed under the control of the early-late pH5R promoter was isolated from pTG14033 (described in Example 2 of EP 1 146 125) and introduced in pTG16007 digested by SacI, giving rise to pTG16093. Synthesis of xanthine-guanine phosphoribosyltransferase enables GPT+ recombinant MVA to form plaques in a selective medium containing mycophenolic acid, xanthine, and hypoxanthine (Falkner et al, 1988. J. Virol. 62, 1849-54). The selection marker GPT is placed between two homologous sequences in the same orientation. When the clonal selection is achieved, the selection marker is easily eliminated by several passages without selection allowing the growth of GPT recombinant MVA.

A HindIII-SmaI fragment containing the HPV-18 degE7*TMF expression cassette was isolated from pTG16015 and introduced in pTG16093 digested by the same enzymes, giving rise to pTG16105. On the other hand, pTG16215 was digested by SalI and EcoRI, treated by T4 DNa polymerase, and the resulting fragment containing HPV-16 E7*tmR, HPV-16 E6*tmR and HPV-18 degE6*TMR expression cassettes was introduced in pTG16105 digested by SmaI, leading to pTG16327 (FIG. 2).

e) Generation of MVATG16327

Generation of MVATG16327 was performed by homologous recombination in primary chicken embryos fibroblasts (CEF). For this purpose, pTG16327 was transfected according to the standard calcium phosphate DNA precipitation onto CEF previously infected with MVATGN33.1 at a MOI of 0.1 pfu/cell. Viral selection was performed by three round of plaque purification on CEF in the presence of a selective medium containing mycophenolic acid, xanthine and hypoxanthine. The selection marker was then eliminated by passage in non-selective medium. Absence of contamination by parental MVA was verified by PCR.

Analysis of gene expression was performed by Westernblot. CEF were infected at MOI 0.2 with MVATG16327 and after 24 hours, cells were harvested. Western-blot analysis was performed using rabbit polyclonal antibodies against HPV-16 and HPV-18 E6 and E7 proteins, respectively. The results show that all HPV polypeptides were correctly expressed from MVATG16327.

f) Study of Genetic Stability of MVATG16327

Five passages of MVATG16327 were done on CEF infected at an MOI of $10^{-2}$ pfu/cell and $10^{-4}$ pfu/cell. Genetic stability was evaluated on 100 viral clones isolated from the $5^{th}$ passage of the research stock. Two methods were used: PCR amplification to determine the structure of the expression cassettes, and antigens detection by Western Blot. Results of the PCR analysis showed that 99% of the clones contained the expression cassettes of interest. Immuno-detection showed that 97% of the clones expressed the four antigens: HPV-16 and HPV-18 E6*tm and E7*tm polypeptides.

These analyses showed that 97% of clones derived from MVATG16327 were conformed after five passages, indicating a good genetic stability of this construct.

Example 5

Construction of a Multivalent MVA Vector Expressing HPV-16, HPV-18, HPV-33 and HPV-52 E2 Genes A synthetic gene encoding HPV-33 E2 polypeptide was synthetized by Geneart (Regensburg, Germany). The synthetic sequence was designed so as (i) to reduce the percentage of homology to less than 75% with E2 genes from HPV-16, HPV-18 and HPV-52 (if possible homologous portions are reduced to less than 6 consecutive nucleotides) and (ii) to introduce the mutations abolishing the enzymatic functions of the HPV-33 gene product (E39A and I73A).

The HPV-33 degE2* sequence was then fused with nucleotide sequence encoding the signal and the membrane-anchoring peptides of the glycoprotein of the rabies virus (ERA strain, Genbank n° M38452). This was performed by triple PCR using primers OTG18962 (SEQ ID NO: 72), OTG18963 (SEQ ID NO: 73), OTG18964 (SEQ ID NO: 74), OTG18965 (SEQ ID NO: 75), OTG18966 (SEQ ID NO: 76) and OTG18967 (SEQ ID NO: 77). The resulting fragment (SEQ ID NO: 67) encoding the SS-33degE2*-TMR polypeptide was cloned in a MVA transfer vector under the control of p7.5K promoter, and virus particles were generated as described above.

A synthetic gene encoding HPV-52 E2 polypeptide was synthetized by Geneart (Regensburg, Germany). The synthetic sequence was designed so as (i) to reduce the percentage of homology to less than 75% with E2 genes from HPV-16, HPV-18 and HPV-33 (homologous portions are preferably reduced to less than 6 consecutive nucleotides) and (ii) to introduce the mutations abolishing the enzymatic functions of the HPV-52 gene product (E39A and I73A).

The synthetic HPV-52 E2*deg sequence was then fused with nucleotide sequences encoding the signal and the membrane-anchoring peptides of the measles virus F protein (giving SS-52E2*deg-TMF) by a triple PCR using primers OTG18968 (SEQ ID NO: 78), OTG18969 (SEQ ID NO: 79), OTG18970 (SEQ ID NO: 80), OTG18971 (SEQ ID NO: 81), OTG18972 (SEQ ID NO: 82) and OTG18973 (SEQ ID NO: 83).

The resulting fragment (SEQ ID NO: 69) encoding the SS-52E2*-deg-TMF polypeptide was inserted in a MVA transfer plasmid downstream the p7.5K promoter, and virus particles were generated as described above.

The pH5R-SS-18E2*-TMR cassette encoding the membrane-presented and enzymatically defective HPV-18 E2 polypeptide (isolated from pTG17552), the p7.5K-SS-33degE2*-TMR cassette encoding the membrane-presented and enzymatically defective HPV-33 E2 polypeptide and the p7.5K-SS-52degE2*-TMF cassette encoding the membrane-presented and enzymatically defective HPV-52 E2 polypeptide were introduced in pTG17408 (containing the pH5R-SS-16E2*-TMR cassette), and virus particles were generated as described above.

The invention claimed is:

1. A vector comprising at least a first nucleic acid molecule encoding a first polypeptide and a second nucleic acid molecule encoding a second polypeptide wherein:
   said first and second nucleic acid molecules are obtained respectively from a first and second native nucleic acid sequences which exhibit a percentage of homology of approximately 80% or greater than 80% over a portion of 40 or more continuous nucleotides;
   said first nucleic acid molecule and/or said second nucleic acid molecule are modified so as to reduce the percentage of homology to less than 75%;
   said first nucleic acid molecule and said second nucleic acid molecule encode at least the same polypeptide obtained from closely related HPV serotypes; and
wherein the codon usage pattern is modified in such a way that homologous portions between the first and second nucleic acid molecules are restricted to less than 8 consecutive nucleotides and
wherein said closely related HPV serotypes are selected from the group consisting of HPV-16, HPV-18, HPV-33, and HPV-52.

2. The vector according to claim 1, wherein the codon usage pattern of the first nucleic acid molecule and/or the second nucleic acid molecule is modified at least in said homologous portion(s) of 40 or more continuous nucleotides so as to reduce the percentage of homology to less than 75%.

3. The vector according to claim 2, wherein the codon usage pattern is modified at the nucleotide level and said modifications are silent at the amino acid level.

4. The vector according to claim 1, wherein the codon usage pattern is modified in such a way that homologous portions between the first and second nucleic acid molecules are restricted to less than 5 consecutive nucleotides.

5. The vector according to claim 1, wherein said vector is an adenoviral vector.

6. The vector according to claim 5, wherein said adenoviral vector is replication-defective.

7. The vector according to claim 1, wherein said vector is a poxviral vector.

8. The vector according to claim 7, wherein said poxviral vector is obtained from a vaccinia virus selected from the group consisting of the Copenhagen strain, the Wyeth strain, NYVAC and the highly attenuated modified Ankara (MVA) strain.

9. The vector according to claim 1, wherein the first and second nucleic acid molecules encode an early papillomavirus polypeptide selected from the group consisting of E1, E2, E6 and E7.

10. The vector according to claim 1, wherein said same polypeptide obtained from closely related HPV serotypes is an E2 polypeptide.

11. The vector according to claim 1, wherein said vector comprises a first nucleic acid molecule encoding an HPV-16 E2 polypeptide, a second nucleic acid molecule encoding an HPV-18 E2 polypeptide, a third nucleic acid molecule encoding an HPV-33 E2 polypeptide, and a fourth nucleic acid molecule encoding an HPV-52 E2 polypeptide.

12. The vector according to claim 11, wherein said HPV-16 E2 polypeptide comprises the amino acid sequence shown in SEQ ID NO:7, said HPV-18 E2 polypeptide comprises the amino acid sequence shown in SEQ ID NO:8, said HPV-33 E2 polypeptide comprises the amino acid sequence shown in SEQ ID NO:70 and said HPV-52 E2 polypeptide comprises the amino acid sequence shown in SEQ ID NO:71.

13. The vector according to claim 11, wherein said first nucleic acid molecule comprises the nucleotide sequence shown in SEQ ID NO:12; said second nucleic acid molecule comprises the nucleotide sequence shown in SEQ ID NO:13; said third nucleic acid molecule comprises the nucleotide sequence shown in SEQ ID NO:67 and said fourth nucleic acid molecule comprises the nucleotide sequence shown in SEQ ID NO:69.

14. The vector according to claim 1, wherein said same polypeptide obtained from closely related HPV serotypes is an E6 polypeptide, an E7 polypeptide, or both E6 and E7 polypeptides.

15. The vector according to claim 14, wherein the first nucleic acid molecule encodes an HPV-16 E6 polypeptide and the second nucleic acid molecule encodes an HPV-18 E6 polypeptide, and wherein the second nucleic acid molecule comprises the nucleotide sequence shown in SEQ ID NO:14.

16. The vector according to claim 14, wherein the first nucleic acid molecule encodes an HPV-16 E7 polypeptide and the second nucleic acid molecule encodes an HPV-18 E7 polypeptide, and wherein the second nucleic acid molecule comprises the nucleotide sequence shown in SEQ ID NO:15.

17. The vector according to claim 15, wherein said vector is a MVA vector, the first nucleic acid molecule is placed under the control of the vaccinia 7.5K promoter, the second nucleic acid molecule is placed under the control of the vaccinia H5R promoter, and the first and second nucleic acid molecules are both inserted in deletion III of said MVA vector.

18. The vector according to claim 14, wherein said vector comprises a first nucleic acid molecule encoding an HPV-16 E6 polypeptide, a second nucleic acid molecule encoding an HPV-18 E6 polypeptide, a third nucleic acid molecule encoding an HPV-16 E7 polypeptide and a fourth nucleic acid molecule encoding an HPV-18 E7 polypeptide wherein said first, second, third and fourth nucleic acid molecules do not comprise a portion of 40 or more continuous nucleotides exhibiting a percentage of homology of 75% or greater than 75%.

19. An isolated host cell comprising the vector according to claim 1.

20. A pharmaceutical composition comprising a therapeutically effective amount of the vector according to claim 1 and a pharmaceutically acceptable vehicle.

21. The pharmaceutical composition of claim 20, wherein said composition comprises one or more adjuvant suitable for systemic or mucosal administration in humans.

22. The pharmaceutical composition of claim 21, wherein said adjuvant is an imidazoquinoline compound.

23. A method for treating or preventing infectious disease or cancer, comprising administering an effective amount of the vector of claim 1 to a subject in need thereof.

24. The method according to claim 23, wherein the infectious disease comprises infection by a papillomavirus.

25. The method according to claim 23, wherein the method is carried out according to a prime boost therapeutic modality and wherein said vector is used to prime and/or boost an immune response in a subject.

26. The vector according to claim 1, wherein at least one of said first and second nucleic acid molecules is selected from SEQ ID NOs 10, 11, 12, 13, 14, 15, 66, 67, 68, and 69.

* * * * *

```
                         SEQUENCE LISTING

<160> NUMBER OF SEQ ID NOS: 87

<210> SEQ ID NO 1
<211> LENGTH: 649
<212> TYPE: PRT
<213> ORGANISM: Human papillomavirus type 16

<400> SEQUENCE: 1

Met Ala Asp Pro Ala Gly Thr Asn Gly Glu Glu Gly Thr Gly Cys Asn
1               5                   10                  15

Gly Trp Phe Tyr Val Glu Ala Val Val Glu Lys Lys Thr Gly Asp Ala
            20                  25                  30

Ile Ser Asp Asp Glu Asn Glu Asn Asp Ser Asp Thr Gly Glu Asp Leu
        35                  40                  45

Val Asp Phe Ile Val Asn Asp Asn Asp Tyr Leu Thr Gln Ala Glu Thr
    50                  55                  60

Glu Thr Ala His Ala Leu Phe Thr Ala Gln Glu Ala Lys Gln His Arg
65                  70                  75                  80

Asp Ala Val Gln Val Leu Lys Arg Lys Tyr Leu Gly Ser Pro Leu Ser
                85                  90                  95

Asp Ile Ser Gly Cys Val Asp Asn Asn Ile Ser Pro Arg Leu Lys Ala
            100                 105                 110

Ile Cys Ile Glu Lys Gln Ser Arg Ala Ala Lys Arg Arg Leu Phe Glu
        115                 120                 125

Ser Glu Asp Ser Gly Tyr Gly Asn Thr Glu Val Glu Thr Gln Gln Met
    130                 135                 140

Leu Gln Val Glu Gly Arg His Glu Thr Glu Thr Pro Cys Ser Gln Tyr
145                 150                 155                 160

Ser Gly Gly Ser Gly Gly Gly Cys Ser Gln Tyr Ser Ser Gly Ser Gly
                165                 170                 175

Gly Glu Gly Val Ser Glu Arg His Thr Ile Cys Gln Thr Pro Leu Thr
            180                 185                 190

Asn Ile Leu Asn Val Leu Lys Thr Ser Asn Ala Lys Ala Ala Met Leu
        195                 200                 205

Ala Lys Phe Lys Glu Leu Tyr Gly Val Ser Phe Ser Glu Leu Val Arg
    210                 215                 220

Pro Phe Lys Ser Asn Lys Ser Thr Cys Cys Asp Trp Cys Ile Ala Ala
225                 230                 235                 240

Phe Gly Leu Thr Pro Ser Ile Ala Asp Ser Ile Lys Thr Leu Leu Gln
                245                 250                 255

Gln Tyr Cys Leu Tyr Leu His Ile Gln Ser Leu Ala Cys Ser Trp Gly
            260                 265                 270

Met Val Val Leu Leu Leu Val Arg Tyr Lys Cys Gly Lys Asn Arg Glu
        275                 280                 285

Thr Ile Glu Lys Leu Leu Ser Lys Leu Leu Cys Val Ser Pro Met Cys
    290                 295                 300

Met Met Ile Glu Pro Pro Lys Leu Arg Ser Thr Ala Ala Ala Leu Tyr
305                 310                 315                 320

Trp Tyr Lys Thr Gly Ile Ser Asn Ile Ser Glu Val Tyr Gly Asp Thr
                325                 330                 335
```

-continued

```
Pro Glu Trp Ile Gln Arg Gln Thr Val Leu Gln His Ser Phe Asn Asp
            340                 345                 350

Cys Thr Phe Glu Leu Ser Gln Met Val Gln Trp Ala Tyr Asp Asn Asp
            355                 360                 365

Ile Val Asp Asp Ser Glu Ile Ala Tyr Lys Tyr Ala Gln Leu Ala Asp
            370                 375                 380

Thr Asn Ser Asn Ala Ser Ala Phe Leu Lys Ser Asn Ser Gln Ala Lys
385                 390                 395                 400

Ile Val Lys Asp Cys Ala Thr Met Cys Arg His Tyr Lys Arg Ala Glu
                405                 410                 415

Lys Lys Gln Met Ser Met Ser Gln Trp Ile Lys Tyr Arg Cys Asp Arg
                420                 425                 430

Val Asp Asp Gly Gly Asp Trp Lys Gln Ile Val Met Phe Leu Arg Tyr
            435                 440                 445

Gln Gly Val Glu Phe Met Ser Phe Leu Thr Ala Leu Lys Arg Phe Leu
        450                 455                 460

Gln Gly Ile Pro Lys Lys Asn Cys Ile Leu Leu Tyr Gly Ala Ala Asn
465                 470                 475                 480

Thr Gly Lys Ser Leu Phe Gly Met Ser Leu Met Lys Phe Leu Gln Gly
                485                 490                 495

Ser Val Ile Cys Phe Val Asn Ser Lys Ser His Phe Trp Leu Gln Pro
            500                 505                 510

Leu Ala Asp Ala Lys Ile Gly Met Leu Asp Asp Ala Thr Val Pro Cys
            515                 520                 525

Trp Asn Tyr Ile Asp Asp Asn Leu Arg Asn Ala Leu Asp Gly Asn Leu
            530                 535                 540

Val Ser Met Asp Val Lys His Arg Pro Leu Val Gln Leu Lys Cys Pro
545                 550                 555                 560

Pro Leu Leu Ile Thr Ser Asn Ile Asn Ala Gly Thr Asp Ser Arg Trp
                565                 570                 575

Pro Tyr Leu His Asn Arg Leu Val Val Phe Thr Phe Pro Asn Glu Phe
            580                 585                 590

Pro Phe Asp Glu Asn Gly Asn Pro Val Tyr Glu Leu Asn Asp Lys Asn
            595                 600                 605

Trp Lys Ser Phe Phe Ser Arg Thr Trp Ser Arg Leu Ser Leu His Glu
            610                 615                 620

Asp Glu Asp Lys Glu Asn Asp Gly Asp Ser Leu Pro Thr Phe Lys Cys
625                 630                 635                 640

Val Ser Gly Gln Asn Thr Asn Thr Leu
                645

<210> SEQ ID NO 2
<211> LENGTH: 365
<212> TYPE: PRT
<213> ORGANISM: Human papillomavirus type 16

<400> SEQUENCE: 2

Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
                20                  25                  30

Trp Lys His Met Arg Leu Glu Cys Ala Ile Tyr Tyr Lys Ala Arg Glu
            35                  40                  45

Met Gly Phe Lys His Ile Asn His Gln Val Val Pro Thr Leu Ala Val
        50                  55                  60
```

```
Ser Lys Asn Lys Ala Leu Gln Ala Ile Glu Leu Gln Leu Thr Leu Glu
 65                  70                  75                  80

Thr Ile Tyr Asn Ser Gln Tyr Ser Asn Glu Lys Trp Thr Leu Gln Asp
                 85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
    290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
        355                 360                 365

<210> SEQ ID NO 3
<211> LENGTH: 158
<212> TYPE: PRT
<213> ORGANISM: Human papillomavirus type 16

<400> SEQUENCE: 3

Met His Gln Lys Arg Thr Ala Met Phe Gln Asp Pro Gln Glu Arg Pro
 1               5                  10                  15

Arg Lys Leu Pro Gln Leu Cys Thr Glu Leu Gln Thr Thr Ile His Asp
                 20                  25                  30

Ile Ile Leu Glu Cys Val Tyr Cys Lys Gln Gln Leu Leu Arg Arg Glu
             35                  40                  45

Val Tyr Asp Phe Ala Phe Arg Asp Leu Cys Ile Val Tyr Arg Asp Gly
         50                  55                  60

Asn Pro Tyr Ala Val Cys Asp Lys Cys Leu Lys Phe Tyr Ser Lys Ile
 65                  70                  75                  80
```

```
Ser Glu Tyr Arg His Tyr Cys Tyr Ser Leu Tyr Gly Thr Thr Leu Glu
            85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
        130                 135                 140

Ser Cys Cys Arg Ser Ser Arg Thr Arg Arg Glu Thr Gln Leu
145                 150                 155

<210> SEQ ID NO 4
<211> LENGTH: 98
<212> TYPE: PRT
<213> ORGANISM: Human papillomavirus type 16

<400> SEQUENCE: 4

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 5
<211> LENGTH: 737
<212> TYPE: PRT
<213> ORGANISM: artificial sequence
<220> FEATURE:
<223> OTHER INFORMATION: HPV-16 membrane-presented and replication-
      defective E1 polypeptide

<400> SEQUENCE: 5

Met Val Pro Gln Ala Leu Leu Phe Val Pro Leu Leu Val Phe Pro Leu
1               5                   10                  15

Cys Phe Gly Lys Phe Pro Ile Ala Asp Pro Ala Gly Thr Asn Gly Glu
            20                  25                  30

Glu Gly Thr Gly Cys Asn Gly Trp Phe Tyr Val Glu Ala Val Val Glu
        35                  40                  45

Lys Lys Thr Gly Asp Ala Ile Ser Asp Asp Glu Asn Glu Asn Asp Ser
    50                  55                  60

Asp Thr Gly Glu Asp Leu Val Asp Phe Ile Val Asn Asp Asn Asp Tyr
65                  70                  75                  80

Leu Thr Gln Ala Glu Thr Glu Thr Ala His Ala Leu Phe Thr Ala Gln
                85                  90                  95

Glu Ala Lys Gln His Arg Asp Ala Val Gln Val Leu Lys Arg Lys Tyr
            100                 105                 110

Leu Gly Ser Pro Leu Ser Asp Ile Ser Gly Cys Val Asp Asn Asn Ile
        115                 120                 125

Ser Pro Arg Leu Lys Ala Ile Cys Ile Glu Lys Gln Ser Arg Ala Ala
        130                 135                 140
```

-continued

```
Lys Arg Arg Leu Phe Glu Ser Glu Asp Ser Gly Tyr Gly Asn Thr Glu
145                 150                 155                 160

Val Glu Thr Gln Gln Met Leu Gln Val Glu Gly Arg His Glu Thr Glu
            165                 170                 175

Thr Pro Cys Ser Gln Tyr Ser Gly Gly Ser Gly Gly Cys Ser Gln
        180                 185                 190

Tyr Ser Ser Gly Ser Gly Gly Glu Gly Val Ser Glu Arg His Thr Ile
            195                 200                 205

Cys Gln Thr Pro Leu Thr Asn Ile Leu Asn Val Leu Lys Thr Ser Asn
    210                 215                 220

Ala Lys Ala Ala Met Leu Ala Lys Phe Lys Glu Leu Tyr Gly Val Ser
225                 230                 235                 240

Phe Ser Glu Leu Val Arg Pro Phe Lys Ser Asn Lys Ser Thr Cys Cys
                245                 250                 255

Asp Trp Cys Ile Ala Ala Phe Gly Leu Thr Pro Ser Ile Ala Asp Ser
            260                 265                 270

Ile Lys Thr Leu Leu Gln Gln Tyr Cys Leu Tyr Leu His Ile Gln Ser
    275                 280                 285

Leu Ala Cys Ser Trp Gly Met Val Val Leu Leu Val Arg Tyr Lys
290                 295                 300

Cys Gly Lys Asn Arg Glu Thr Ile Glu Lys Leu Leu Ser Lys Leu Leu
305                 310                 315                 320

Cys Val Ser Pro Met Cys Met Met Ile Glu Pro Pro Lys Leu Arg Ser
                325                 330                 335

Thr Ala Ala Ala Leu Tyr Trp Tyr Lys Thr Gly Ile Ser Asn Ile Ser
            340                 345                 350

Glu Val Tyr Gly Asp Thr Pro Glu Trp Ile Gln Arg Gln Thr Val Leu
            355                 360                 365

Gln His Ser Phe Asn Asp Cys Thr Phe Glu Leu Ser Gln Met Val Gln
    370                 375                 380

Trp Ala Tyr Asp Asn Asp Ile Val Asp Asp Ser Glu Ile Ala Tyr Lys
385                 390                 395                 400

Tyr Ala Gln Leu Ala Asp Thr Asn Ser Asn Ala Ser Ala Phe Leu Lys
                405                 410                 415

Ser Asn Ser Gln Ala Lys Ile Val Lys Asp Cys Ala Thr Met Cys Arg
            420                 425                 430

His Tyr Lys Arg Ala Glu Lys Lys Gln Met Ser Met Ser Gln Trp Ile
    435                 440                 445

Lys Tyr Arg Cys Asp Arg Val Asp Asp Gly Gly Asp Trp Lys Gln Ile
    450                 455                 460

Val Met Phe Leu Arg Tyr Gln Gly Val Glu Phe Met Ser Phe Leu Thr
465                 470                 475                 480

Ala Leu Lys Arg Phe Leu Gln Gly Ile Pro Lys Lys Asn Cys Ile Leu
                485                 490                 495

Leu Tyr Gly Ala Ala Asn Thr Asp Lys Ser Leu Phe Gly Met Ser Leu
            500                 505                 510

Met Lys Phe Leu Gln Gly Ser Val Ile Cys Phe Val Asn Ser Lys Ser
    515                 520                 525

His Phe Trp Leu Gln Pro Leu Asp Ala Lys Ile Gly Met Leu Asp
    530                 535                 540

Asp Ala Thr Val Pro Cys Trp Asn Tyr Ile Asp Asp Asn Leu Arg Asn
545                 550                 555                 560

Ala Leu Asp Gly Asn Leu Val Ser Met Asp Val Lys His Arg Pro Leu
```

```
                565                 570                 575
Val Gln Leu Lys Cys Pro Pro Leu Leu Ile Thr Ser Asn Ile Asn Ala
            580                 585                 590

Gly Thr Asp Ser Arg Trp Pro Tyr Leu His Asn Arg Leu Val Val Phe
            595                 600                 605

Thr Phe Pro Asn Glu Phe Pro Phe Asp Glu Asn Gly Asn Pro Val Tyr
            610                 615                 620

Glu Leu Asn Asp Lys Asn Trp Lys Ser Phe Phe Ser Arg Thr Trp Ser
625                 630                 635                 640

Arg Leu Ser Leu His Glu Asp Glu Asp Lys Glu Asn Asp Gly Asp Ser
            645                 650                 655

Leu Pro Thr Phe Lys Cys Val Ser Gly Gln Asn Thr Asn Thr Leu Tyr
            660                 665                 670

Val Leu Leu Ser Ala Gly Thr Leu Ile Ala Leu Met Leu Ile Ile Phe
            675                 680                 685

Leu Ile Thr Cys Cys Lys Arg Val Asp Arg Pro Glu Ser Thr Gln Arg
            690                 695                 700

Ser Leu Arg Gly Thr Gly Arg Asn Val Ser Val Thr Ser Gln Ser Gly
705                 710                 715                 720

Lys Phe Ile Ser Ser Trp Glu Ser His Lys Ser Gly Gly Glu Thr Arg
                    725                 730                 735

Leu

<210> SEQ ID NO 6
<211> LENGTH: 746
<212> TYPE: PRT
<213> ORGANISM: artificial sequence
<220> FEATURE:
<223> OTHER INFORMATION: HPV-18 membrane-anchored and replication-
      defective E1 polypeptide

<400> SEQUENCE: 6

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Ala Asp Pro Glu
            20                  25                  30

Gly Thr Asp Gly Glu Gly Thr Gly Cys Asn Gly Trp Phe Tyr Val Gln
        35                  40                  45

Ala Ile Val Asp Lys Lys Thr Gly Asp Val Ile Ser Asp Asp Glu Asp
    50                  55                  60

Glu Asn Ala Thr Asp Thr Gly Ser Asp Met Val Asp Phe Ile Asp Thr
65                  70                  75                  80

Gln Gly Thr Phe Cys Glu Gln Ala Glu Leu Glu Thr Ala Gln Ala Leu
                85                  90                  95

Phe His Ala Gln Glu Val His Asn Asp Ala Gln Val Leu His Val Leu
            100                 105                 110

Lys Arg Lys Phe Ala Gly Gly Ser Thr Glu Asn Ser Pro Leu Gly Glu
        115                 120                 125

Arg Leu Glu Val Asp Thr Glu Leu Ser Pro Arg Leu Gln Glu Ile Ser
    130                 135                 140

Leu Asn Ser Gly Gln Lys Lys Ala Lys Arg Arg Leu Phe Thr Ile Ser
145                 150                 155                 160

Asp Ser Gly Tyr Gly Cys Ser Glu Val Glu Ala Thr Gln Ile Gln Val
                165                 170                 175

Thr Thr Asn Gly Glu His Gly Gly Asn Val Cys Ser Gly Gly Ser Thr
            180                 185                 190
```

```
Glu Ala Ile Asp Asn Gly Gly Thr Glu Gly Asn Asn Ser Ser Val Asp
            195                 200                 205

Gly Thr Ser Asp Asn Ser Asn Ile Glu Asn Val Asn Pro Gln Cys Thr
        210                 215                 220

Ile Ala Gln Leu Lys Asp Leu Leu Lys Val Asn Asn Lys Gln Gly Ala
225                 230                 235                 240

Met Leu Ala Val Phe Lys Asp Thr Tyr Gly Leu Ser Phe Thr Asp Leu
                245                 250                 255

Val Arg Asn Phe Lys Ser Asp Lys Thr Thr Cys Thr Asp Trp Val Thr
                260                 265                 270

Ala Ile Phe Gly Val Asn Pro Thr Ile Ala Glu Gly Phe Lys Thr Leu
            275                 280                 285

Ile Gln Pro Phe Ile Leu Tyr Ala His Ile Gln Cys Leu Asp Cys Lys
        290                 295                 300

Trp Gly Val Leu Ile Leu Ala Leu Leu Arg Tyr Lys Cys Gly Lys Ser
305                 310                 315                 320

Arg Leu Thr Val Ala Lys Gly Leu Ser Thr Leu His Val Pro Glu
                325                 330                 335

Thr Cys Met Leu Ile Gln Pro Pro Lys Leu Arg Ser Ser Val Ala Ala
                340                 345                 350

Leu Tyr Trp Tyr Arg Thr Gly Ile Ser Asn Ile Ser Glu Val Met Gly
            355                 360                 365

Asp Thr Pro Glu Trp Ile Gln Arg Leu Thr Ile Gln His Gly Ile
        370                 375                 380

Asp Asp Ser Asn Phe Asp Leu Ser Glu Met Val Gln Trp Ala Phe Asp
385                 390                 395                 400

Asn Glu Leu Thr Asp Glu Ser Asp Met Ala Phe Glu Tyr Ala Leu Leu
                405                 410                 415

Ala Asp Ser Asn Ser Asn Ala Ala Phe Leu Lys Ser Asn Cys Gln
                420                 425                 430

Ala Lys Tyr Leu Lys Asp Cys Ala Thr Met Cys Lys His Tyr Arg Arg
            435                 440                 445

Ala Gln Lys Arg Gln Met Asn Met Ser Gln Trp Ile Arg Phe Arg Cys
        450                 455                 460

Ser Lys Ile Asp Glu Gly Gly Asp Trp Arg Pro Ile Val Gln Phe Leu
465                 470                 475                 480

Arg Tyr Gln Gln Ile Glu Phe Ile Thr Phe Leu Gly Ala Leu Lys Ser
                485                 490                 495

Phe Leu Lys Gly Thr Pro Lys Lys Asn Cys Leu Val Phe Cys Gly Pro
                500                 505                 510

Ala Asn Thr Asp Lys Ser Tyr Phe Gly Met Ser Phe Ile His Phe Ile
            515                 520                 525

Gln Gly Ala Val Ile Ser Phe Val Asn Ser Thr Ser His Phe Trp Leu
        530                 535                 540

Glu Pro Leu Thr Asp Thr Lys Val Ala Met Leu Asp Asp Ala Thr Thr
545                 550                 555                 560

Thr Cys Trp Thr Tyr Phe Asp Thr Tyr Met Arg Asn Ala Leu Asp Gly
                565                 570                 575

Asn Pro Ile Ser Ile Asp Arg Lys His Lys Pro Leu Ile Gln Leu Lys
                580                 585                 590

Cys Pro Pro Ile Leu Leu Thr Thr Asn Ile His Pro Ala Lys Asp Asn
            595                 600                 605

Arg Trp Pro Tyr Leu Glu Ser Arg Ile Thr Val Phe Glu Phe Pro Asn
```

```
                610                 615                 620
Ala Phe Pro Phe Asp Lys Asn Gly Asn Pro Val Tyr Glu Ile Asn Asp
625                 630                 635                 640

Lys Asn Trp Lys Cys Phe Phe Glu Arg Thr Trp Ser Arg Leu Asp Leu
                645                 650                 655

His Glu Glu Glu Asp Ala Asp Thr Glu Gly Asn Pro Phe Gly Thr
                660                 665                 670

Phe Lys Leu Arg Ala Gly Gln Asn His Arg Pro Leu Gly Leu Ser Ser
                675                 680                 685

Thr Ser Ile Val Tyr Ile Leu Ile Ala Val Cys Leu Gly Gly Leu Ile
                690                 695                 700

Gly Ile Pro Ala Leu Ile Cys Cys Cys Arg Gly Arg Cys Asn Lys Lys
705                 710                 715                 720

Gly Glu Gln Val Gly Met Ser Arg Pro Gly Leu Lys Pro Asp Leu Thr
                725                 730                 735

Gly Thr Ser Lys Ser Tyr Val Arg Ser Leu
                740                 745

<210> SEQ ID NO 7
<211> LENGTH: 453
<212> TYPE: PRT
<213> ORGANISM: artificial sequence
<220> FEATURE:
<223> OTHER INFORMATION: HPV-16 membrane-anchored and replication-
      defective E2 polypeptide

<400> SEQUENCE: 7

Met Val Pro Leu Ala Leu Leu Val Pro Leu Leu Gly Phe Ser Leu
1               5                   10                  15

Cys Phe Gly Lys Phe Pro Ile Glu Thr Leu Cys Gln Arg Leu Asn Val
                20                  25                  30

Cys Gln Asp Lys Ile Leu Thr His Tyr Glu Asn Asp Ser Thr Asp Leu
                35                  40                  45

Arg Asp His Ile Asp Tyr Trp Lys His Met Arg Leu Ala Cys Ala Ile
50                  55                  60

Tyr Tyr Lys Ala Arg Glu Met Gly Phe Lys His Ile Asn His Gln Val
65                  70                  75                  80

Val Pro Thr Leu Ala Val Ser Lys Asn Lys Ala Leu Gln Ala Ala Glu
                85                  90                  95

Leu Gln Leu Thr Leu Glu Thr Ile Tyr Asn Ser Gln Tyr Ser Asn Glu
                100                 105                 110

Lys Trp Thr Leu Gln Asp Val Ser Leu Glu Val Tyr Leu Thr Ala Pro
                115                 120                 125

Thr Gly Cys Ile Lys Lys His Gly Tyr Thr Val Glu Val Gln Phe Asp
                130                 135                 140

Gly Asp Ile Cys Asn Thr Met His Tyr Thr Asn Trp Thr His Ile Tyr
145                 150                 155                 160

Ile Cys Glu Glu Ala Ser Val Thr Val Val Glu Gly Gln Val Asp Tyr
                165                 170                 175

Tyr Gly Leu Tyr Tyr Val His Glu Gly Ile Arg Thr Tyr Phe Val Gln
                180                 185                 190

Phe Lys Asp Asp Ala Glu Lys Tyr Ser Lys Asn Lys Val Trp Glu Val
                195                 200                 205

His Ala Gly Gly Gln Val Ile Leu Cys Pro Thr Ser Val Phe Ser Ser
                210                 215                 220

Asn Glu Val Ser Ser Pro Glu Ile Ile Arg Gln His Leu Ala Asn His
```

```
                225                 230                 235                 240
Pro Ala Ala Thr His Thr Lys Ala Val Ala Leu Gly Thr Glu Glu Thr
                    245                 250                 255

Gln Thr Thr Ile Gln Arg Pro Arg Ser Glu Pro Asp Thr Gly Asn Pro
                260                 265                 270

Cys His Thr Thr Lys Leu Leu His Arg Asp Ser Val Asp Ser Ala Pro
            275                 280                 285

Ile Leu Thr Ala Phe Asn Ser Ser His Lys Gly Arg Ile Asn Cys Asn
        290                 295                 300

Ser Asn Thr Thr Pro Ile Val His Leu Lys Gly Asp Ala Asn Thr Leu
305                 310                 315                 320

Lys Cys Leu Arg Tyr Arg Phe Lys Lys His Cys Thr Leu Tyr Thr Ala
                325                 330                 335

Val Ser Ser Thr Trp His Trp Thr Gly His Asn Val Lys His Lys Ser
                340                 345                 350

Ala Ile Val Thr Leu Thr Tyr Asp Ser Glu Trp Gln Arg Asp Gln Phe
            355                 360                 365

Leu Ser Gln Val Lys Ile Pro Lys Thr Ile Thr Val Ser Thr Gly Phe
        370                 375                 380

Met Ser Ile Tyr Val Leu Leu Ser Ala Gly Thr Leu Ile Ala Leu Met
385                 390                 395                 400

Leu Ile Ile Phe Leu Ile Thr Cys Cys Lys Arg Val Asp Arg Pro Glu
                405                 410                 415

Ser Thr Gln Arg Ser Leu Arg Gly Thr Gly Arg Asn Val Ser Val Thr
                420                 425                 430

Ser Gln Ser Gly Lys Phe Ile His Ser Trp Glu Ser Tyr Lys Ser Gly
            435                 440                 445

Gly Glu Thr Gly Leu
        450

<210> SEQ ID NO 8
<211> LENGTH: 453
<212> TYPE: PRT
<213> ORGANISM: artificial sequence
<220> FEATURE:
<223> OTHER INFORMATION: HPV-18 membrane-anchored and replication-
      defective E2 polypeptide

<400> SEQUENCE: 8

Met Val Pro Gln Ala Leu Leu Phe Val Pro Leu Leu Val Phe Pro Leu
1               5                   10                  15

Cys Phe Gly Lys Phe Pro Ile Gln Thr Pro Lys Glu Thr Leu Ser Glu
                20                  25                  30

Arg Leu Ser Cys Val Gln Asp Lys Ile Ile Asp His Tyr Glu Asn Asp
            35                  40                  45

Ser Lys Asp Ile Asp Ser Gln Ile Gln Tyr Trp Gln Leu Ile Arg Trp
        50                  55                  60

Ala Asn Ala Ile Phe Phe Ala Ala Arg Glu His Gly Ile Gln Thr Leu
65                  70                  75                  80

Asn His Gln Val Val Pro Ala Tyr Asn Ile Ser Lys Ser Lys Ala His
                85                  90                  95

Lys Ala Ala Glu Leu Gln Met Ala Leu Gln Gly Leu Ala Gln Ser Arg
                100                 105                 110

Tyr Lys Thr Glu Asp Trp Thr Leu Gln Asp Thr Cys Glu Glu Leu Trp
            115                 120                 125

Asn Thr Glu Pro Thr His Cys Phe Lys Lys Gly Gly Gln Thr Val Gln
```

```
                130                 135                 140
Val Tyr Phe Asp Gly Asn Lys Asp Asn Cys Met Thr Tyr Val Ala Trp
145                 150                 155                 160

Asp Ser Val Tyr Tyr Met Thr Asp Ala Gly Thr Trp Asp Lys Thr Ala
                165                 170                 175

Thr Cys Val Ser His Arg Gly Leu Tyr Tyr Val Lys Glu Gly Tyr Asn
                180                 185                 190

Thr Phe Tyr Ile Glu Phe Lys Ser Glu Cys Lys Tyr Gly Asn Thr
                195                 200                 205

Gly Thr Trp Glu Val His Phe Gly Asn Asn Val Ile Asp Cys Asn Asp
                210                 215                 220

Ser Met Cys Ser Thr Ser Asp Asp Thr Val Ser Ala Thr Gln Leu Val
225                 230                 235                 240

Lys Gln Leu Gln His Thr Pro Ser Pro Tyr Ser Ser Thr Val Ser Val
                245                 250                 255

Gly Thr Ala Lys Thr Tyr Gly Gln Thr Ser Ala Ala Thr Arg Pro Gly
                260                 265                 270

His Cys Gly Leu Ala Glu Lys Gln His Cys Gly Pro Val Asn Pro Leu
                275                 280                 285

Leu Gly Ala Ala Thr Pro Thr Gly Asn Asn Lys Arg Arg Lys Leu Cys
                290                 295                 300

Ser Gly Asn Thr Thr Pro Ile Ile His Leu Lys Gly Asp Arg Asn Ser
305                 310                 315                 320

Leu Lys Cys Leu Arg Tyr Arg Leu Arg Lys His Ser Asp His Tyr Arg
                325                 330                 335

Asp Ile Ser Ser Thr Trp His Trp Thr Gly Ala Gly Asn Glu Lys Thr
                340                 345                 350

Gly Ile Leu Thr Val Thr Tyr His Ser Glu Thr Gln Arg Thr Lys Phe
                355                 360                 365

Leu Asn Thr Val Ala Ile Pro Asp Ser Val Gln Ile Leu Val Gly Tyr
                370                 375                 380

Met Thr Met Tyr Val Leu Leu Ser Ala Gly Ala Leu Thr Ala Leu Met
385                 390                 395                 400

Leu Ile Ile Phe Leu Met Thr Cys Cys Arg Arg Val Asn Arg Ser Glu
                405                 410                 415

Pro Thr Gln His Asn Leu Arg Gly Thr Gly Arg Glu Val Ser Val Thr
                420                 425                 430

Pro Gln Ser Gly Lys Ile Ile Ser Ser Trp Glu Ser His Lys Ser Gly
                435                 440                 445

Gly Glu Thr Arg Leu
    450

<210> SEQ ID NO 9
<211> LENGTH: 59
<212> TYPE: DNA
<213> ORGANISM: artificial sequence
<220> FEATURE:
<223> OTHER INFORMATION: portion of 59 nucleotides of HPV-16 E1-encoding
      sequences degenerated to decrease homology with the overlapping
      portion in HPV-16 E2-encoding  sequences

<400> SEQUENCE: 9
atggtgattc attacctaca ttcaagtgcg tatctggtca gaacacaaat actttgtga      59

<210> SEQ ID NO 10
<211> LENGTH: 2214
<212> TYPE: DNA
```

<213> ORGANISM: artificial sequence
<220> FEATURE:
<223> OTHER INFORMATION: Nucleotide sequence encoding a membrane-
anchored and replication-defective HPV-16 E1 polypeptide
degenerated in the 59 nucleotides portion overlapping with the
native HPV-16 E2-encoding sequence.

<400> SEQUENCE: 10

```
atggtaccgc aagccctgct attcgtacct ttattggtct ttccctctg tttcggtaag      60
tttcctatag ctgatcctgc aggtaccaat ggggaagagg gtacgggatg taatggatgg    120
ttttatgtag aggctgtagt ggaaaaaaaa acagggatg ctatatcaga tgacgagaac    180
gaaaatgaca gtgatacagg tgaagatttg gtagatttta tagtaaatga taatgattat    240
ttaacacagg cagaaacaga dacagcacat gcgttgttta ctgcacagga agcaaaacaa    300
catagagatg cagtacaggt tctaaaacga aagtatttgg gtagtccact tagtgatatt    360
agtggatgtg tagacaataa tattagtcct agattaaaag ctatatgtat agaaaaacaa    420
agtagagctg caaaaaggag attatttgaa agcgaagaca cgggtatgg caatactgaa    480
gtggaaactc agcagatgtt acaggtagaa gggcgccatg agactgaaac accatgtagt    540
cagtatagtg gtgaagtgg gggtggttgc agtcagtaca gtagtggaag tggggagag    600
ggtgttagtg aaagacacac tatatgccaa acaccactta caaatatttt aaatgtacta    660
aaaactagta atgcaaggc agcaatgtta gcaaaattta agagttata cggggtgagt    720
ttttcagaat tagtaagacc atttaaagt aataatcaa cgtgttgcga ttggtgtatt    780
gctgcatttg gacttacacc cagtatagct gacagtataa aaacactatt acaacaatat    840
tgtttatatt tacacattca aagtttagca tgttcatggg aatggttgt gttactatta    900
gtaagatata aatgtggaaa aaatagagaa acaattgaaa aattgctgtc taaactatta    960
tgtgtgtctc aatgtgtat gatgatagag cctccaaaat tgcgtagtac agcagcagca   1020
ttatattggt ataaaacagg tatatcaaat attagtgaag tgtatggaga cacgccagaa   1080
tggatacaaa gacaaacagt attacaacat agttttaatg attgtacatt tgaattatca   1140
cagatggtac aatgggccta cgataatgac atagtagacg atagtgaaat tgcatataa   1200
tatgcacaat tggcagacac taatagtaat gcaagtgcct ttctaaaaag taattcacag   1260
gcaaaaattg taaggattg tgcaacaatg tgtagacatt ataaacgagc agaaaaaaaa   1320
caaatgagta tgagtcaatg gataaaatat agatgtgata gggtagatga tggaggtgat   1380
tggaagcaaa ttgttatgtt tttaaggtat caaggtgtag agtttatgtc atttttaact   1440
gcattaaaaa gattttttgca aggcatacct aaaaaaaatt gcatattact atatggtgca   1500
gctaacacag ataaatcatt atttggtatg agtttaatga aatttctgca agggtctgta   1560
atatgttttg taaattctaa aagccatttt tggttacaac cattagcaga tgccaaaata   1620
ggtatgttag atgatgctac agtgccctgt tggaactata tagatgacaa tttaagaaat   1680
gcattggatg gaaatttagt ttctatggat gtaaagcata gaccattggt acaactaaaa   1740
tgccctccat tattaattac atctaacatt aatgctggta cagattctag gtggccttat   1800
ttacataata gattggtggt gtttacattt cctaatgagt ttccatttga cgaaaacgga   1860
aatccagtgt atgagcttaa tgataagaac tggaaatcct ttttctcaag gacgtggtcc   1920
agattaagtt gcacgaggaa cgaggacaag gaaaacgatg tgattcatt acctacattc   1980
aagtgcgtat ctggtcagaa cacaaatact ttgtacgtac tgctatcggc aggcacgttg   2040
atcgcactaa tgcttatcat cttcctaata acctgctgca agcgggttga taggcccgaa   2100
agtacccaaa ggtccttgag aggtaccgga cgcaacgtat cggtaacgtc gcaaagcggc   2160
```
aagttcatta gcagttggga gtcgcacaaa tcaggtggag agacccgcct gtga            2214

<210> SEQ ID NO 11
<211> LENGTH: 2241
<212> TYPE: DNA
<213> ORGANISM: artificial sequence
<220> FEATURE:
<223> OTHER INFORMATION: nucleotide sequence encoding a membrane-
      anchored and replication-defective HPV-18 E1 polypeptide
      degenerated to decrease homology with E1-encoding HPV-16 sequence

<400> SEQUENCE: 11
atgggtctca aggtgaacgt ctctgccata ttcatggcag tactgttaac tctccaaaca       60
cccaccggtc aaatccattg gggcgcagac ccagaaggca cagacggaga aggcacgggt      120
tgcaacggct ggttctacgt acaagctatt gtagacaaga agaccggaga tgtaatttct      180
gacgatgagg acgagaatgc aacagacaca gggtcggata tggttgactt cattgataca      240
caaggaacat tttgtgaaca agccgagcta gaaactgctc aggcattgtt ccatgcgcag      300
gaggtccaca tgatgcaca agtgttgcat gttttaaagc ggaagtttgc aggaggcagc      360
acagaaaaca gtccattagg ggagcggctg gaggtgGata cagagttaag cccacggtta      420
caagaaatat ctttaaatag tgggcagaaa aaggctaaga ggcggctgtt tacaatatca      480
gatagtggct acgctgttc tgaggtggaa gcaacacaga ttcaggtaac acaaatggc       540
gaacatggcg gcaatgtatg cagtggcggc agtacggagg ctatagacaa cggaggcaca      600
gagggcaaca acagcagtgt agacggtaca agcgacaata gcaatataga aaatgtaaat      660
ccacaatgta ccatagcaca attaaaagac ttgttaaaag taaacaataa caaggagct      720
atgcttgcag tattcaagga cacatatggg ctatcattta cagatttagt tagaaatttc      780
aagagtgaca aaaccacatg tacagactgg gttacagcta tattcggagt aaacccaaca      840
atcgcagaag gatttaagac tctaatacag ccatttatat tgtatgccca tatacaatgt      900
ctagactgta agtgggtgt attaatatta gccctgttgc gttacaagtg cggtaagagt      960
agactaacag ttgctaaagg tttaagtacg ttgttacacg tacctgaaac ttgcatgtta     1020
attcaaccac ctaagttacg aagtagtgtt gctgcactat actggtacag aactggaatt     1080
tctaacataa gcgaggtaat gggtgacaca cctgagtgga tcagagact actattata     1140
cagcatggaa tagacgatag caatttcgat ttgtcagaaa tggttcagtg gcatttgac     1200
aacgagctga cagatgaaag cgatatggca tttgaatacg ccttattagc tgacagcaac     1260
agcaacgcag ctgcatttt aaagagcaat tgccaagcta atatttaaa agactgtgcc     1320
actatgtgca acactatag gcgtgcccag aaacgacaga tgaatatgtc acagtggatt     1380
cgatttaggt gttcaaaaat agacgaaggg ggagactgga gaccaatagt gcaattcctg     1440
cgataccaac aaatagaatt cataacattc ttaggagcct tgaaatcatt cttaaaagga     1500
accccaaga agaactgttt agtatttgt ggaccagcaa atactgacaa gtcatattc       1560
ggaatgagct ttatacactt tatacaagga gcagttatat cattcgtgaa ctccactagt     1620
cacttctggc tggaaccgtt aacagacact aaggtggcca tgctagacga cgcaacgacc     1680
acgtgctgga catactttga tacctatatg aggaacgcgt tagacggcaa tccaataagt     1740
attgatagaa aacacaaacc tttaatcag cttaagtgtc cgccaatact actaaccaca     1800
aatatacatc cagcaaagga taatagatgg ccatacttag aaagtagaat aacagtattt     1860
gaattcccaa atgcattccc gttcgataaa atggcaacc ctgtatacga aataaacgac     1920
aaaaattgga agtgtttctt tgaaagaaca tggtcaaggt tagatttaca tgaagaagaa     1980

```
gaagatgctg atacagaggg taatccattt ggtactttca aattacgagc tggacagaat    2040
cacaggcctc ttggtttatc gagcactagc atagtctaca tcctgattgc agtgtgtctt    2100
ggagggttga tagggatccc cgctttaata tgttgctgca gggggcgttg taacaaaaag    2160
ggagaacaag ttggtatgtc aagaccaggc ctaaagcctg atcttacggg aacatcaaaa    2220
tcctatgtaa ggtcgctctg a                                              2241
```

<210> SEQ ID NO 12
<211> LENGTH: 1362
<212> TYPE: DNA
<213> ORGANISM: artificial sequence
<220> FEATURE:
<223> OTHER INFORMATION: nucleotide sequence encoding a membrane-
      anchored and replication-defective HPV-16 E2 polypeptide

<400> SEQUENCE: 12

```
atggtaccac aagcgctgtt acttgtccca ctgcttggtt tctctttatg ttttggaaaa      60
ttcccaatag agactctttg ccaacgttta atgtgtgtc aggacaaaat actaacacat     120
tatgaaaatg atagtacaga cctacgtgac catatagact attggaaaca catgcgccta     180
gcatgtgcta tttattacaa ggccagagaa atgggattta acatattaa ccaccaggtg      240 gtgccaacgc tggctgtatc aaagaataaa gcattacaag cagctgaact gcaactaacg     300
ttagaaacaa tatataactc acaatatagt aatgaaaagt ggacattaca agacgttagc     360
cttgaagtgt atttaactgc accaacagga tgtataaaaa acatggata tacagtggaa      420 gtgcagtttg atggagacat atgcaataca atgcattata caaactggac acatatatat     480
atttgtgaag aagcatcagt aactgtggta gagggtcaag ttgactatta tggttttatat     540 tatgttcatg aaggaatacg aacatatttt gtgcagttta aagatgatgc agaaaaatat     600
agtaaaaata agtatggga agttcatgcg ggtggtcagg taatattatg tcctacatct     660
gtgtttagca gcaacgaagt atcctctcct gaaattatta ggcagcactt ggccaaccac     720
cccgccgcga cccataccaa agccgtcgcc ttgggcaccg aagaaacaca gacgactatc     780
cagcgaccaa gatcagagcc agacaccgga accccctgcc acaccactaa gttgttgcac     840
agagactcag tggacagtgc tccaatcctc actgcattta acagctcaca caaggacgg      900 attaactgta atagtaacac tacacccata gtacatttaa aaggtgatgc taatacttta     960
aaatgtttaa gatatagatt taaaaagcat tgtacattgt atactgcagt gtcgtctaca    1020
tggcattgga caggacataa tgtaaaacat aaaagtgcaa ttgttacact acatatgat    1080 agtgaatggc aacgtgacca attttttgtct caagttaaaa taccaaaaac tattacagtg    1140
tctactggat ttatgtctat atatgttctt ctctctgctg aactttaat agctttaatg    1200 ttaataatat tcttaataac gtgctgtaaa agggtagacc gtccagagtc aactcagcgc    1260
agccttaggg gtactgggag aaatgttccc gtgacatcac agagtggaaa atttatctcg    1320
tcttgggaat ctcataagag tggaggcgaa acacgtcttt ga                       1362
```

<210> SEQ ID NO 13
<211> LENGTH: 1362
<212> TYPE: DNA
<213> ORGANISM: artificial sequence
<220> FEATURE:
<223> OTHER INFORMATION: nucleotide sequence encoding a membrane-
      anchored and replication-defective HPV-18 E2 polypeptide
      degeneratde to reduce homology with native HPV-16 E2-encoding
      sequence

<400> SEQUENCE: 13

```
atggttcctc aggctctcct gtttgtaccc cttctggttt ttccattgtg ttttgggaaa      60
ttccctattc agacaccgaa ggaaaccctt tcggaacgat taagttgcgt gcaagataag     120
atcatagacc actacgagaa cgacagtaaa gacatagaca gccaaataca gtactggcaa     180
ctaatacgtt gggcaaatgc aatattcttt gcagcaaggg aacatggcat acagacatta     240
aatcatcagg tagtcccagc ctataacatt tcgaaaagta aggcacataa agctgccgag     300
ctccaaatgg ccctacaagg ccttgcacaa agtcgataca aaaccgagga ttggactctg     360
caggacacat gcgaggaact atggaataca gaacctactc actgctttaa gaaaggtggc     420
caaaccgtac aagtatattt cgacggcaac aaagacaatt gtatgaccta tgtagcatgg     480
gacagtgtgt attatatgac tgatgcagga acatgggaca aaaccgctac ctgtgtaagt     540
cacaggggat tgtactacgt aaaggagggg tacaacacgt tttatataga attcaaaagt     600
gaatgtgaga agtatgggaa cacaggtacg tgggaggtac attttgggaa taatgtcatt     660
gattgtaatg actctatgtg cagtaccagt gacgacacgg tctccgctac tcagcttgtt     720
aaacagctac agcacacccc ctcaccgtat tccagcaccg tgtccgtggg aaccgcaaag     780
acctacggcc agacgtcggc tgctacacga cctggccact gtggactcgc ggagaagcag     840
cattgtggac ctgtcaaccc acttctcggt gcagctacac ctacaggcaa caacaagaga     900
cgaaaactct gcagtggtaa tacgacgcct ataatacact tgaagggaga cagaaacagt     960
ttgaagtgct acggtacagg ttgcgaaaaa catagcgacc actatagaga tatatcatcc    1020
acctggcact ggaccggtgc aggcaatgaa aaaacaggaa tactgactgt aacctaccat    1080
agcgaaacac aaagaacaaa attcttaaat actgttgcaa ttccagatag tgtacaaata    1140
ttggtgggat acatgacaat gtatgtatta ctgagtgcag gggccctgac tgccttgatg    1200
ttgataattt tcctgatgac atgttgtaga agagtcaatc gatcagaacc tacgcaacac    1260
aatctcagag ggacagggag ggaggtgtca gtcactcccc aaagcgggaa gatcatatct    1320
tcatgggaat cacacaagag tgggggtgag accagactgt ga                       1362
```

<210> SEQ ID NO 14
<211> LENGTH: 741
<212> TYPE: DNA
<213> ORGANISM: artificial sequence
<220> FEATURE:
<223> OTHER INFORMATION: Nucleotide sequence encoding a membrane-
      anchored and non-oncogenic HPV-18 E6 polypeptide degenerated to
      reduce homology with the native HPV-16 E6-encoding sequence

<400> SEQUENCE: 14

```
atggtaccgc aagccctgct attcgtacct ttattggtct ttcccctctg tttcggtaag      60
tttcctatag gatctatggc gcgctttgag gatccaacac ggcgacccta caagctacct     120
gatctgtgca cggaactgaa cacttcactg caagacatag aaataacctg tgtatattgt     180
aagacagtat tggaacttac agaggtattt gaatttgcat ttaaagacct atttgtggtg     240
tatcgtgaca gtataccccca tgccgcatgc cataagtgta gatttttta ctctagaatc     300 agagaattaa ggcactattc agactctgtg tacgagacac attggaaaaa actaactaac     360
actgggttat acaatttatt aataagatgc ctgcggtgcc agaaaccgtt gcttagacac     420
cttaatgaaa acgacgatt tcacaacata gctgggcact atagaggcca gtgccattcg     480
tgctgcaacc gagcacgaca ggaacgactc caacgacgca gggagacaca agtaagatcc     540
tacgtactgc tatcggcagg cacgttgatc gcactaatgc ttatcatctt cctaataacc     600
tgctgcaagc gggttgatag gcccgaaagt acccaaaggt ccttgagagg taccggacgc     660
```

```
aacgtatcgg taacgtcgca aagcggcaag ttcattagca gttgggagtc gcacaaatca    720
ggtggagaga cccgcctgtg a                                              741
```

<210> SEQ ID NO 15
<211> LENGTH: 585
<212> TYPE: DNA
<213> ORGANISM: artificial sequence
<220> FEATURE:
<223> OTHER INFORMATION: Nucleotide sequence encoding a membrane-
      anchored and non-oncogenic HPV-18 E7 polypeptide degenerated to
      reduce homology with the native HPV-16 E7-encoding sequence

<400> SEQUENCE: 15

```
atgggtctca aggtgaacgt ctctgccata ttcatggcag tactgttaac tctccaaaca     60
cccaccggtc aaatccattg gggcagatct atgcacggac ctaaggcaac actgcaagac    120
attgtattgc atttagagcc ccaaaatgaa attccggttg cacagttaag cgactcagag    180
gaagaaaacg acgagattga cggagttaat catcaacatt taccagcccg acgagctgaa    240
ccacaacgtc acacaatgtt gtgtatgtgc tgtaaatgcg aagccagaat tgagctggta    300
gtagagagct cagcagacga ccttcgagca ttccagcagc tatttctgaa caccctgtcc    360
tttgtctgtc cgtggtgtgc atcccagcag ggatctggtt tatcgagcac tagcatagtc    420
tacatcctga ttgcagtgtg tcttggaggg ttgataggga tccccgcttt aatatgttgc    480 tgcaggggc gttgtaacaa aaagggagaa caagttggta tgtcaagacc aggcctaaag    540
cctgatctta cgggaacatc aaaatcctat gtaaggtcgc tctga                   585
```

<210> SEQ ID NO 16
<211> LENGTH: 34
<212> TYPE: DNA
<213> ORGANISM: artificial sequence
<220> FEATURE:
<223> OTHER INFORMATION: sense primer to amplify HPV-16 E2 sequence
      from CaSki cells

<400> SEQUENCE: 16

```
aaacccggat ccatggagac tctttgccaa cgtt                                 34
```

<210> SEQ ID NO 17
<211> LENGTH: 49
<212> TYPE: DNA
<213> ORGANISM: artificial sequence
<220> FEATURE:
<223> OTHER INFORMATION: antisense primer to isolate HPV-16 E2 sequence
      from caSki cells

<400> SEQUENCE: 17

```
aaacccgaat tcaagcttag atcttcatat agacataaat ccagtagac                 49
```

<210> SEQ ID NO 18
<211> LENGTH: 33
<212> TYPE: DNA
<213> ORGANISM: artificial sequence
<220> FEATURE:
<223> OTHER INFORMATION: primer for reassambling HPV16 SS-E2mute-TMR
      sequence

<400> SEQUENCE: 18

```
aaacccggat ccatggtacc acaagcgctg tta                                  33
```

<210> SEQ ID NO 19
<211> LENGTH: 53
<212> TYPE: DNA

```
<213> ORGANISM: artificial sequence
<220> FEATURE:
<223> OTHER INFORMATION: primer for reassembilng HPV-16 SS-E2mute-TMR
      sequence

<400> SEQUENCE: 19
tctctttatg ttttggaaaa ttcccaatag agactctttg ccaacgttta aat            53

<210> SEQ ID NO 20
<211> LENGTH: 53
<212> TYPE: DNA
<213> ORGANISM: artificial sequence
<220> FEATURE:
<223> OTHER INFORMATION: primer for reassembling HPV-16 SS-E2mute-TMR
      sequence

<400> SEQUENCE: 20
atttaaacgt tggcaaagag tctctattgg gaattttcca aaacataaag aga            53

<210> SEQ ID NO 21
<211> LENGTH: 49
<212> TYPE: DNA
<213> ORGANISM: artificial sequence
<220> FEATURE:
<223> OTHER INFORMATION: primer for reassembling HPV-16 SS-E2mute-TMR
      sequence

<400> SEQUENCE: 21
cagtgtctac tggatttatg tctatatatg ttcttctctc tgctggaac                 49

<210> SEQ ID NO 22
<211> LENGTH: 49
<212> TYPE: DNA
<213> ORGANISM: artificial sequence
<220> FEATURE:
<223> OTHER INFORMATION: primer for reassembling HPV-16 SS-E2mute-TMR
      sequence

<400> SEQUENCE: 22
gttccagcag agagaagaac atatatagac ataaatccag tagacactg                 49

<210> SEQ ID NO 23
<211> LENGTH: 44
<212> TYPE: DNA
<213> ORGANISM: artificial sequence
<220> FEATURE:
<223> OTHER INFORMATION: primer for reassembling HPV-16 SS-E2mute-TMR
      sequence

<400> SEQUENCE: 23
aaacccagat cttcaaagac gtgtttcgcc tccactctta tgag                      44

<210> SEQ ID NO 24
<211> LENGTH: 34
<212> TYPE: DNA
<213> ORGANISM: artificial sequence
<220> FEATURE:
<223> OTHER INFORMATION: primer for isolating HPV-16 E1 sequence from
      CaSki cells

<400> SEQUENCE: 24
aaacccggat ccatggctga tcctgcaggt acca                                 34

<210> SEQ ID NO 25
<211> LENGTH: 34
<212> TYPE: DNA
<213> ORGANISM: artificial sequence
<220> FEATURE:
```

<223> OTHER INFORMATION: primer for isolating HPV-16 E1 sequence from
     CaSki cells

<400> SEQUENCE: 25
aaacccgaat tccattatcg taggcccatt gtac                              34

<210> SEQ ID NO 26
<211> LENGTH: 32
<212> TYPE: DNA
<213> ORGANISM: artificial sequence
<220> FEATURE:
<223> OTHER INFORMATION: primer for isolating HPV-16 E1 sequence from
     CaSki cells

<400> SEQUENCE: 26
aaacccggat ccgagacacg ccagaatgga ta                               32

<210> SEQ ID NO 27
<211> LENGTH: 50
<212> TYPE: DNA
<213> ORGANISM: artificial sequence
<220> FEATURE:
<223> OTHER INFORMATION: primer for isolating HPV-16 E1 sequence from
     CaSki cells

<400> SEQUENCE: 27
aaacccgaat tcaagcttag atcttcataa tgtgttagta ttttgtcctg            50

<210> SEQ ID NO 28
<211> LENGTH: 88
<212> TYPE: DNA
<213> ORGANISM: artificial sequence
<220> FEATURE:
<223> OTHER INFORMATION: primer for generating E1 degenerated sequence

<400> SEQUENCE: 28
aaacccagat cttcacaaag tatttgtgtt ctgaccagat acgcacttga atgtaggtaa  60
tgaatcacca tcgttttcct tgtcctcg                                    88

<210> SEQ ID NO 29
<211> LENGTH: 21
<212> TYPE: DNA
<213> ORGANISM: artificial sequence
<220> FEATURE:
<223> OTHER INFORMATION: primer for generating degenerated HPV-16 E1
     sequence

<400> SEQUENCE: 29
gatgctacag tgccctgttg g                                           21

<210> SEQ ID NO 30
<211> LENGTH: 35
<212> TYPE: DNA
<213> ORGANISM: artificial sequence
<220> FEATURE:
<223> OTHER INFORMATION: primer for reconstituting sequence encoding
     HPV-16 SS-E1 deg-TMR

<400> SEQUENCE: 30
aaacccaagg atccatggta ccgcaagccc tgcta                            35

<210> SEQ ID NO 31
<211> LENGTH: 52
<212> TYPE: DNA
<213> ORGANISM: artificial sequence
<220> FEATURE:
<223> OTHER INFORMATION: primer for reconstituting sequence encoding HPV-16 SS-E1 deg-TMR

<400> SEQUENCE: 31
ttcccctctg tttcggtaag tttcctatag ctgatcctgc aggtaccaat gg    52

<210> SEQ ID NO 32
<211> LENGTH: 52
<212> TYPE: DNA
<213> ORGANISM: artificial sequence
<220> FEATURE:
<223> OTHER INFORMATION: primer for reconstituting sequence encoding
      HPV-16 SS-E1 deg-TMR

<400> SEQUENCE: 32
ccattggtac ctgcaggatc agctatagga aacttaccga aacagagggg aa    52

<210> SEQ ID NO 33
<211> LENGTH: 50
<212> TYPE: DNA
<213> ORGANISM: artificial sequence
<220> FEATURE:
<223> OTHER INFORMATION: primer oTG17563 for reconstituting sequence
      encoding HPV-16 SS-E1

<400> SEQUENCE: 33
tatctggtca gaacacaaat actttgtacg tactgctatc ggcaggcacg    50

<210> SEQ ID NO 34
<211> LENGTH: 50
<212> TYPE: DNA
<213> ORGANISM: artificial sequence
<220> FEATURE:
<223> OTHER INFORMATION: primer oTG17564 for reconstituting sequence
      encoding HPV-16 SS-E1 deg-TMR

<400> SEQUENCE: 34
cgtgcctgcc gatagcagta cgtacaaagt atttgtgttc tgaccagata    50

<210> SEQ ID NO 35
<211> LENGTH: 42
<212> TYPE: DNA
<213> ORGANISM: artificial sequence
<220> FEATURE:
<223> OTHER INFORMATION: primer oTG17565 for reconstituting sequence
      encoding SS-E1 deg-TMR

<400> SEQUENCE: 35
aaacccaaag atcttcacag gcgggtctct ccacctgatt tg    42

<210> SEQ ID NO 36
<211> LENGTH: 33
<212> TYPE: DNA
<213> ORGANISM: artificial sequence
<220> FEATURE:
<223> OTHER INFORMATION: primer oTG15315 for reconstituting sequence
      encoding HPV-18 SS6E1 deg-TMF

<400> SEQUENCE: 36
ggggagatct atgggtctca aggtgaacgt ctc    33

<210> SEQ ID NO 37
<211> LENGTH: 39
<212> TYPE: DNA
<213> ORGANISM: artificial sequence
<220> FEATURE:
<223> OTHER INFORMATION: primer oTG17881 for reconstituting sequence
      encoding HPV-18 SS-E1 deg-TMF -continued

<210> SEQ ID NO 37
<400> SEQUENCE: 37
gtgccttctg ggtctgcgcc ccaatggatt tgaccggtg                                39

<210> SEQ ID NO 38
<211> LENGTH: 37
<212> TYPE: DNA
<213> ORGANISM: artificial sequence
<220> FEATURE:
<223> OTHER INFORMATION: primer oTG17882 for reconstituting sequence
      encoding HPV-18 SS-E1 deg-TMF

<400> SEQUENCE: 38
ggtcaaatcc attggggcgc agacccagaa ggcacag                                  37

<210> SEQ ID NO 39
<211> LENGTH: 42
<212> TYPE: DNA
<213> ORGANISM: artificial sequence
<220> FEATURE:
<223> OTHER INFORMATION: primer oTG17883 for reconstituting sequence
      encoding HPV-18 SS-E1 deg-TMF

<400> SEQUENCE: 39
cagaatcaca ggcctcttgg tttatcgagc actagcatag tc                            42

<210> SEQ ID NO 40
<211> LENGTH: 39
<212> TYPE: DNA
<213> ORGANISM: artificial sequence
<220> FEATURE:
<223> OTHER INFORMATION: primer oTG17884 for reconstituting sequence
      encoding HPV-18 SS-E1 deg-TMF

<400> SEQUENCE: 40
gctagtgctc gataaaccaa gaggcctgtg attctgtcc                                39

<210> SEQ ID NO 41
<211> LENGTH: 32
<212> TYPE: DNA
<213> ORGANISM: artificial sequence
<220> FEATURE:
<223> OTHER INFORMATION: primer oTG17885 for reconstituting sequence
      encoding HPV-18 SS-E1 deg-TMF

<400> SEQUENCE: 41
gggggcggcc gctcagagcg accttacata gg                                       32

<210> SEQ ID NO 42
<211> LENGTH: 31
<212> TYPE: DNA
<213> ORGANISM: artificial sequence
<220> FEATURE:
<223> OTHER INFORMATION: sense primer oTG17875 for reconstituting
      sequence encoding HPV-18 SS-E2 deg-TMR

<400> SEQUENCE: 42
ggggagatct atggttcctc aggctctcct g                                        31

<210> SEQ ID NO 43
<211> LENGTH: 39
<212> TYPE: DNA
<213> ORGANISM: artificial sequence
<220> FEATURE:
<223> OTHER INFORMATION: sense primer oTG17876 for reconstituting
      sequence encoding HPV-18 SS-E2 deg-TMR

<400> SEQUENCE: 43

```
gttttgggaa attccctatt cagacaccga aggaaaccc                            39
```

<210> SEQ ID NO 44
<211> LENGTH: 43
<212> TYPE: DNA
<213> ORGANISM: artificial sequence
<220> FEATURE:
<223> OTHER INFORMATION: antisense primer oTG17877 for reconstituting
      sequence encoding HPV-18 SS-E2 deg-TMR

<400> SEQUENCE: 44

```
gtttccttcg gtgtctgaat agggaatttc ccaaaacaca atg                       43
```

<210> SEQ ID NO 45
<211> LENGTH: 39
<212> TYPE: DNA
<213> ORGANISM: artificial sequence
<220> FEATURE:
<223> OTHER INFORMATION: sense primer oTG17878 for recosntituting
      sequence encoding HPV-18 SS-E2 deg-TMR

<400> SEQUENCE: 45

```
gtgggataca tgacaatgta tgtattactg agtgcaggg                            39
```

<210> SEQ ID NO 46
<211> LENGTH: 38
<212> TYPE: DNA
<213> ORGANISM: artificial sequence
<220> FEATURE:
<223> OTHER INFORMATION: antisense primer oTG17879 for reconstituting
      sequence encoding HPV-18 SS-E2 deg-TMR

<400> SEQUENCE: 46

```
ctgcactcag taatacatac attgtcatgt atcccacc                             38
```

<210> SEQ ID NO 47
<211> LENGTH: 29
<212> TYPE: DNA
<213> ORGANISM: artificial sequence
<220> FEATURE:
<223> OTHER INFORMATION: antisense primer oTG17880 for reconstituting
      sequence encoding HPV-18 SS-E2 deg-TMR

<400> SEQUENCE: 47

```
gggggcggcc gctcacagtc tggtctcac                                       29
```

<210> SEQ ID NO 48
<211> LENGTH: 83
<212> TYPE: DNA
<213> ORGANISM: artificial sequence
<220> FEATURE:
<223> OTHER INFORMATION: sense primer oTG15174 for reconstituting
      sequence encoding HPV-18 E6 deg

<400> SEQUENCE: 48

```
ggggagatct atggcgcgct ttgaggatcc aacacggcga ccctacaagc tacctgatct     60
gtgcacggaa ctgaacactt cac                                             83
```

<210> SEQ ID NO 49
<211> LENGTH: 84
<212> TYPE: DNA
<213> ORGANISM: artificial sequence
<220> FEATURE:
<223> OTHER INFORMATION: sense primer oTG15175 for reconstituting
      sequence encoding HPV-18 E6 deg

<400> SEQUENCE: 49

```
gtattggaac ttacagaggt atttgaattt gcatttaaag acctatttgt ggtgtatcgt    60
gacagtatac cccatgccgc atgc                                          84
```

<210> SEQ ID NO 50
<211> LENGTH: 85
<212> TYPE: DNA
<213> ORGANISM: artificial sequence
<220> FEATURE:
<223> OTHER INFORMATION: sense primer oTG15176 for reconstituting
      sequence encoding HPV-18 E6 deg

<400> SEQUENCE: 50

```
aggcactatt cagactctgt gtacggagac acattggaaa actaactaa cactgggtta    60 tacaatttat taataagatg cctgc                                         85
```

<210> SEQ ID NO 51
<211> LENGTH: 72
<212> TYPE: DNA
<213> ORGANISM: artificial sequence
<220> FEATURE:
<223> OTHER INFORMATION: sense primer oTG15177 for reconstituting
      sequence encoding HPV-18 E6 deg

<400> SEQUENCE: 51

```
ccttaatgaa aaacgacgat ttcacaacat agctgggcac tatagaggcc agtgccattc    60
gtgctgcaac cg                                                       72
```

<210> SEQ ID NO 52
<211> LENGTH: 76
<212> TYPE: DNA
<213> ORGANISM: artificial sequence
<220> FEATURE:
<223> OTHER INFORMATION: antisense primer oTG15178 for reconstituting
      sequence encoding HPV-18 E2 deg

<400> SEQUENCE: 52

```
ggggagatct tacttgtgtc tccctgcgtc gttggagtcg ttcctgtcgt gctcggttgc    60
agcacgaatg gcactg                                                   76
```

<210> SEQ ID NO 53
<211> LENGTH: 78
<212> TYPE: DNA
<213> ORGANISM: artificial sequence
<220> FEATURE:
<223> OTHER INFORMATION: antisense primer oTG15179 for reconstituting
      sequence encoding HPV-18 E6 deg

<400> SEQUENCE: 53

```
gttgtgaaat cgtcgttttt cattaaggtg tctaagcaac ggtttctggc accgcaggca    60
tcttattaat aaattgta                                                 78
```

<210> SEQ ID NO 54
<211> LENGTH: 82
<212> TYPE: DNA
<213> ORGANISM: artificial sequence
<220> FEATURE:
<223> OTHER INFORMATION: antisense primer oTG15180 for reconstituting
      sequence encoding HPV-18 E6 deg

<400> SEQUENCE: 54

```
cacagagtct gaatagtgcc ttaattctct gattctagag taaaaatcta tacacttatg    60
gcatgcggca tggggtatac tg                                            82
```

```
<210> SEQ ID NO 55
<211> LENGTH: 86
<212> TYPE: DNA
<213> ORGANISM: artificial sequence
<220> FEATURE:
<223> OTHER INFORMATION: antisense primer oTG15181 for reconstituting
      sequence encoding HPV-18 E6 deg

<400> SEQUENCE: 55
caaatacctc tgtaagttcc aatactgtct tacaatatac acaggttatt tctatgtctt    60
gcagtgaagt gttcagttcc gtgcac                                         86

<210> SEQ ID NO 56
<211> LENGTH: 70
<212> TYPE: DNA
<213> ORGANISM: artificial sequence
<220> FEATURE:
<223> OTHER INFORMATION: sense primer oTG14773 for reconstituting
      sequence encoding HPV-18 E7 deg

<400> SEQUENCE: 56
aaacccagat ctatgcacgg acctaaggca acactgcaag acattgtatt gcatttagag    60
ccccaaaatg                                                           70

<210> SEQ ID NO 57
<211> LENGTH: 76
<212> TYPE: DNA
<213> ORGANISM: artificial sequence
<220> FEATURE:
<223> OTHER INFORMATION: antisense primer oTG14774 for reconstituting
      sequence encoding HPV-18 E7 deg

<400> SEQUENCE: 57
aatctcgtcg ttttcttcct ctgagtcgct taactgtgca accggaattt cattttgggg    60
ctctaaatgc aataca                                                    76

<210> SEQ ID NO 58
<211> LENGTH: 76
<212> TYPE: DNA
<213> ORGANISM: artificial sequence
<220> FEATURE:
<223> OTHER INFORMATION: sense primer oTG14775 for reconstituting
      sequence encoding HPV-18 E7 deg

<400> SEQUENCE: 58
actcagagga agaaaacgac gagattgacg gagttaatca tcaacattta ccagcccgac    60
gagctgaacc acaacg                                                    76

<210> SEQ ID NO 59
<211> LENGTH: 76
<212> TYPE: DNA
<213> ORGANISM: artificial sequence
<220> FEATURE:
<223> OTHER INFORMATION: antisense primer oTG14776 for reconstituting
      sequence encoding HPV-18 E7 deg

<400> SEQUENCE: 59
ctagctcaat tctggcttcg catttacagc acatacacaa cattgtgtga cgttgtggtt    60
cagctcgtcg ggctgg                                                    76

<210> SEQ ID NO 60
<211> LENGTH: 76
<212> TYPE: DNA
<213> ORGANISM: artificial sequence
<220> FEATURE:
```

```
<223> OTHER INFORMATION: sense primer oTG14777 for reconstituting
      sequence encoding HPV-18 E7 deg

<400> SEQUENCE: 60
taaatgcgaa gccagaattg agctagtagt agagagctca gcagacgacc ttcgagcatt    60
ccagcagcta tttctg                                                    76

<210> SEQ ID NO 61
<211> LENGTH: 79
<212> TYPE: DNA
<213> ORGANISM: artificial sequence
<220> FEATURE:
<223> OTHER INFORMATION: antisense primer oTG14778 for reconstituting
      sequence encoding HPV-18 E7 deg

<400> SEQUENCE: 61
aaacccggat ccctgctggg atgcacacca cggacagaca aaggacaggg tgttcagaaa    60
tagctgctgg aatgctcga                                                 79

<210> SEQ ID NO 62
<211> LENGTH: 20
<212> TYPE: DNA
<213> ORGANISM: artificial sequence
<220> FEATURE:
<223> OTHER INFORMATION: primer sens polylinker

<400> SEQUENCE: 62
cctgcagaag cttcccgggg                                                20

<210> SEQ ID NO 63
<211> LENGTH: 28
<212> TYPE: DNA
<213> ORGANISM: artificial sequence
<220> FEATURE:
<223> OTHER INFORMATION: anstisense primer polylinker

<400> SEQUENCE: 63 gatccccgg gaagcttctg caggagct                                        28

<210> SEQ ID NO 64
<211> LENGTH: 243
<212> TYPE: PRT
<213> ORGANISM: artificial sequence
<220> FEATURE:
<223> OTHER INFORMATION: HPV-16 membrane-presented and non-oncogenic E6
      variant (SS-16E6-TMF)

<400> SEQUENCE: 64

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Met His Gln Lys
            20                  25                  30

Arg Thr Ala Met Phe Gln Asp Pro Gln Glu Arg Pro Arg Lys Leu Pro
        35                  40                  45

Gln Leu Cys Thr Glu Leu Gln Thr Thr Ile His Asp Ile Ile Leu Glu
    50                  55                  60

Cys Val Tyr Cys Lys Gln Gln Leu Leu Arg Arg Glu Val Tyr Asp Phe
65                  70                  75                  80

Ala Phe Arg Asp Leu Cys Ile Val Tyr Arg Asp Gly Asn Pro Tyr Ala
                85                  90                  95

Val Cys Asp Lys Cys Leu Lys Phe Tyr Ser Lys Ile Ser Glu Tyr Arg
            100                 105                 110
```

His Tyr Cys Tyr Ser Leu Tyr Gly Thr Thr Leu Glu Gln Gln Tyr Asn
            115                 120                 125

Lys Pro Leu Cys Asp Leu Leu Ile Arg Cys Ile Asn Cys Gln Lys Pro
        130                 135                 140

Leu Gln Arg His Leu Asp Lys Lys Gln Arg Phe His Asn Ile Arg Gly
145                 150                 155                 160

Arg Trp Thr Gly Arg Cys Met Ser Cys Arg Ser Ser Arg Thr Arg
                165                 170                 175

Arg Glu Thr Gln Leu Gly Leu Ser Ser Thr Ser Ile Val Tyr Ile Leu
                180                 185                 190

Ile Ala Val Cys Leu Gly Gly Leu Ile Gly Ile Pro Ala Leu Ile Cys
            195                 200                 205

Cys Cys Arg Gly Arg Cys Asn Lys Lys Gly Glu Gln Val Gly Met Ser
        210                 215                 220

Arg Pro Gly Leu Lys Pro Asp Leu Thr Gly Thr Ser Lys Ser Tyr Val
225                 230                 235                 240

Arg Ser Leu

<210> SEQ ID NO 65
<211> LENGTH: 185
<212> TYPE: PRT
<213> ORGANISM: artificial sequence
<220> FEATURE:
<223> OTHER INFORMATION: HPV-16 membrane-presented and non-oncogenic E7
      variant (SS-16E7-TMR)

<400> SEQUENCE: 65

Met Val Pro Gln Ala Leu Leu Phe Val Pro Leu Leu Val Phe Pro Leu
1               5                   10                  15

Cys Phe Gly Lys Phe Pro Ile Gly Ser Met His Gly Asp Thr Pro Thr
            20                  25                  30

Leu His Glu Tyr Met Leu Asp Leu Gln Pro Glu Thr Thr Gln Leu Asn
        35                  40                  45

Asp Ser Ser Glu Glu Glu Asp Glu Ile Asp Gly Pro Ala Gly Gln Ala
    50                  55                  60

Glu Pro Asp Arg Ala His Tyr Asn Ile Val Thr Phe Cys Cys Lys Cys
65                  70                  75                  80

Asp Ser Thr Leu Arg Leu Cys Val Gln Ser Thr His Val Asp Ile Arg
                85                  90                  95

Thr Leu Glu Asp Leu Leu Met Gly Thr Leu Gly Ile Val Cys Pro Ile
            100                 105                 110

Cys Ser Gln Lys Pro Arg Ser Tyr Val Leu Leu Ser Ala Gly Ala Leu
        115                 120                 125

Thr Ala Leu Met Leu Ile Ile Phe Leu Met Thr Cys Cys Arg Arg Val
    130                 135                 140

Asn Arg Ser Glu Pro Thr Gln His Asn Leu Arg Gly Thr Gly Arg Glu
145                 150                 155                 160

Val Ser Val Thr Pro Gln Ser Gly Lys Ile Ile Ser Ser Trp Glu Ser
                165                 170                 175

His Lys Ser Gly Gly Glu Thr Arg Leu
            180                 185

<210> SEQ ID NO 66
<211> LENGTH: 1062
<212> TYPE: DNA
<213> ORGANISM: artificial sequence
<220> FEATURE:
<223> OTHER INFORMATION: nucleotide sequence encoding a replication-defective HPV-33 E2 polypeptide (degenerated sequence)

<400> SEQUENCE: 66

| | |
|---|---|
| atggaggaaa tatcagcacg cttgaatgca gtccaagaga aaattctaga tctttacgaa | 60 |
| gcagataaaa ctgatttacc atctcaaatt gaacactgga aattgatacg catggcctgc | 120 |
| gctttattgt atacagccaa acagatgggc ttttcacatt tatgtcacca agtggtacct | 180 |
| tctttgttag catccaaaac caaagcgttt caagtagcgg aactacagat ggcattagag | 240 |
| acattaagta aatcacagta tagcacaagc caatggacgt tgcaacagac aagcttagag | 300 |
| gtttggcttt gtgaaccacc aaaatgtttt aaaaagcaag gagaaacagt aactgtgcaa | 360 |
| tatgacaatg acaaaaaaaa taccatggac tatactaact ggggtgaaat atacattata | 420 |
| gaggaagata catgtactat ggttacaggg aaagtagatt atataggtat gtattacata | 480 |
| cataactgtg aaaaggtata ctttaaatat tttaaggagg atgctgccaa atactctaaa | 540 |
| acacaaatgt gggaagtcca gtaggtggc caggttattg tttgccctac gtctatatct | 600 |
| agcaatcaaa tatccactac tgagactgct gacatacaga cagacaacga taaccgacca | 660 |
| ccacaagcag cggccaaacg acgacgacct gcagacacta ctgacaccgc ccagcccctt | 720 |
| acaaagctgt tctgtgcaga ccccgccttg gataatagaa cagcacgtac agcaactaac | 780 |
| tgcacaaata gcagcggac tgtgtgtagt tctaacgttg caccaatagt gcatttgaaa | 840 |
| ggcgaatcaa atagcttaaa gtgtttgaga tacagattaa aaccttataa agagttgtac | 900 |
| agttctatgt cttcaacttg gcactggact agtgacaaca aaaatagtaa aaatggcata | 960 |
| gtaaccgtga catttgtaac tgaacagcaa caacaaatgt tcttgggtac cgtaaagata | 1020 |
| cctcctactg tgcagataag taccggattc atgaccttat aa | 1062 |

<210> SEQ ID NO 67
<211> LENGTH: 1326
<212> TYPE: DNA
<213> ORGANISM: artificial sequence
<220> FEATURE:
<223> OTHER INFORMATION: nucleotide sequence encoding a membrane-
      presented and replication-defective HPV-33 E2 polypeptide
      (SS-33E2-TMR) (degenerated sequence)

<400> SEQUENCE: 67

| | |
|---|---|
| atggtaccgc aagccctgct attcgtacct ttattggtct ttccctctg tttcggtaag | 60 |
| tttcctatag aggaaatatc agcacgcttg aatgcagtcc aagagaaaat tctagatctt | 120 |
| tacgaagcag ataaaactga tttaccatct caaattgaac actggaaatt gatacgcatg | 180 |
| gcctgcgctt tattgtatac agccaaacag atgggctttt cacatttatg tcaccaagtg | 240 |
| gtaccttctt tgttagcatc caaaaccaaa gcgtttcaag tagcgaact acagatggca | 300 |
| ttagagacat taagtaaatc acagtatagc acaagccaat ggacgttgca acagacaagc | 360 |
| ttagaggttt ggctttgtga accaccaaaa tgttttaaaa agcaaggaga aacagtaact | 420 |
| gtgcaatatg acaatgacaa aaaaatacc atggactata ctaactgggg tgaaatatac | 480 |
| attatagagg aagatacatg tactatggtt acagggaaag tagattatat aggtatgtat | 540 |
| tacatacata actgtgaaaa ggtatacttt aaatatttta aggaggatgc tgccaaatac | 600 |
| tctaaaacac aaatgtggga agtccatgta gtggccagg ttattgtttg ccctacgtct | 660 |
| atatctagca atcaaatatc cactactgag actgctgaca tacagacaga caacgataac | 720 |
| cgaccaccac aagcagcggc caaacgacga cgacctgcag acactactga caccgcccag | 780 |
| ccccttacaa agctgttctg tgcagacccc gccttggata atagaacagc acgtacagca | 840 |

```
actaactgca caaataagca gcggactgtg tgtagttcta acgttgcacc aatagtgcat    900
ttgaaaggcg aatcaaatag cttaaagtgt ttgagataca gattaaaacc ttataaagag    960
ttgtacagtt ctatgtcttc aacttggcac tggactagtg acaacaaaaa tagtaaaaat   1020
ggcatagtaa ccgtgacatt tgtaactgaa cagcaacaac aaatgttctt gggtaccgta   1080 aagataccte ctactgtgca gataagtacc ggattcatga ccttatacgt actgctatcg   1140
gcaggcacgt tgatcgcact aatgcttatc atcttcctaa taacctgctg caagcgggtt   1200
gataggcccg aaagtaccca aggtccttg agaggtaccg gacgcaacgt atcggtaacg    1260
tcgcaaagcg gcaagttcat tagcagttgg gagtcgcaca aatcaggtgg agagacccgc   1320
ctgtga                                                              1326

<210> SEQ ID NO 68
<211> LENGTH: 1107
<212> TYPE: DNA
<213> ORGANISM: artificial sequence
<220> FEATURE:
<223> OTHER INFORMATION: nucleotide sequence encoding a replication-
      defective HPV-52 E2 polypeptide (52degE2) (degenerated sequence)

<400> SEQUENCE: 68
atggaatcga taccggcacg gttaaacgct gtgcaggaaa agatactcga tctatatgag     60
gctgacagca atgatctaaa cgcacaaatc gagcattgga gttgactcg aatggcttgt    120 gttttgtttt ataaagcaaa ggaactggga ataactcata taggccatca agtagtgcct    180
ccaatggcag tgtctaaggc aaaggcctgc caagccgcag agcttcaatt ggctttggag    240
gcattgaaca aaactcaata cagtacagat ggctggacct tacagcaaac aagtctagaa    300
atgtggcgtg cagagccaca aaaatacttc aagaagcacg gtacacaat  aacagtccaa    360 tacgataatg ataaaaacaa cactatggat tacacaaatt ggaaggaaat ttatttactt    420
ggtgagtgtg aatgcacaat tgtagaagga caagtggatt actatgggtt atactattgg    480
tgtgatggag aaaaaatcta tttcgtaaaa tttagtaacg acgcaaagca atattgtgta    540
acaggagtct gggaggtgca cgtgggcggt caagtaatcg tgtgtccagc atcggtatca    600
agtaacgagg tttctactac agaaacagct gtccaccat gcaccgaaac ctccaagacc    660
tccgcagtgt ccgtgggtgc caaagacaca cacctacaac caccacagaa gcgacgtcga    720
ccagatgtca cagattccag aaacaccaag taccccaaca accttttgcg gggacaacaa    780
tccgttgaca gcactacacg gggactcgta actgccactg agtgcactaa taaaggtcgg    840
gttgcacata caacttgtac tgctcctatt attcacctaa agggtgaccc caacagcttg    900
aaatgcctaa ggtatagggt aaaaacacat aaaagtttat atgttcaaat ttcatctacg    960
tggcattgga cgagtaatga atgtacaaat aataaactag gtattgtaac aataacgtac   1020
agtgatgaga cacagcgtca acagtttta aaaactgtca aatcccaaa  taccgtccaa   1080 gttatacaag gtgtcatgtc attgtaa                                      1107

<210> SEQ ID NO 69
<211> LENGTH: 1374
<212> TYPE: DNA
<213> ORGANISM: artificial sequence
<220> FEATURE:
<223> OTHER INFORMATION: nucleotide sequence encoding a membrane-
      presented and replication-defective HPV-52 E2 polypeptide
      (SS-52E2-TMF) (degenerated sequence)

<400> SEQUENCE: 69
atgggtctca aggtgaacgt ctctgccata ttcatggcag tactgttaac tctccaaaca     60
```

```
cccaccggtc aaatccattg gggcgaatcg ataccggcac ggttaaacgc tgtgcaggaa    120
aagatactcg atctatatga ggctgacagc aatgatctaa acgcacaaat cgagcattgg    180
aagttgactc gaatggcttg tgttttgttt tataaagcaa aggaactggg aataactcat    240
ataggccatc aagtagtgcc tccaatggca gtgtctaagg caaaggcctg ccaagccgca    300
gagcttcaat tggctttgga ggcattgaac aaaactcaat acagtacaga tggctggacc    360
ttacagcaaa caagtctaga aatgtggcgt gcagagccac aaaaatactt caagaagcac    420
gggtacacaa taacagtcca atacgataat gataaaaaca cactatgga ttacacaaat    480 tggaaggaaa tttatttact tggtgagtgt gaatgcacaa ttgtagaagg acaagtggat    540
tactatgggt tatactattg gtgtgatgga gaaaaaatct atttcgtaaa atttagtaac    600
gacgcaaagc aatattgtgt aacaggagtc tgggaggtgc acgtgggcgg tcaagtaatc    660
gtgtgtccag catcggtatc aagtaacgag gtttctacta cagaaacagc tgtccaccta    720
tgcaccgaaa cctccaagac ctccgcagtg tccgtgggtg ccaagacac acacctacaa    780 ccaccacaga agcgacgtcg accagatgtc acagattcca gaaacaccaa gtaccccaac    840
aaccttttgc ggggacaaca atccgttgac agcactacac ggggactcgt aactgccact    900
gagtgcacta ataaaggtcg ggttgcacat acaacttgta ctgctcctat tattcaccta    960
aagggtgacc ccaacagctt gaaatgccta aggtataggg taaaacacac taaaagttta   1020
tatgttcaaa tttcatctac gtggcattgg acgagtaatg aatgtacaaa taataaacta   1080
ggtattgtaa caataacgta cagtgatgag acacagcgtc aacagttttt aaaaactgtc   1140
aaaatcccaa ataccgtcca agttatacaa ggtgtcatgt cattgggttt atcgagcact   1200
agcatagtct acatcctgat tgcagtgtgt cttggagggt tgatagggat ccccgcttta   1260
atatgttgct gcagggggcg ttgtaacaaa aagggagaac aagttggtat gtcaagacca   1320
ggcctaaagc ctgatcttac gggaacatca aaatcctatg taaggtcgct ctga          1374

<210> SEQ ID NO 70
<211> LENGTH: 441
<212> TYPE: PRT
<213> ORGANISM: artificial sequence
<220> FEATURE:
<223> OTHER INFORMATION: membrane-presented and replication-defective
      HPV-33 E2 polypeptide (SS-33E2-TMR)

<400> SEQUENCE: 70

Met Val Pro Gln Ala Leu Leu Phe Val Pro Leu Leu Val Phe Pro Leu
1               5                   10                  15

Cys Phe Gly Lys Phe Pro Ile Glu Glu Ile Ser Ala Arg Leu Asn Ala
            20                  25                  30

Val Gln Glu Lys Ile Leu Asp Leu Tyr Glu Ala Asp Lys Thr Asp Leu
        35                  40                  45

Pro Ser Gln Ile Glu His Trp Lys Leu Ile Arg Met Ala Cys Ala Leu
    50                  55                  60

Leu Tyr Thr Ala Lys Gln Met Gly Phe Ser His Leu Cys His Gln Val
65                  70                  75                  80

Val Pro Ser Leu Leu Ala Ser Lys Thr Lys Ala Phe Gln Val Ala Glu
                85                  90                  95

Leu Gln Met Ala Leu Glu Thr Leu Ser Lys Ser Gln Tyr Ser Thr Ser
            100                 105                 110

Gln Trp Thr Leu Gln Gln Thr Ser Leu Glu Val Trp Leu Cys Glu Pro
        115                 120                 125
```

-continued

```
Pro Lys Cys Phe Lys Lys Gln Gly Glu Thr Val Thr Val Gln Tyr Asp
    130                 135                 140

Asn Asp Lys Lys Asn Thr Met Asp Tyr Thr Asn Trp Gly Glu Ile Tyr
145                 150                 155                 160

Ile Ile Glu Glu Asp Thr Cys Thr Met Val Thr Gly Lys Val Asp Tyr
                165                 170                 175

Ile Gly Met Tyr Tyr Ile His Asn Cys Glu Lys Val Tyr Phe Lys Tyr
            180                 185                 190

Phe Lys Glu Asp Ala Ala Lys Tyr Ser Lys Thr Gln Met Trp Glu Val
        195                 200                 205

His Val Gly Gly Gln Val Ile Val Cys Pro Thr Ser Ile Ser Ser Asn
    210                 215                 220

Gln Ile Ser Thr Thr Glu Thr Ala Asp Ile Gln Thr Asp Asn Asp Asn
225                 230                 235                 240

Arg Pro Pro Gln Ala Ala Ala Lys Arg Arg Arg Pro Ala Asp Thr Thr
                245                 250                 255

Asp Thr Ala Gln Pro Leu Thr Lys Leu Phe Cys Ala Asp Pro Ala Leu
            260                 265                 270

Asp Asn Arg Thr Ala Arg Thr Ala Thr Asn Cys Thr Asn Lys Gln Arg
        275                 280                 285

Thr Val Cys Ser Ser Asn Val Ala Pro Ile Val His Leu Lys Gly Glu
    290                 295                 300

Ser Asn Ser Leu Lys Cys Leu Arg Tyr Arg Leu Lys Pro Tyr Lys Glu
305                 310                 315                 320

Leu Tyr Ser Ser Met Ser Ser Thr Trp His Trp Thr Ser Asp Asn Lys
                325                 330                 335

Asn Ser Lys Asn Gly Ile Val Thr Val Thr Phe Val Thr Glu Gln Gln
            340                 345                 350

Gln Gln Met Phe Leu Gly Thr Val Lys Ile Pro Pro Thr Val Gln Ile
        355                 360                 365

Ser Thr Gly Phe Met Thr Leu Tyr Val Leu Leu Ser Ala Gly Thr Leu
    370                 375                 380

Ile Ala Leu Met Leu Ile Ile Phe Leu Ile Thr Cys Cys Lys Arg Val
385                 390                 395                 400

Asp Arg Pro Glu Ser Thr Gln Arg Ser Leu Arg Gly Thr Gly Arg Asn
                405                 410                 415

Val Ser Val Thr Ser Gln Ser Gly Lys Phe Ile Ser Ser Trp Glu Ser
            420                 425                 430

His Lys Ser Gly Gly Glu Thr Arg Leu
        435                 440

<210> SEQ ID NO 71
<211> LENGTH: 457
<212> TYPE: PRT
<213> ORGANISM: artificial sequence
<220> FEATURE:
<223> OTHER INFORMATION: membrane-presented and replication-defective
      HPV-52 E2 polypeptide (SS-52E2-TMF)

<400> SEQUENCE: 71

Met Gly Leu Lys Val Asn Val Ser Ala Ile Phe Met Ala Val Leu Leu
1               5                   10                  15

Thr Leu Gln Thr Pro Thr Gly Gln Ile His Trp Gly Glu Ser Ile Pro
            20                  25                  30

Ala Arg Leu Asn Ala Val Gln Glu Lys Ile Leu Asp Leu Tyr Glu Ala
        35                  40                  45
```

```
Asp Ser Asn Asp Leu Asn Ala Gln Ile Glu His Trp Lys Leu Thr Arg
    50                  55                  60

Met Ala Cys Val Leu Phe Tyr Lys Ala Lys Glu Leu Gly Ile Thr His
65                  70                  75                  80

Ile Gly His Gln Val Val Pro Pro Met Ala Val Ser Lys Ala Lys Ala
                    85                  90                  95

Cys Gln Ala Ala Glu Leu Gln Leu Ala Leu Glu Ala Leu Asn Lys Thr
                100                 105                 110

Gln Tyr Ser Thr Asp Gly Trp Thr Leu Gln Gln Thr Ser Leu Glu Met
                115                 120                 125

Trp Arg Ala Glu Pro Gln Lys Tyr Phe Lys Lys His Gly Tyr Thr Ile
    130                 135                 140

Thr Val Gln Tyr Asp Asn Asp Lys Asn Asn Thr Met Asp Tyr Thr Asn
145                 150                 155                 160

Trp Lys Glu Ile Tyr Leu Leu Gly Glu Cys Glu Cys Thr Ile Val Glu
                165                 170                 175

Gly Gln Val Asp Tyr Tyr Gly Leu Tyr Tyr Trp Cys Asp Gly Glu Lys
                180                 185                 190

Ile Tyr Phe Val Lys Phe Ser Asn Asp Ala Lys Gln Tyr Cys Val Thr
    195                 200                 205

Gly Val Trp Glu Val His Val Gly Gly Gln Val Ile Val Cys Pro Ala
210                 215                 220

Ser Val Ser Ser Asn Glu Val Ser Thr Thr Glu Thr Ala Val His Leu
225                 230                 235                 240

Cys Thr Glu Thr Ser Lys Thr Ser Ala Val Ser Val Gly Ala Lys Asp
                245                 250                 255

Thr His Leu Gln Pro Pro Gln Lys Arg Arg Arg Pro Asp Val Thr Asp
                260                 265                 270

Ser Arg Asn Thr Lys Tyr Pro Asn Asn Leu Leu Arg Gly Gln Gln Ser
                275                 280                 285

Val Asp Ser Thr Thr Arg Gly Leu Val Thr Ala Thr Glu Cys Thr Asn
    290                 295                 300

Lys Gly Arg Val Ala His Thr Thr Cys Thr Ala Pro Ile Ile His Leu
305                 310                 315                 320

Lys Gly Asp Pro Asn Ser Leu Lys Cys Leu Arg Tyr Arg Val Lys Thr
                325                 330                 335

His Lys Ser Leu Tyr Val Gln Ile Ser Ser Thr Trp His Trp Thr Ser
                340                 345                 350

Asn Glu Cys Thr Asn Asn Lys Leu Gly Ile Val Thr Ile Thr Tyr Ser
                355                 360                 365

Asp Glu Thr Gln Arg Gln Gln Phe Leu Lys Thr Val Lys Ile Pro Asn
    370                 375                 380

Thr Val Gln Val Ile Gln Gly Val Met Ser Leu Gly Leu Ser Ser Thr
385                 390                 395                 400

Ser Ile Val Tyr Ile Leu Ile Ala Val Cys Leu Gly Gly Leu Ile Gly
                405                 410                 415

Ile Pro Ala Leu Ile Cys Cys Cys Arg Gly Arg Cys Asn Lys Lys Gly
                420                 425                 430

Glu Gln Val Gly Met Ser Arg Pro Gly Leu Lys Pro Asp Leu Thr Gly
                435                 440                 445

Thr Ser Lys Ser Tyr Val Arg Ser Leu
    450                 455

<210> SEQ ID NO 72
```

```
<211> LENGTH: 36
<212> TYPE: DNA
<213> ORGANISM: artificial sequence
<220> FEATURE:
<223> OTHER INFORMATION: priler oTG18962 for reconstituting sequence
      encoding SS-33E2-TMR

<400> SEQUENCE: 72
cccaaaggat ccaccatggt accgcaagcc ctgcta                                36

<210> SEQ ID NO 73
<211> LENGTH: 52
<212> TYPE: DNA
<213> ORGANISM: artificial sequence
<220> FEATURE:
<223> OTHER INFORMATION: primer oTG18963 for reconstituting sequence
      encoding SS-33E2-TMR

<400> SEQUENCE: 73
ttcccctctg tttcggtaag tttcctatag aggaaatatc agcacgcttg aa              52

<210> SEQ ID NO 74
<211> LENGTH: 52
<212> TYPE: DNA
<213> ORGANISM: artificial sequence
<220> FEATURE:
<223> OTHER INFORMATION: primer oTG18964 for reconstituting sequence
      encoding SS-33E2-TMR

<400> SEQUENCE: 74
ttcaagcgtg ctgatatttc ctctatagga aacttaccga aacagagggg aa              52

<210> SEQ ID NO 75
<211> LENGTH: 49
<212> TYPE: DNA
<213> ORGANISM: artificial sequence
<220> FEATURE:
<223> OTHER INFORMATION: primer oTG18965 for reconstituting sequence
      encoding SS-33E2-TMR

<400> SEQUENCE: 75
gataagtacc ggattcatga ccttatacgt actgctatcg gcaggcacg                  49

<210> SEQ ID NO 76
<211> LENGTH: 49
<212> TYPE: DNA
<213> ORGANISM: artificial sequence
<220> FEATURE:
<223> OTHER INFORMATION: primer oTG18966 for reconstituting sequence
      encoding SS-33-E2-TMR

<400> SEQUENCE: 76
cgtgcctgcc gatagcagta cgtataaggt catgaatccg gtacttatc                  49

<210> SEQ ID NO 77
<211> LENGTH: 56
<212> TYPE: DNA
<213> ORGANISM: artificial sequence
<220> FEATURE:
<223> OTHER INFORMATION: primer oTG18967 for reconstituting sequence
      encoding SS-33E2-TMR

<400> SEQUENCE: 77
aaaaccccgc atgcgcggcc gcaagctatc acaggcgggt ctctccacct gatttg          56

<210> SEQ ID NO 78
<211> LENGTH: 37
<212> TYPE: DNA
```

```
<213> ORGANISM: artificial sequence
<220> FEATURE:
<223> OTHER INFORMATION: primer oTG18968 for reconstituting sequence
      encoding SS-52E2-TMF

<400> SEQUENCE: 78
aaacccgaga tctaccatgg gtctcaaggt gaacgtc                              37

<210> SEQ ID NO 79
<211> LENGTH: 46
<212> TYPE: DNA
<213> ORGANISM: artificial sequence
<220> FEATURE:
<223> OTHER INFORMATION: primer oTG18969 for reconstituting sequence
      encoding SS-52E2-TMF

<400> SEQUENCE: 79
cccaccggtc aaatccattg gggcgaatcg ataccggcac ggttaa                    46

<210> SEQ ID NO 80
<211> LENGTH: 46
<212> TYPE: DNA
<213> ORGANISM: artificial sequence
<220> FEATURE:
<223> OTHER INFORMATION: primer oTG18970 for reconstituting sequence
      encoding SS-52E2-TMF

<400> SEQUENCE: 80
ttaaccgtgc cggtatcgat tcgccccaat ggatttgacc ggtggg                    46

<210> SEQ ID NO 81
<211> LENGTH: 43
<212> TYPE: DNA
<213> ORGANISM: artificial sequence
<220> FEATURE:
<223> OTHER INFORMATION: primer oTG18971 for reconstituting sequence
      encoding SS-52E2-TMF

<400> SEQUENCE: 81
gttatacaag gtgtcatgtc attgggttta tcgagcacta gca                       43

<210> SEQ ID NO 82
<211> LENGTH: 43
<212> TYPE: DNA
<213> ORGANISM: artificial sequence
<220> FEATURE:
<223> OTHER INFORMATION: primer oTG18972 for reconstituting sequence
      encoding SS-52E2-TMF

<400> SEQUENCE: 82
tgctagtgct cgataaaccc aatgacatga caccttgtat aac                       43

<210> SEQ ID NO 83
<211> LENGTH: 53
<212> TYPE: DNA
<213> ORGANISM: artificial sequence
<220> FEATURE:
<223> OTHER INFORMATION: primer oTG18973 for reconstituting sequence
      encoding SS-52E2-TMF

<400> SEQUENCE: 83
aagcttgcta gccaccggtg gggccgcggc cgctcagagc gaccttacat agg            53

<210> SEQ ID NO 84
<211> LENGTH: 85
<212> TYPE: DNA
<213> ORGANISM: Artificial Sequence
<220> FEATURE:
```

```
<223> OTHER INFORMATION: terminal 85 nucleotides of native HPV-16 E1-
      encoding sequence

<400> SEQUENCE: 84
gcacgaggac gaggacaagg aaaacgatgg tgattcatta cctacattca agtgcgtatc    60
tggtcagaac acaaatactt tgtga                                         85

<210> SEQ ID NO 85
<211> LENGTH: 69
<212> TYPE: DNA
<213> ORGANISM: Artificial Sequence
<220> FEATURE:
<223> OTHER INFORMATION: beginning 69 nucleotides of native HPV-16 E2
      sequence

<400> SEQUENCE: 85
atggtgattc attacctaca ttcaagtgcg tatctggtca gaacacaaat actttgtgaa    60
aatgatagt                                                           69

<210> SEQ ID NO 86
<211> LENGTH: 477
<212> TYPE: DNA
<213> ORGANISM: Artificial Sequence
<220> FEATURE:
<223> OTHER INFORMATION: HPV-16 E6 encoding nucleotide sequence

<400> SEQUENCE: 86
atgcaccaaa agagaactgc aatgtttcag acccacagg agcgacccag aaagttacca     60
cagttatgca cagagctgca acaactata catgatataa attagaatg tgtgtactgc    120 aagcaacagt tactgcgacg tgaggtatat gactttgctt ttcgggattt atgcatagta   180
tatagagatg gaatccata tgctgtatgt gataaatgtt taaagttta ttctaaaatt    240 agtgagtata gacattattg ttatagtttg tatggaacaa cattagaaca gcaatacaac   300
aaaccgttgt gtgatttgtt aattaggtgt attaactgtc aaaagccact gtgtcctgaa   360
gaaaagcaaa gacatctgga caaaaagcaa agattccata atataagggg tcggtggacc   420
ggtcgatgta tgtcttgttg cagatcatca agaacacgta gagaaaccca gctgtaa      477

<210> SEQ ID NO 87
<211> LENGTH: 477
<212> TYPE: DNA
<213> ORGANISM: Artificial Sequence
<220> FEATURE:
<223> OTHER INFORMATION: HPV-18 E6 encoding sequence

<400> SEQUENCE: 87
atggcgcgct ttgaggatcc aacacggcga ccctacaagc tacctgatct gtgcacggaa    60
ctgaacactt cactgcaaga catagaaata acctgtgtat attgcaagac agtattggaa   120
cttacagagg tatttgaatt tgcatttaaa gatttatttg tggtgtatag agacagtata   180
ccccatgctg catgccataa atgtatagat ttttattcta gaattagaga attaagacat   240
tattcagact ctgtgtatgg agacacattg gaaaaactaa ctaacactgg ttatacaat    300 ttattaataa ggtgcctgcg gtgccagaaa ccgttgaatc cagcagaaaa acttagacac   360
cttaatgaaa acgacgatt tcacaacata gctgggcact atagaggcca gtgccattcg   420
tgctgcaacc gagcacgaca ggaacgactc caacgacgca gagaaacaca gtataa       477
```